(12) United States Patent
Oberste et al.

(10) Patent No.: US 6,846,621 B1
(45) Date of Patent: Jan. 25, 2005

(54) TYPING OF HUMAN ENTEROVIRUSES

(75) Inventors: Steven Oberste, Lilburn, GA (US);
Kaija Maher, Atlanta, GA (US); David R. Kilpatrick, Norcross, GA (US); Mark A. Pallansch, Lilburn, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/937,862

(22) PCT Filed: Mar. 24, 2000

(86) PCT No.: PCT/US00/07828

§ 371 (c)(1),
(2), (4) Date: Sep. 28, 2001

(87) PCT Pub. No.: WO00/58524

PCT Pub. Date: Oct. 5, 2000

Related U.S. Application Data

(60) Provisional application No. 60/127,464, filed on Mar. 31, 1999.

(51) Int. Cl.[7] .............................. C12Q 1/70; C12Q 1/68; C12Q 1/04; C12P 19/34; C07H 21/04

(52) U.S. Cl. ............................... 435/5; 435/6; 435/34; 435/91.2; 435/91.3; 435/91.32; 435/91.33; 435/40.51; 435/40.52; 536/24.33

(58) Field of Search ......................... 435/5, 6, 34, 91.2, 435/91.3, 91.32, 91.33; 536/24.33

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,717,653 A | 1/1988 | Webster et al. | 435/5 |
| 4,965,188 A | 10/1990 | Mullis et al. | 435/6 |
| 5,075,212 A | 12/1991 | Rotbart | 435/5 |
| 5,185,243 A | 2/1993 | Ullman et al. | 435/6 |
| 5,268,465 A | 12/1993 | Bredt et al. | 435/252.3 |
| 5,516,641 A | 5/1996 | Ullman et al. | 435/6 |
| 5,545,522 A | 8/1996 | Van Gelder et al. | 435/6 |
| 5,578,467 A | 11/1996 | Schuster et al. | 435/91.2 |
| 5,585,477 A | 12/1996 | Kilpatrick | 536/23.72 |
| 5,624,833 A | 4/1997 | Gelfand et al. | 435/194 |
| 5,691,134 A | 11/1997 | Kilpatrick | 435/5 |
| 5,723,031 A | 3/1998 | Durr et al. | 204/457 |
| 5,726,012 A | 3/1998 | Bacheler et al. | 435/5 |
| 5,789,208 A | 8/1998 | Sharon | 435/91.41 |

FOREIGN PATENT DOCUMENTS

| | | | |
|---|---|---|---|
| WO | WO 98/14611 | * | 4/1998 |
| WO | WO 99/53097 | | 10/1999 |

OTHER PUBLICATIONS

Sequence alignment of instant SEQ ID NO: 85 with SEQ ID NO: 19947 of US Patent 6,551,795 in the Issued Patents AA database with an earliest prior filing date of Feb. 18, 1998.*
Sequence alignment of instant SEQ ID NO: 85 with SwissProt database accession No: P12915 submitted Oct. 1, 1998.*
Kilpatrick et al. Journal of Clinical Microbiology. Feb. 1998; 36 (2): 352–357.*
Kilpatrick et al. Journal of Clinical Microbiology. 1996; 34 (12): 2990–2996.*
Geneseq database sequence alignment of instant SEQ ID NO: 22 with accession No: AAV34811; entry date: Sep. 24, 1998; primer 43A from WO 98/14611 of Kilpatrick.*
Oberste et al. Molecular Evolution of the Human Enteroviruses: Correlation of Serotype with VP1 Sequence and Application to Picornavirus Classification. *J. Virol.* 73(3):1941–1948 (Mar. 1999).
Oberste et al. Typing of Human Enteroviruses by Partial Sequencing of VP1. *J. Clin. Microbiol.* 37(5):1288–1293 (May, 1999).
CDC. Nonpolio Enterovirus Surveillance—U.S.. 1993–1996. MMWR 46(32):748–750 (Aug. 15, 1997).
Mateu. Antibody recognition of picornaviruses and escape from neutralization: a structural view. *Virus Res.* 38:1–24 (1995).
Drebot et al. Molecular Epidemiology of Enterovirus Outbreaks in Canada During 1991–1992: Identification of Echovirus 30 and Coxsackievirus B1 Strains by Amplicon Sequencing. *J. Med. Virol.* 44:340–347 (1994).
Arola et al. Identification of Enteroviruses in Clinical Specimens by Competitive PCR Followed by Genetic Typing Using Sequence Analysis. *J. Clin. Microbiol.* 34(2):313–318 (Feb. 1996).
Oberste et al. Molecular phylogeny of all human enterovirus serotypes based on comparison of sequences at the 5' end of the region encoding VP2. *Virus Res.* 58:35–43 (1998).

(List continued on next page.)

*Primary Examiner*—Shanon Foley
(74) *Attorney, Agent, or Firm*—Needle & Rosenberg, P.C.

(57) ABSTRACT

The present invention discloses a method for detecting the presence of an enterovirus in a clinical sample. The invention additionally discloses a method for typing an enterovirus in a clinical sample. Both methods employ a set of primer oligonucleotides for reverse transcription and amplification that hybridize to conserved regions of the enterovirus genome, and that provide amplicons that include significant portions of the VP1 region that are characteristic of the various serotypes. In the typing method, the invention further provides a database consisting of nucleotide sequences from prototypical enteroviral serotypes, which is used to type the clinical sample by comparing the sequence of its amplicon with each prototypical sequence in the database. The invention additionally provides mixtures of primer oligonucleotides, and a kit for use in conducting the typing method that includes a mixture of the primer oligonucleotides.

8 Claims, 2 Drawing Sheets

OTHER PUBLICATIONS

Figure 1:
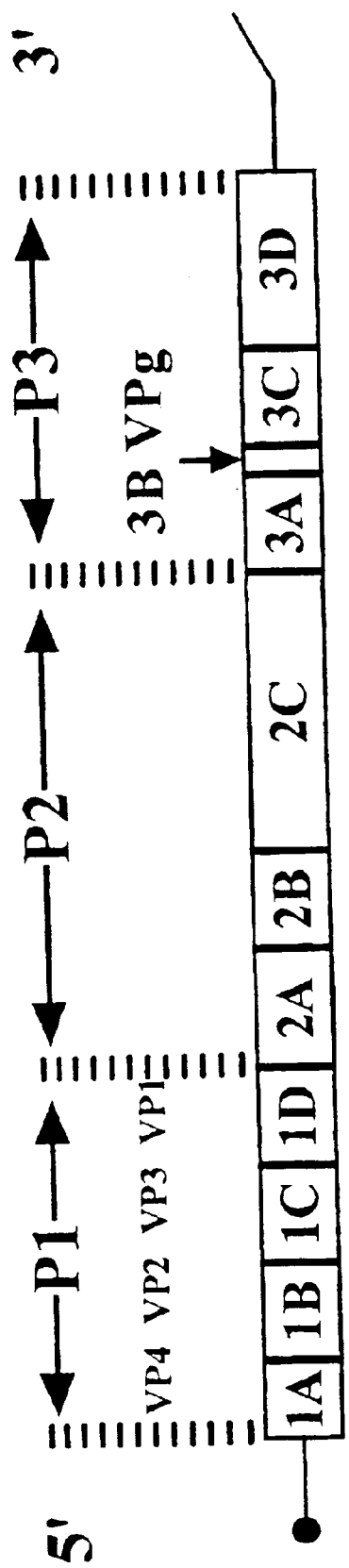

Kopecka et al. Genotypic variation in Coxsackievirus 85 isolates from three different outbreaks in the United States. *Virus Res.* 38:125–136 (1995).

Diedrich et al., Sequence Comparison of Echovirus Type 30 Isolates to Other Enteroviruses in the 5'Noncoding Region. *J. Med. Virol.* 46:148–152 (1995).

Bailly et al. Natural Isolates of ECHO Virus Type 25 with Extensive Variations in IRES Sequences and Different Translational Efficiencies. *Virology* 215:83–96 (1996).

Holland et al. Differentiation and Characterization of Enteroviruses by Computer–Assisted Viral Protein Fingerprinting. *J. Clin. Microbiol.* 36(6):1588–1594 (Jun. 1998).

Melnick et al. Lyophilized combination pools of enterovirus equine antisera: preparation and test procedures for the identification of field strains of 42 enteroviruses. *Bull. W.H.O.* 48:263–268 (1973).

Rotbart et al. Laboratory Diagnosis of Enteroviral Infections. In *Human Enterovirus Infections* (Rotbart. Eds) ASM Press. Washington, D.C. pp. 401–418 (1995).

Needleman et al., A General Method Applicable to the Search for Similarities in the Amino Acid Sequences of Two Proteins. *J. Mol. Biol.* 48:443–453 (1970).

Rorbart et al. Diagnosis of Enterovirus Infection by Polymerase Chain Reaction of Multiple Specimen Types. *Ped. Infect. Dis.* 16(4):409–411 (Apr. 1997).

Alksnis et al. *Use of synthetic oligodeoxyribonucleotides for type–specific identification of coxsackie B viruses. Mol. Cell. Probes* 3:103–108 (1989).

Petitjean et al. Specific detection of enteroviruses in clinical samples by molecular hybridization using poliovirus subgenomic riboprobes. *J. Clin. Microbiol.* 28(2):307–311 (1990).

Melnick. The discovery of the enteroviruses and the classification of poliovirus among them. *Biologicals* 21:305–309 (1993).

Clements et al. Detection of Enterovirus–Specific RNA in Serum: The Relationship to Chronic Fatigue, *J. Med. Virol.* 45:156–161 (1995).

Rotbart et al. Development and application of RNA probes for the study of picornaviruses. *Mol. Cell. Probes* 2:65–73 (1988).

Rotbart. Enzymatic RNA amplication of the enteroviruses. *J. Clin. Microbiol.* 28(3):438–442 (Mar. 1990).

Chapman et al. Molecular detection and identification of enteroviruses using enzymatic amplification and nucleic acid hybridization. *J. Clin. Microbiol.* 28(5):843–850 (May. 1990).

Hyypia et al. Polymerase chain reaction for human picornaviruses. *J. Gen. Virol.* 70:3261–3268 (1989).

Olive et al. Detection and differentiation of picornaviruses in clinical samples following genomic amplification. *J. Gen. Virol.* 71:2141–2147 (1990).

Gilmaker et al. Detection of enteroviral RNA by polymerase chain reaction in faecal samples from patients with aseptic meningitis. *J. Med. Virol.* 38:54–61 (1992).

Yang et al. Genotype–specific in vitro amplification of sequences of the wild type 3 polioviruses from Mexico and Guatemala. *Virus Res.* 24:277–296 (Aug. 1992).

Zoll et al. General primer–mediated polymerase chain reaction for detection of enteroviruses: application for diagnostic routine and persistent infections. *J. Clin. Microbiol.* 30(1):160–165 (Jan. 1992).

Muir et al. Rapid diagnosis of enterovirus infection by magnetic bead extraction and polymerase chain reaction detection of enterovirus RNA in clinical specimens. *J. Clin. Microbiol.* 31(1):31–38 (Jan. 1993).

Rotbart et al. Diagnosis of enteroviral meningitis by using PCR with a colorimetric microwell detection assay. *J. Clin. Microbiol.* 32(10):2590–2592 (Oct. 1994).

Cova et al. Use of cRNA probes for the detection of enteroviruses by molecular hybridization. *J. Med. Virol.* 24:11–18 (Jan. 1988).

Kim et al. Nucleotide sequencing of a part of the 5–noncoding region of echovirus type 9 and rapid virus detection during the acute phase of aseptic meningitis. *Arch. Virol.* 142:853–860 (1997).

Santti et al. Molecular detection and typing of human picornaviruses. *Virus Res.* 62:177–183 (1999).

Casas et al. Molecular Characterization of Human Enteroviruses in Clinical Samples: Comparison Between VP2. VP1. and RNA Polymerase Regions Using RT Nested PCR Assays and Direct Sequencing of Products. *J. Med. Virol.* 65:138–148 (2001).

Caro et al. *Molecular strategy for 'serotyping' of human enteroviruses.* J. Gen. Virol. 82:79–91 (2001).

Norder et al. *Homotypic Echoviruses Share Aminoterminal VP1 Sequence Homology Applicable for Typing.* J. Med. Virol. 63:35–44 (2001).

Oberste et al. *Comparison of Classic and Molecular Approaches for the Identification of untypeable Enteroviruses.* J. Clin. Microbiol. 38(3):1170–1174 (Mar. 2000).

Oberste et al. *Identification and genetic analysis of Panama–genotype Venezuelan equine encephalitis virus subtype ID in Peru.* Am. J. Trop. Med. Hyg. 58(1):41–46 (1998).

* cited by examiner

TYPING OF HUMAN ENTEROVIRUSES

The present application is a 35 U.S.C. § 371 national phase application from, and claims priority to, international application PCT/US00/07828, filed Mar. 24, 2000 (published under PCT Article 21(2) in English), which claims priority to U.S. provisional patent application Ser. No. 60/127,464, filed Mar. 31, 1999, which applications are hereby incorporated herein in their entirety by reference.

FIELD OF THE INVENTION

The present invention relates to methods of detecting the presence, and of establishing the serotype, or serovar, of an enterovirus that may be present in a clinical sample or a biological sample, as well as to a kit that includes primers that may be used in the methods. The methods include amplification of viral RNA, and sequencing of the resulting amplicons.

BACKGROUND OF THE INVENTION

Enteroviruses constitute a broad range of pathogens etiologically responsible for a wide range of diseases in humans, as well as in other animals. The genus *Enterovirus* is a member of the family *Picornaviridae*. As the family name indicates, enteroviruses are small RNA viruses; they contain positive single stranded RNA as the genome. Five groups are found within the enteroviruses: coxsackievirus A (CA), coxsackievirus B (CB), echovirus (E), and numbered enteroviruses (EV), as well as poliovirus (PV). There are 66 serotypes currently classified among the human enteroviruses, although two serotypes, E22 and E23, are to be reclassified in a different genus.

The viral genome is shown schematically in FIG. 1. The single stranded RNA comprises a 5' nontranslated region (single line), which is followed by an open reading frame coding for a polyprotein precursor of Mr $240-250 \times 10^3$ Da (boxed portion), followed by a 3' noncoding sequence and a poly (A) tract (single line). In the polyprotein, the sequence of gene products begins 1A, 1B, 1C, 1D, and 2A. 1A through 1D are, respectively, the structural proteins VP4, VP2, VP3, and VP1 of the viral capsid; VP1 is followed in the open reading frame by a nonstructural protein 2A.

The various members of the human enteroviruses cause a wide range of symptoms, syndromes and diseases. These include acute benign pericarditis, acute flaccid paralysis, acute hemorrhagic conjunctivitis, aseptic meningitis, various exanthemas, carditis, croup, encephalitis, enanthema, gastrointestinal disease, hepatitis, hand-foot-and-mouth disease, various respiratory diseases, myocarditis, neonatal disease including multi-organ failure, pericarditis, pleurodynia, rash, and undifferentiated fever. In general, the syndromes are not correlated with particular enterovirus serotypes, nor does a serotype specifically correlate with a particular disease, although in certain cases serotypes do correlate with particular diseases.

Enteroviruses are responsible for large numbers of infections. There may be between 30 million to 50 million illnesses that are ascribable to enteroviruses each year in the United States (CDC; MMWR 46:748–750; Strikas et al. J. Infect. Dis. 146:346–351 (1986); Rotbart in Human Enterovims Infections, H. A. Rotbart (ed.) ASM Press, Washington, D.C., pp. 401–418 (1995)). After rhinoviruses, enteroviruses are the most common viral infection in humans. Enteroviral infections lead to 30,000 to 50,000 hospitalizations each year for aseptic meningitis, myocarditis, encephalitis, acute hemorrhagic conjunctivitis, nonspecific febrile illnesses, and upper respiratory infections (Melnick, Biologicals 21:305–309 (1993); Morens et al. in Human Enterovirus Infections, H. A. Rotbart (ed.) ASM Press, Washington, D.C., pp. 3–23 (1995); Melnick in Fields Virology (B. N. Fields et al. (eds.) 3rd ed., Lippincott-Raven Publishers, Philadelphia, pp. 655–712 (1996)). Enteroviruses are also implicated in acute flaccid paralysis in animal models, as well as in dilated cardiomyopathy. The six serotypes of coxsackie B viruses are implicated in a variety of clinical diseases, such as meningitis, myocarditis and severe neonatal disease. Recently, enterovirus infection has been linked to chronic fatigue syndrome (Elements et al., J. Med. Virol. 45:156–161 (1995)).

Poliovirus is also an enterovirus that infects humans. Three serotypes, PV1, PV2, and PV3 are known. A non-enteroviral picornavirus that also afflicts humans is human rhinovirus (HRV), responsible for many common cold infections; several serotypes have been identified. Additionally, picornaviruses affect mammals other than humans, including viruses such as bovine enterovirus (BEV) and simian picornavirus (SPV).

It is important to identify the serotype of an enterovirus infection in a subject. Knowledge of the serotype can provide useful guidance to a physician in determining a course of treatment of the disease in the subject. For example, the appropriately identified immune globulin having a sufficient titer may be administered to immunocompromised patients. Furthermore, an antiviral drug such as Pleconaril (Viropharma) may differ in its relative efficacy against different serotypes. Additionally, an understanding of the geographic and chronological development of an enterovirus infection in a population can influence preventive measures among the members of the population to minimize the spread of the disease. Furthermore, it is useful from a broader perspective to track the incidence and distribution of an enterovirus disease from an epidemiological point of view. In earlier practice, it was to found that the various serotypes could be grown in different cell culture hosts, and in different animal model hosts. In the animal hosts, furthermore, different symptomology also provided typing information. These classical assays provide ways of distinguishing the serotypes. Nevertheless, some enterovirus serotypes, especially in the coxsackievims A group, do not grow in cell culture. It has been observed that 25% to 35% of patient specimens are not identified by cell culture for a variety of reasons (Rotbart, 1995). Furthermore, such culturing and classification procedures are costly, time-consuming, subject to experimental variation, and not amenable to repetitive or extensive application in the field.

The serotypes of non-polio enteroviruses have been identified during the past several decades using classical immunological neutralization assays based on a panel of specific antibodies. Application of such a determination to a clinical sample is generally impractical and inconvenient. Although a number of neutralization sites have been localized to the VP1 protein of enteroviral particles, the exact identity of the epitopes responsible for serotype specificity remain unknown; VP2 and VP3 may also contain specific neutralizing epitopes. Serotyping has generally been carried out using intersecting pools of antisera, the Lim and Benyesh-Melnick (LBM) pools, which were originally defined in 1960 (Lim et al., J. Immunol. 84:309–317 (1960)). The antiserum pools currently distributed by the World Health Organization cover 42 serotypes in 8 pools (Melnick et al., Bull. WHO 48:263–268 (1973)). Analysis of the neutralization pattern affords an identification of serotype. (See Rotbart, 1995). Clearly, this is a cumbersome and painstaking process. Additionally, the supply of the antisera is limited or difficult to maintain. Problems in serotyping more recent isolates have been ascribed to pronounced intratypic antigenic variation (Meinick, Enteroviruses: polioviruses, coxsackie viruses, echoviruses, and newer enteroviruses. In Fields Virology (Fields et al., (Eds.) 3rd Ed., Lippincott-Raven Publishers, Philadelphia, 1996, pp. 655–712; Melnick et al., Bull. W.H.O. 63:453–550 (1985); Wigand et al., Arch. Ges. Virusforsch. 12:29–41 (1962); Wenner et al., Am J. Epidemiol. 85:240–249 (1967); Duncan, Arch. Ges. Virusforsch. 25:93–104 (1968)). This has been explained by pointing out that enteroviruses, being RNA viruses, undergo spontaneous mutation at a very high rate. This can lead to antigen drift, with the potential of producing antigenic variants such that a neutralization assay would produce a false negative result. For example, escape mutants in picornaviruses are discussed in detail in Mateu (Virus Res. 38:1–24 (1995)). For all these reasons there is a need to supplant neutralization assays for serotyping non-polio enteroviruses.

More recently assays based on nucleic acid detection have been developed. Probe hybridization assays directed either to RNA or to cDNA have been used to detect non-polio enteroviruses (Rotbart et al., Mol. Cell. Probes 2:65–73 (1988); Rotbart, J. Clin. Microbiol. 28:438–442 (1990); Chapman et al., J. Clin. Microbiol. 28: 843–850 (1990); Hyypia et al., J. Gen. Virol. 70:3261–3268 (1989); Olive et al. J. Gen. Virol. 71:2141–2147 (1990); Gilmaker et al., J. Med. Virol. 38:54–61 (1992); Yang et al., Virus Res. 24:277–296 (1992); Zoll et al., J. Clin. Microbiol. 30:160–165 (1992); Muir et al., J. Clin. Micro. 31:31–38 (1993); Drebot et al., J. Med. Virol. 44:340–347 (1994); Rotbart et al., J. Clin. Microbiol. 32:2590–2592 (1994)). In the absence of nucleic acid sequence information for the non-polio enteroviruses, most of these probes have targeted the highly conserved 5' non-coding region of the viral genomes. Additionally, RNA probes directed to the VP1 capsid gene have been used on a limited basis to identify some of the CBs and a few closely related CAs (Cova et al., J. Med. Virol. 24:11–18 (1988); Alksnis et al., Mol. Cell. Probes 3:103–108 (1989); Petitjean et al., J. Clin. Microbiol. 28:307–311 (1990)). More recently, oligonucleotides having sequences based on the VP4-VP2 junction have been applied as diagnostic and epidemiologic tools (Drebot et al., J. Med. Virol. 44:340–347 (1994); Arola et al., J. Clin. Microbiol. 34:313–318 (1996); Kim et al., Arch. Virol. 142:853–860 (1997); Oberste et al., Virus Res. 58:35–43 (1998)). The sequences in these regions, however, do not always correlate with serotype (Kopecka et al., Virus Res. 38:125–136 (1995); Arola et at., J. Clin. Microbiol. 34:313–318 (1996)). Furthermore, sequences of only certain pritotpyes prototypes were available with which to compare and classify clinical samples (Arola et al., (1996)). A generic probe-based assay for nucleic acids in the presence of chaotropic agents is described in U.S. Pat. No. 5,726,012. An assay for a target nucleic acid sequence wherein two separate probes are hybridized to the same strand of a nucleic acid, and then joined, for example by a polymerase activity, is disclosed in U.S. Pat. No. 5,516,641.

Reverse transcription (RT) coupled with the polymerase chain reaction (PCR) (RT-PCR) has been developed using enterovirus universal primers or broadly selective primers. Such primers are intended to amplify nucleotide regions from a large number of enterovirus serotypes in one diagnosis. One set of primers (Rotbart, J. Clin. Microbiol. 28:438–442 (1990)) has been reported to amplify 60 of the 66 serotypes tested. (Among the nonreactive serotypes, two are a typical enteroviruses and may be reclassified.) A comparison of sequence identities of the various sets of universal primers with serotype sequences is given in Rotbart et al. (1995). Many of the universal primer sets are designed to amplify regions of the 5' untranslated region of the genome (see, for example, Drebot et al. (1994); Diedrich et al., J. Med. Virol. 46:148–152 (1995); Arolaet al. (1996); Bailly et al., Virology 215:83–96 (1996); and U.S. Pat. No. 5,075,212 to Rotbart). A comparison of base sequences in coxsackievirus B5 was reported for isolates from three different outbreaks of disease, based on amplicons obtained using primers in the VP1/2A region of the genome (Kopecka et al., (1995)). Variations in sequence occurred even within the same outbreak, and somewhat greater variations were found among isolates from the different outbreaks, and between serotypes. International application WO 98/14611 discloses degenerate primers directed to the VP1 gene, which, when used in certain defined pairs, provide PCR amplification of enterovirus nucleic acids. Use of the specific primer pairs permits ascertaining whether a sample belongs to an enterovirus serotype, or to a small group of cognate serotypes, based on correlation of the pattern of the presence or absence of an amplicon with priming by the various primer pairs. This method does not rely on obtaining nucleotide sequences for accomplishing the serotyping.

Oberste et al. developed a database of homologous sequences for a portion of the VP2 gene of all 66 human enterovirus serotypes (Virus Res. 58:3545 (1998a)). They found that the sequences of many antigenic variants failed to cluster with their respective prototype strains as determined by serotyping. This finding suggested that the portion of VP2 examined may not prove to be useful for consistent molecular inference of serotype.

According to Holland et al. (J. Clin. Microbiol. 36:1588–1594 (1998)) neither cell culture growth, nor PCR can successfully type enterovirus infections. They report an alternative typing protocol based on polyacrylamide gel electrophoretic fingerprinting of whole virus radiolabeled proteins. However, the database of viral protein profiles contains data for less than one-third of the known EV serotypes. Therefore its general applicability remains unknown.

In the case of poliovirus, U.S. Pat. Nos. 5,585,477 and 5,691,134 to Kilpatrick disclose methods and oligonucleotide primers that are specific and sensitive for detecting all genotypes of poliovirus, as well as primers that are specific and sensitive for distinguishing the three serotypes of poliovirus, and methods for detecting poliovirus and/or distinguishing among the serotypes based on the use of the disclosed primers. Additionally WO 98/14611 discloses an extensive set of degenerate oligonucleotide primers for use in detecting the presence or absence of a non-polio enterovirus in a sample and to identify non-polio enterovirus serotypes. The primers are combined in pairs that detect various groupings of serotypes, and several amplification procedures are carried out in order to detect the presence of or absence of an amplicon in each case. A pooled grid of the results provides information useful in typing a non-polio enterovirus in a sample.

In summary, immunological methods for serotyping enteroviral infections are cumbersome and time consuming. They rely on an antigen-antibody reaction between antiserum pools established more than two decades ago, and whose supply may become limited. As explained, for example in Mateu (1995), antigen drift among RNA viruses such as the enteroviruses leads to a high probability that escape mutants will arise, and thereby escape not only serotyping, but perhaps detection as well. A second classical approach, cell culture coupled with whole animal host growth and use of antisera for typing, is extremely cumbersome, expensive, and labor-intensive. Modern molecular biological methods similarly have important deficiencies as currently implemented. Probe assays generally tend to lack sensitivity. Furthermore, a probe directed to a conserved region, such as the 5' non-coding region of the non-polio enteroviruses, lacks specificity, and so cannot be readily applied in typing a viral infection. RT-PCR has been implemented as a generic enteroviral diagnostic assay. In general, these assays fail to implement serotype-specific detection, so that typing is not currently available using RT-PCR. Holland et al. (1998) state that all typing methods in use or then currently under development are limited by virtue of the large number of different enteroviral serotypes, and as a consequence, the need for virus-specific reagents that would discriminate among them.

For these reasons, there remains a need for a typing procedure that avoids the necessity of infecting live animals, animal tissue homogenates, or cell cultures. There further remains a need to implement a nucleic acid-based enteroviral typing procedure that optimizes the specificity required for a typing protocol. There additionally persists a need for a typing procedure that avoids a requirement for a plethora of reagents directed toward the specificity of the various serotypes. There still further remains the need for an enteroviral typing procedure that does not require extended periods of time or complicated procedures to carry out. Thus, there remains a need for an operationally elegant and efficient typing procedure that utilizes the specificity that resides, for example, in the VP1 region. The present invention recognizes these needs, and addresses them.

SUMMARY OF THE INVENTION

As noted above, the determinants of serotype identity are understood to reside primarily in VP1. This amino acid sequence specificity should be reflected in the corresponding VP1 gene sequences. The present invention discloses a method, based on reverse transcription and amplification of a characteristic enteroviral nucleic acid segment, for detecting the presence of an enterovirus in a clinical sample. The method includes the steps of (i) obtaining a clinical sample from a subject;

(ii) purifying RNA contained in the sample;

(iii) reverse transcribing the RNA with primers effective to reverse transcribe enteroviral RNA to provide a cDNA;

(iv) contacting at least a portion of the cDNA with (a) a composition that promotes amplification of a nucleic acid and (b) an oligonucleotide mixture wherein the mixture comprises at least one oligonucleotide that hybridizes to a highly conserved sequence of the sense strand of an enterovirus nucleic acid and at least one oligonucleotide that hybridizes to a highly conserved sequence of the antisense strand of an enterovirus nucleic acid, thereby providing an amplification mixture, such that, upon hybridizing, the oligonucleotides direct amplification of at least a portion of the nucleotide sequence of the VP1 gene of the enterovirus genome;

(v) carrying out an amplification procedure on the amplification mixture, such that, if an enterovirus is present in the sample, an enterovirus amplicon is produced whose sequence includes a nucleotide sequence of at least a portion of the VP1 region of the enterovirus genome; and (vi) detecting whether the amplicon is present.

The presence of the amplicon, of course, indicates that an enterovirus is present in the sample.

In important embodiments of the method, the highly conserved sequences occur within the VP1 gene or within about 100 nucleotides from a terminus of the VP1 gene. Advantageously, at least one oligonucleotide of the mixture includes, at the 3' end thereof, a sequence that hybridizes to a sequence encoding the amino acid motif given by the sequences of either SEQ ID NO:80 or SEQ ID NO:81, and at least one oligonucleotide includes, at the 3' end thereof, a sequence that hybridizes to a sequence encoding a motif given by SEQ ID NO:82. Still more advantageously, the oligonucleotide mixture includes an oligonucleotide whose sequence contains, at the 3' end thereof, the sequence given by SEQ ID NO:3, and at least one oligonucleotide whose sequence contains, at the 3' end thereof, the sequence given by SEQ ID NO:4, or an oligonucleotide whose sequence contains, at the 3' end thereof, the sequence given by SEQ ID NO:9. In a highly advantageous embodiment, the sequences of these three oligonucleotides are given respectively by SEQ ID NO:3, SEQ ID NO:4, and SEQ ID NO:9.

In a further important embodiment of the method of detection, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85. In a further important embodiment, the oligonucleotide mixture contains an oligonucleotide whose sequence includes, at the 3' end thereof, the sequence given by SEQ ID NO:22, and at least one oligonucleotide chosen from among an oligonucleotide whose sequence includes, at the 3' end thereof, the sequence given by SEQ ID NO:19, an oligonucleotide whose sequence includes, at the 3' end thereof, the sequence given by SEQ ID NO:20, and an oligonucleotide whose sequence includes, at the 3' end thereof, the sequence given by SEQ ID NO:21. In a still more important embodiment, the oligonucleotide mixture contains an oligonucleotide whose sequence is given by SEQ ID NO:22, and at least one oligonucleotide chosen from among oligonucleotides whose sequences are given by SEQ ID NOs:19, 20, and 21.

In further significant embodiments of the method, the amplification procedure includes a polymerase chain reaction, and the sample is obtained from among whole blood or a fraction thereof, a bronchial wash, cerobrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In still other significant embodiments, the detection is carried out by a procedure chosen from among gel electrophoresis and visualization of amplicons contained in a resulting gel, capillary electrophoresis and detection of the emerging amplicon, probing for the presence of the amplicon using a labeled probe, and labeling a PCR primer employed in the method and detecting the label.

The invention additionally discloses a method for typing an enterovirus in a clinical sample that includes the steps of (i) obtaining a clinical sample from a subject;

(ii) purifying RNA contained in the sample;

(iii) reverse transcribing the RNA with primers effective to reverse transcribe enteroviral RNA to provide a cDNA;
(iv) contacting at least a portion of the cDNA with
   (a) a composition that promotes amplification of a nucleic acid and
   (b) an oligonucleotide mixture wherein the mixture comprises at least one oligonucleotide that hybridizes to a highly conserved sequence of the sense strand of an enterovirus nucleic acid and at least one oligonucleotide that hybridizes to a highly conserved sequence of the antisense strand of an enterovirus nucleic acid, thereby providing an amplification mixture, such that, upon hybridizing, the oligonucleotides direct amplification of at least a portion of the nucleotide sequence of the VP1 gene of the enterovirus genome;
(v) carrying out an amplification procedure on the amplification mixture, such that, if an enterovirus is present in the sample, an enterovirus sample amplicon is produced whose sequence includes a nucleotide sequence of at least a portion of the VP1 region of the enterovirus genome;
(vi) determining that the sample amplicon is present;
(vii) determining at least a partial nucleotide sequence of the sample amplicon;
(viii) providing a database consisting of prototypical nucleotide sequences, wherein each prototypical sequence is the sequence of a standard amplicon obtained from a member of a set of prototypical enterovirus serotypes by carrying out the procedure of steps (ii) through (v) on each prototypical enterovirus serotype, wherein each prototypical sequence comprises at least a portion of the sequence of the VP1 gene, and wherein the sequence of each prototypical VP1 gene is different from the sequence of every other prototypical VP1 gene in the database;
(ix) comparing the sequence of the sample amplicon with each prototypical sequence in the database; and
(x) identifying the prototypical sequence that has the highest extent of identity to the sequence of the sample amplicon, thereby providing an identified serotype;
wherein the type of the sample is the serotype of the identified serotype.

In important embodiments of this method, the highly conserved sequences occur within the VP1 gene or within about 100 nucleotides from a terminus of the VP1 gene. More importantly, at least one oligonucleotide of the mixture includes, at the 3' end thereof, a sequence that hybridizes to a sequence encoding the amino acid motif given by the sequences of either SEQ ID NO:80 or SEQ ID NO:81, and at least 0.25 one oligonucleotide includes, at the 3' end thereof, a sequence that hybridizes to a sequence encoding a motif given by SEQ ID NO:82. In significant embodiments of the method, the oligonucleotide mixture includes an oligonucleotide whose sequence contains, at the 3' end thereof, the sequence given by SEQ ID NO:3, at least one oligonucleotide whose sequence contains, at the 3' end thereof, the sequence given by SEQ ID NO:4 or an oligonucleotide whose sequence contains, at the 3' end thereof, the sequence given by SEQ ID NO:9. In a highly advantageous embodiment, the sequences of the oligonucleotides are given by SEQ ID NO:3, SEQ ID NO:4, and SEQ ID NO:9.

In an additional important embodiment, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85. In a further important embodiment, the oligonucleotide mixture contains an oligonucleotide whose sequence includes, at the 3' end thereof, the sequence given by SEQ ID NO:22, and at least one oligonucleotide chosen from among an oligonucleotide whose sequence includes, at the 3' end thereof, the sequence given by SEQ ID NO:19, an oligonucleotide whose sequence includes, at the 3' end thereof, the sequence given by SEQ ID NO:20, and an oligonucleotide whose sequence includes, at the 3' end thereof, the sequence given by SEQ ID NO:21. In a still more important embodiment, the oligonucleotide mixture contains an oligonucleotide whose sequence is given by SEQ ID NO:22, and at least one oligonucleotide chosen from among oligonucleotides whose sequences are given by SEQ ID NOs:19, 20, and 21.

In a further important aspect, the amplification procedure includes a polymerase chain reaction, and the resulting sample amplicon encompasses at least a portion of the nucleotide sequence for the VP1 gene of an enterovirus. The method furthermore importantly provides that the set of prototypical enterovirus serotypes comprises serotypes of coxsackie A viruses, coxsackie B viruses, echoviruses, and numbered enteroviruses. In advantageous aspects of the method, comparing the sequence of the sample amplicon with each sequence in the database employs a sequence alignment and comparison algorithm.

In further important aspects of the method, the sample is chosen from among whole blood or a fraction thereof, a bronchial wash, cerobrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal.

The present invention further provides an oligonucleotide containing, at the 3' end thereof, a sequence that hybridizes to a nucleotide sequence encoding an amino acid motif chosen from among the sequences given by SEQ ID NO:80, SEQ ID NO:81, SEQ ID NO:82, SEQ ID NO:83, SEQ ID NO:84, SEQ ID NO:85, and SEQ ID NO:86, or an oligonucleotide complementary to any of these oligonucleotides. In an advantageous embodiment, the complete sequence of the oligonucleotide is a sequence that hybridizes to a sequence encoding a motif whose sequence is chosen from among SEQ ID NO:80, SEQ ID NO:81, SEQ ID NO:82, SEQ ID NO:83, SEQ ID NO:84, SEQ ID NO:85, and SEQ ID NO:86, or is an oligonucleotide complementary to any of them.

In particularly important embodiments, such an oligonucleotide is one whose sequence contains, at the 3' end thereof, a sequence chosen from among the sequences given by SEQ ID NO:3, SEQ ID NO:4, SEQ ID NO:9, SEQ ID NO:19, SEQ ID NO:20, SEQ ID NO:21, and SEQ ID NO:22, or an oligonucleotide whose sequence is complementary to any of these oligonucleotides. In still more important embodiments, the sequence of the oligonucleotide consists of a sequence chosen from among SEQ ID NO:3, SEQ ID NO:4, SEQ ID NO:9, SEQ ID NO:19, SEQ ID NO:20, SEQ ID NO:21, and SEQ ID NO:22, or an oligonucleotide that is complementary to any of them.

The present invention further discloses a mixture of oligonucleotides including at least two oligonucleotides, wherein at least one of the oligonucleotides hybridizes to a sense strand of a double stranded nucleic acid and at least one of the oligonucleotides hybridizes to an antisense strand of the nucleic acid. The nucleic acid to which the oligonucleotides hybridize encodes the VP1 gene of an enterovirus, and the oligonucleotides hybridize to sequences that are highly conserved among the group of enteroviruses. The oligonucleotides, when hybridized to the nucleic acid, are bound in the correct orientation on their respective strands to direct the synthesis of an amplicon encoding at least a portion of the VP1 protein of enteroviruses when they are employed in an amplification procedure using the nucleic acid.

In important embodiments of the mixture, each oligonucleotide includes, at the 3' end thereof, a sequence that hybridizes to the nucleic acid. In still more important embodiments, the highly conserved sequences occur within the VP1 gene or within about 100 nucleotides from a terminus of the VP1 gene. Advantageously, at least one oligonucleotide includes, at the 3' end thereof, a sequence that hybridizes to a sequence encoding the amino acid motif given by the sequences of either SEQ ID to NO:80 or SEQ ID NO:81, and at least one oligonucleotide includes, at the 3' end thereof, a sequence that hybridizes to a sequence encoding an amino acid motif given by SEQ ID NO:82. Still more advantageously, the mixture includes an oligonucleotide whose sequence contains, at the 3' end thereof, the sequence given by SEQ ID NO:3, an oligonucleotide whose sequence contains, at the 3' end thereof, the sequence given by SEQ ID NO:4, and an oligonucleotide whose sequence contains, at the 3' end thereof, the sequence given by SEQ ID NO:9. In a highly advantageous embodiment, the sequences of the oligonucleotides are given by SEQ ID NO:3, SEQ ID NO:4, and SEQ ID NO:9.

In an important embodiment, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85.

In additional significant embodiments, the oligonucleotide mixture includes an oligonucleotide whose sequence contains, at the 3' end thereof, the sequence given by SEQ ID NO:22, and at least one oligonucleotide chosen from among an oligonucleotide whose sequence contains, at the 3' end thereof, the sequence given by SEQ ID NO:19, an oligonucleotide whose sequence contains, at the 3' end thereof, the sequence given by SEQ ID NO:20, and an oligonucleotide whose sequence contains, at the 3' end thereof, the sequence given by SEQ ID NO:21. In a still more significant embodiment, the oligonucleotide mixture includes an oligonucleotide whose sequence is given by SEQ ID NO:22, and at least one oligonucleotide chosen from among an oligonucleotide whose sequence is given by SEQ ID NO:19, an oligonucleotide whose sequence is given by SEQ ID NO:20, and an oligonucleotide whose sequence is given by SEQ ID NO:21.

The present invention additionally provides a kit for use in conducting the typing method that includes a mixture of oligonucleotides, the mixture containing an oligonucleotide whose sequence contains, at the 3' end thereof, the sequence given by SEQ ID NO:3, an oligonucleotide whose sequence contains, at the 3' end thereof, the sequence given by SEQ ID NO:4, and an oligonucleotide whose sequence contains, at the 3' end thereof, the sequence given by SEQ ID NO:9. In important embodiments of the kit, the oligonucleotide sequences are given by SEQ ID NO:3, SEQ ID NO:4, and SEQ ID NO:9.

In additional significant embodiments, the kit includes an oligonucleotide whose sequence contains, at the 3' end thereof, the sequence given by SEQ ID NO:22, and at least one oligonucleotide chosen from among an oligonucleotide whose sequence contains, at the 3' end thereof, the sequence given by SEQ ID NO:19, an oligonucleotide whose sequence contains, at the 3' end thereof, the sequence given by SEQ ID NO:20, and an oligonucleotide whose sequence contains, at the 3' end thereof, the sequence given by SEQ ID NO:21. In a still more significant embodiment, the oligonucleotide mixture includes an oligonucleotide whose sequence is given by SEQ ID NO:22, and at least one oligonucleotide chosen from among an oligonucleotide whose sequence is given by SEQ ID NO:19, an oligonucleotide whose sequence is given by SEQ ID NO:20, and an oligonucleotide whose sequence is given by SEQ ID NO:21.

BRIEF DESCRIPTION OF THE DRAWINGS

FIG. 1 is a schematic diagram of the non-polio enterovirus genome.

FIG. 2 illustrates RT-PCR amplification of all enterovirus prototype strains using primer pairs given by SEQ ID NOs:3 and 4, and by SEQ ID NOs: 3 and 9. PCR products were resolved by 1% agarose gel electrophoresis and visualized by ethidium bromide staining and UV transillumination. Panel A: Coxsackie A viruses, Coxsackie B viruses, and polioviruses amplified with primer pair given by SEQ ID NOs:3 and 4; Panel B: Coxsackie A viruses, Coxsackie B viruses, and polioviruses amplified with primer pair given by SEQ ID NOs: 3 and 9; Panel C: Echoviruses and numbered enteroviruses amplified with primer pair given by SEQ ID NOs: 3 and 4; Panel D: Echoviruses and numbered enteroviruses simplified with primer pair given by SEQ ID NOs: 3 and 9.

DETAILED DESCRIPTION OF THE INVENTION

The present invention advantageously provides methods for serotyping enteroviruses obtained from clinical samples. The methods are easily extended to human poliovirus, human picornaviruses such as human rhinovirus, and non-human picornaviruses such as bovine enterovirus and simian picornavirus. The procedures are easily and rapidly implemented using common laboratory procedures and instrumentation. They avoid the need for cumbersome, time-consuming and resource-intensive methods such as cell culture and/or host animal infection. They furthermore avoid reliance on prototypical antiserum pools which may fail to identify an enterovirus in a contemporary clinical sample because of antigen drift and escape from immunological reactivity. The methods of the present invention further advantageously permit identifying a serotype as being the most probable serotype even in the case of antigen drift, since nucleotide sequences are matched to provide a most probable serotype match, or, failing a unique match, a set of most probable serotype matches, even in the absence of a high extent of identity.

As used herein, the non-polio enteroviruses refer to the species/subgroups and serotypes, shown in Table 1, that are known in the field at the present time.

TABLE 1

Non-polio Enterovirus Species/Subgroups and Serotypes.

| Species/Subgroup | Serotypes[a] |
| --- | --- |
| Coxsackievirus A | CA1 to CA2, CA24 |
| Coxsackievirus B | CB1–CB6 |
| Echovirus | E1–E7, E9, E11–E27, E29– |
| Enterovirus (Numbered) | EV68–EV71 |

[a]Serotypes CA-23, E-10, E-28, and EV-72 have been reclassified (Miller, Clin. Infect. Dis. 16:612–613 (1993)). E-8 has been reclassified (Committee on the Enteroviruses, Virology 16:501–504 (1962); Harris et al., J. Infect. Dis. 127:63–68 (1973)).

As used herein, a "clinical sample" or a "clinical isolate" relates to any sample obtained from a subject for use in carrying out the procedures of the present invention. In a principal aspect, the subject is suspected of suffering from a disease or syndrome that is at least partially caused by an enterovirus. The subject may also be an asymptomatic individual considered to be at risk of enterovirus infection. The sample may be a cellular sample such as a tissue sample, for example, a sample of lung tissue obtained as a biopsy or post-mortem, a fluid sample such as blood, saliva, sputum, urine, cerebrospinal fluid, or a swabbed sample obtained by swabbing a mucus membrane surface such as a nasal surface, a pharyngeal surface, a buccal surface, and the like, or it may be obtained from an excretion such as feces, or it may be obtained from other bodily tissues or body fluids commonly used in clinical diagnostic testing. In its broadest sense, a "clinical sample" or a "clinical isolate" as used herein is obtained from a human subject or a non-human mammalian subject, and is directed to suspected symptoms or syndromes ascribable to a picornavirus or enterovirus infection.

As used herein, purification of RNA as a step in the methods of the invention, in particular, as a step leading up to a RT-PCR procedure, relates to releasing RNA from a latent or inaccessible form in a virion or a cell and allowing the RNA to become freely available. In such a state, it is suitable for effective amplification by reverse transcription and use of the polymerase chain reaction. Releasing RNA may include steps that achieve the disruption of virions containing viral RNA, as well as disruption of cells that may harbor such virions. Purification of RNA is generally carried out under conditions that rigorously and effectively exclude or inhibit any ribonuclease activity that may be present. Additionally, purification of RNA may include steps that achieve at least a partial separation of the RNA dissolved in an aqueous medium from other cellular or viral components, wherein such components may be either particulate or dissolved As used herein, "reverse transcription" or "RT" relates to a procedure catalyzed by an enzyme activity, reverse transcriptase, that synthesizes a cDNA from a single stranded RNA molecule, with the use of oligonucleotide primers having free 3'-hydroxyl groups. As used herein the term "polymerase chain reaction" or "PCR" relates to a procedure whereby a limited segment of a nucleic acid molecule, which frequently is a desired or targeted segment, is amplified repetitively to produce a large amount of DNA molecules which consist only of that segment. The procedure depends on repetition of a large number of priming and transcription cycles. In each cycle, two oligonucleotide primers bind to the segment, and define the limits of the segment. A primer-dependent DNA polymerase then transcribes, or replicates, the strands to which the primers have bound. Thus, in each cycle, the number of DNA duplexes is doubled.

As used herein the term "primer" or "oligonucleotide primer" relates to an oligonucleotide having a specific or desired nucleotide sequence which is complementary to a particular sequence on one of the strands of a DNA duplex. When the primer is caused to hybridize to the specific sequence in a DNA duplex to which it is complementary, it may serve as the priming position, or the initiation position, for the action of a primer-dependent DNA polymerase activity. The primer, once hybridized, acts to define the 5' end of the operation of the transcription activity of the polymerase on the duplex. Commonly in PCR, a specific pair of primers is employed, wherein one of the primers hybridizes to one of the strands and the second primer hybridizes to the complementary strand. The primers hybridize in such an orientation that transcription, which proceeds in the direction from 5'- to 3'-, is in the direction leading from each primer toward the site of hybridization of the other primer. After several rounds of hybridization and transcription the amplified DNA produced is a segment having a defined length whose ends are defined by the sites to which the primers hybridize.

The oligonucleotide primers of the invention are intended for use in a RT-PCR-based amplification of a target segment of a nucleic acid from an enterovirus. Both RT and PCR rely on the action of a DNA polymerase activity to extend the new DNA strands beyond the 3' termini of the primers. Since DNA polymerases extend a chain in the direction from 5' to 3', an oligonucleotide that contains sequences in addition to those nucleotides that hybridize to the target nucleic acid and serve as the primer must have the primer sequence at the 3' end of the oligonucleotide. Additionally, any complements of the oligonucleotides contemplated in the invention must have the sequence complementary to the hybridizing sequence at the 5' end of the molecule such that action of a DNA polymerase will generate a primer oligonucleotide having its complementary sequence at its 3' end.

As used herein the terms "specific to" or "specific for" a target sequence, in relation to a nucleic acid sequence such as an oligonucleotide sequence, relate to a nucleotide sequence that hybridizes, under conditions used in given experimental circumstances, to the target but does not hybridize under those circumstances to sequences that are not target sequences. Nucleotide sequences that are specific for a particular target, such as the enteroviral target sequences that are included in the subject matter of the present invention, are those that include bases all of which are complementary to the corresponding base on the target.

Further as used herein, "specificity" of a nucleic acid sequence for a target sequence also encompasses nucleic acids and oligonucleotides having a small number of nucleotides which may not be complementary to the corresponding nucleotides of the target sequence. Such sequences are still "specific" for the target sequence, as used herein, as long as the extent of deviation from complementarity remains functionally of no consequence. In particular, such a sequence is "specific" for the target sequence as long as it hybridizes effectively to the target sequence but does not hybridize to any sequence that is not a target sequence, under the conditions used in given experimental circumstances.

As used herein, an "amplicon" relates to a double stranded nucleic acid segment having a defined size and sequence that results from an amplification procedure, such as a PCR procedure. The size of the amplicon is governed by the sites on the two strands of a nucleic acid duplex to which the primers bind. As explained in U.S. Pat. No. 4,683,195, that segment of the product nucleic acid becomes the prevalent product of the amplification procedure after a small number of cycles of amplification.

As used herein, the terms "prototype", "prototypical sequence", "prototypical amplicon", and "prototypical enterovirus serotype" relate, insofar as the root "prototype" occurs in each of these terms, to the enterovirus serotypes which were used to establish the classical antisera defined against each serotype. These were originally obtained several decades ago, as described in Lim et al. (1960) and subsequently, for example, in Meinick et al. (Bull. Wld. Hlth. Org. 48:2163–268 (1973)), and Melnick et al. (1985). As used herein, these terms are distinguished from variants of a given prototypical serotype, wherein a variant represents a phenotype resulting from antigenic drift, such as a phenotype that may represent an escape mutant. Such variants may occur in the field among contemporary clinical isolates of enteroviruses.

As used herein, a "motif" relates to a short sequence of amino acid residues that is highly conserved among a family of proteins from different species or variants.

Developing a Database of Nucleotide Sequences Characteristic of the Prototypical Enteroviruses. In order to practice the methods of the present invention, a database of sequences characteristic of the prototypical enteroviruses is needed. In order to prepare such a database, a region of the enteroviral genome is selected that has within its nucleotide sequence sufficient variation among the different serotypes that the sequence from each serotype may be considered to be unique. In the present invention, the VP1 region of the viral RNA was identified as having the requisite sequence uniqueness from one serotype to another. Among the entries in Table 2, below, direct comparison of results based on VP1 versus those obtained with VP2 for the following variants of the respective serotypes provided evidence that VP1 affords the selectivity required for this invention, whereas VP2 does not. The variants are CA24v strain EH24/70, E4 stain Du Toit, E4 strain Shropshire, E6 stain Charles, E6' strain Cox, E6" strain Burgess, E8 strain Bryson, E9 strain Barty, E11' strain Silva, E30 strain Frater, E30 strain Giles, E30 strain PR-17, E34 strain DN-19, PV1 strain Sabin, PV2 strain Sabin, and PV3 strain Sabin. Once such a region is identified, the nucleotide sequences from this region are determined for each virus among the set of prototypical serotypes. The serotype prototypes of interest in the present invention are listed in Tables 1 and 2; Table 2 includes entries for additional enteroviruses and picornaviruses as well. The viruses may be obtained from publicly available deposits made at the American Type Culture Collection (Rockville, Md.).

TABLE 2

Enterovirus and Picornavirus VP1 Sequences Used in Establishing a Sequence Database

| Serotype | Strain | GenBank Accession Number | SEQ ID NO: |
|---|---|---|---|
| CA1 | Tompkins | AF081293 | 23 |
| CA2 | Fleetwood | L28146 (a) | |
| CA3 | Olson | AF081294 | 24 |
| CA4 | High Point | AF081295 | 25 |
| CA5 | Swartz | AF081296 | 26 |
| CA6 | Gdula | AF081297 | 27 |
| CA7 | AB-IV | AF061298 | 28 |
| CA8 | Donovan | AF081299 | 29 |

TABLE 2-continued

Enterovirus and Picornavirus VP1 Sequences Used in Establishing a Sequence Database

| Serotype | Strain | GenBank Accession Number | SEQ ID NO: |
|---|---|---|---|
| CA9 | Griggs | D00627 (b) | |
| CA10 | Kowalik | AF081300 | 30 |
| CA11 | Belgium[1] | AF081301 | 31 |
| CA12 | Texas-12 | AF081302 | 32 |
| CA13 | Flores | AF081303 | 33 |
| CA14 | G-14 | AF081304 | 34 |
| CA15 | G-9 | AF081305 | 35 |
| CA16 | G-10 | U05876 (c) | |
| CA17 | G-12 | AF081306 | 36 |
| CA18 | G-13 | AF081307 | 37 |
| CA19 | 8663 | AF081308 | 38 |
| CA20 | IH-35 | AF081309 | 39 |
| CA21 | Kuykendall | D00538 (d) | |
| CA22 | Chulman | AF081310 | 40 |
| CA24 | Joseph | AF081311 | 41 |
| CA24v | EH24/70 | D90457 (e) | |
| CB1 | Conn-5 | M16560 (f) | |
| CB2 | Ohio-1 | AF081312 | 42 |
| CB3 | Nancy | M16572 (g) | |
| CB4 | JVB | D00149 (h) | |
| CB5 | Faulkner | X67706 (i) | |
| CB6 | Schmitt | AF081313 | 43 |
| E1 | Farouk | AF081314 | 44 |
| E2 | Cornelis | AF081315 | 45 |
| E3 | Morrisey | AF081316 | 46 |
| E4 | Pesacek | AF081317 | 47 |
| E4 | Du Toit | AF081318 | 48 |
| E4 | Shropshire | AF081319 | 49 |
| E5 | Noyce | AF081320 | 50 |
| E6 | Charles | U16283 (j) | |
| E6 | D'Amori | AF081321 | 51 |
| E6' | Cox | AF081322 | 52 |
| E6" | Burgess | AF081323 | 53 |
| E7 | Wallace | AF081324 | 54 |
| E8 | Bryson | AF081325 | 55 |
| E9 | Hill | X84981 (k) | |
| E9 | Barty | X92886 (l) | |
| E11 | Gregory | X80059 (m) | |
| E11' | Silva | AF081326 | 56 |
| E12 | Travis | X79047 (n) | |
| E13 | Del Carmen | AF081327 | 57 |
| E14 | Tow | AF081328 | 58 |
| E15 | Cll96-51 | AF081329 | 59 |
| E16 | Harrington | X89545 (o) | |
| E17 | CHHE-29 | AF081330 | 60 |
| E18 | Metcalf | AF081331 | 61 |
| E19 | Burke | AF081332 | 62 |
| E20 | JV-1 | AF081333 | 63 |
| E21 | Farina | AF081334 | 64 |
| E22 | Harris | S45208 (o) | |
| E23 | Williamson | AF055846 (p) | |
| E24 | De Camp | AF081335 | 65 |
| E25 | JV-4 | AF081336 | 66 |
| E26 | Coronel | AF081337 | 67 |
| E27 | Bacon | AF081338 | 68 |
| E29 | JV-10 | AF081339 | 69 |
| E30 | Bastianni | AF081340 | 70 |
| E30 | Frater | AF081341 | 71 |
| E30 | Giles | AF081342 | 72 |
| E30 | PR-17 | AF081343 | 73 |
| E31 | Caldwell | AF081344 | 74 |
| E32 | PR-10 | AF081345 | 75 |
| E33 | Toluca-3 | AF081346 | 76 |
| E34a | DN-19 | AF081347 | 77 |
| EV68 | Fermon | AF081348 | 78 |
| EV69 | Toluca-1 | AF081349 | 79 |
| EV70 | J670/71 | D00820 (q) | |
| EV71 | Brcr | U22521 (r) | |
| PV1 | Mahoney | J02281 (s) | |
| PV1 | Sabin | V01150 (t) | |
| PV2 | Lansing | M12197 (u) | |
| PV2 | Sabin | X00595 (v) | |
| PV3 | Leon | K01392 (w) | |

TABLE 2-continued Enterovirus and Picornavirus VP1 Sequences Used in Establishing a Sequence Database

| Serotype | Strain | GenBank Accession Number | SEQ ID NO: |
|---|---|---|---|
| PV3 | Sabin | X00596 (v) | |
| BEV1 | VG-5-27 | D00214 (x) | |
| BEV2a | RM-2 | X79369 (y) | |
| BEV2b | PS-87 | X79368 (y) | |
| HRV3 | Unknown | U60874 | |
| PEV9 | UKG/410/73 | Y14459 (z) | |
| SVDV | H/376 | D00435 (h) | |
| HRV1b | Unknown | D00239 (dd) | |
| HRV2 | Unknown | X02316 (aa) | |
| HRV3 | Unknown | U60874 | |
| HRV14 | Unknown | KO2121, X01087 (bb) | |
| HRV16 | Unknown | L24917 (ee) | |
| HRV89 | 41467 Gallo | M16248 (ff) | |
| HAV | HM-175 | M14707 (cc) | |

Notes for Table 2:
PEV, porcine enterovirus; SVDV, swine vesicular disease virus; HRV, human rhinovirus; HAV, hepatitis A virus.
a) Pulli, T., et al., Virology 211:30–38 (1995).
b) Chang, K., et al., J. Gen. Virol. 70:3269–3280 (1989).
c) Poyry, T., et al., Virology 202:982–987 (1994).
d) Hughes, P.J., et al al. J. Gen. Virol. 70:2943–2952 (1989).
e) Supanaranond, K., et al., Virus. Genes 6:149–158 (1992).
f) Iizuka, N., et al. Virology 156:64–73 (1987).
g) Lindberg, A. M,, et al., Virology 156:50–63 (1987).
h) Jenkins, O., et al., J. Gen. Virol. 68:1835–1848 (1987).
i) Zhang, G,, et al., J. Gen. Virol. 74:845–853 (1993).
j) Harris, L.F., et al., J. Infect. Dis. 127:63–68 (1973).
k) Zimmermann, H., et al., Virus Res 39:311–319 (1995).
l) Zimmermann, H., et al., Virus Genes 12:149–154 (1996).
m) Dahllund, L., et al al., Virus Res. 35:215–223 (1995).
n) Kraus, W., et al. J. Virus 69:5853–5858 (1995).
o) Huttunen, P., et al., J. Gen. Virol. 77:715–725 (1996).
p) Oberste, M.S., et al., Virus. Res. 56:217–223 (1998).
q) Ryan, M.D., et al., J. Gen. Virol. 71:2291–2299 (1990).
r) Brown, B.A., et al., Virus. Res. 39:195–205 (1995).
s) Kitamura, N.B., et al., Nature 291:547–553 (1981); Racaniello, V.R., et al. Proc. Natl. Acad. Sci. USA 78:4887–4891 (1981).
t) Dorner, A.J., et al., J. Virol. 42:1017–1028 (1982); Emini, E. A., et al., J. Virol. 42:194–199 (1982); Nomoto, A., et al. Proc. Natl. Acad. Sci. USA 79:5793–5797 (1982).
u) La Monica, N., et al., J. Virol. 57:515–525 (1986).
v) Toyoda, H., et al. J. Mol. Biol. 174:561–585 (1984).
w) Stanway, G., et al. Proc. Natl. Acad. Sci. USA 81:1539–1543 (1984).
x) Earle, J. A., et al., J. Gen. Virol. 69:253–263 (1988).
y) McNally, R.M., et al al., Arch. Virol. 139:287–299 (1994).
z) Peng, J., et al., Unpublished data.
aa) Skern, T., et al., Nucl. Acids Res. 13:2117–2126 (1985).
bb) Callaghan, P.L., et al., Proc. Natl. Acad. Sci USA 82:732–736 (1985); Stenway, G., et al., Nucl. Acids Res. 12:7859–7875 (1984).
cc) Cohen, J.L., et al., S. Virol. 61:50–59 (1987).
dd) Hughes, P.J., et al., J. gen. VFirol. 69:49–58 (1988).
ee) Lee, W.M., et al., Virus Genes 9:177–181 (1995).
ff) Duechler, M., et al., Proc. Natl. Acad. Sci. USA 84:2605–2609 (1987).

The virus specimens are used to infect any enterovirus-susceptible cell line in culture, including, by way of non-limiting example, RD (human rhabdomyoscarcoma) cells, HLF (human embryonic lung fibroblast) cells, LLC-$M_2$ (monkey kidney) cells, or BGM (buffalo green monkey kidney) cells; alternatively, a tissue homogenate in tissue culture medium may be prepared from mouse brain after infection of the mouse with the virus. In the case of cell cultures, the culture supernatant is used. In the case of the brain homogenate, the whole homogenate, after growth of the virus, is used. Viral RNA is extracted from the growth media containing the enterovirus prototypes by any method that releases the RNA from the virion and/or the cell components and provides a purified preparation of the RNA. By way of nonlimiting example, the RNA may be extracted using guanidinium isothiocyanate, such as the single-step isolation by acid guanidinium thiocyanate-phenol-chloroform extraction of Chomczynski et al. (Anal. Biochem. 162:156–159 (1987)). Alternatively, the virion may be disrupted by a suitable detergent in the presence of proteases and/or inhibitors of ribonuclease activity. The RNA released from the virion is isolated or purified, using, for example, methods such as precipitation with an alcohol (e.g., ethyl alcohol or isopropyl alcohol) or banding in a suitable density gradient using an ultracentrifuge.

The purified viral RNA is then subjected to a reverse transcription to prepare a cognate cDNA that encompasses the region of the genome chosen for discriminating between serotypes (i.e., the region encoding VP1 ). An advantageous way of achieving this is to use a set of random oligonucleotide primers in the reverse transcription, such that certain of the primers in the set will hybridize to the RNA and yield one or more cDNA molecules from the virus encompassing the required serotype-specific nucleotide sequence. Alternatively, gene-specific primers based on a viral RNA-specific sequence from a suitable cDNA may be employed for reverse transcription. Subsequently, the cDNA is amplified using a suitable amplification protocol. By way of nonlimiting example, a polymerase chain reaction (PCR) protocol may be employed for this purpose. PCR is described in operational detail in, for example, "Molecular Cloning: A Laboratory Manual," 2nd ed., Sambrook, Fritsch and Maniatis, Cold Spring Harbor Laboratory, Cold Spring Harbor, N.Y., 1989; "Current Protocols in Molecular Biology," Ausubel et al., John Wiley and Sons, New York 1987 (updated quarterly); and "PCR Protocols: A Guide to Methods and Applications," Innis et al., Academic Press, San Diego, Calif. 1990; and in U.S. Pat. Nos. 4,683,195; 4,683,202; 4,965,188; 5,578,467; 5,545,522; and 5,624,833, all of which are incorporated herein by reference.

For the PCR of the cDNA to yield an amplicon containing a sequence from the VP1 region, primers such as those provided in Table 3 (SEQ ID NOs:1–22) may be employed. In Table 3, nucleotide sequence positions are given relative to the sequence of poliovirus1-Mahoney (Kitamura, N. B., et al. Nature 291:547–553 (1981); Racaniello, V. R., et al. Proc. Natl. Acad. Sci. USA 78:4887–4891 (1981)).

TABLE 3

Primers Used for PCR Amplification of the VP1 Region of Enteroviruses

| Primer | Sequence | Gene | Position | SEQ ID NO |
|---|---|---|---|---|
| 008 | GCRTGCAAGAYTTCTCWGT | VP3 | 2411–2430 | 1 |
| 009 | NGCNCCDGAPPTTGNTGSCC | 2A | 3409–3391 | 2 |
| 011 | GCICCIGAYTGITGICCRAA | 2A | 3408–3389 | 3 |
| 012 | ATGTAYGTICCICCIGGIGG | VP1 | 2951–2970 | 4 |
| 013 | GGIGCRTTICCYTGIGTCCA | VP1 | 3051–3032 | 5 |
| 019 | ACRTGICIIGTYTGCATIGT | VP1 | 2676–2857 | 6 |
| 035 | AWITTYTAYGAYGGITGG | VP1 | 3098–3115 | 7 |
| 036 | TAIAIIGTICCCATRTTRTT | VP1 | 3201–3182 | 8 |
| 040 | ATGTAYRTICCIMCIGGIGC | VP1 | 2951–2970 | 9 |
| 041 | GGIGGIGGRTCIGTJAKYTT | VP1 | 3054–3035 | 10 |
| 045 | GAIGARAAYCTIATIGARAC | VP1 | 2648–2667 | 11 |
| 048 | CCCATIAKRTCIATRTCCC | VP1 | 2820–2801 | 12 |
| 050 | GTRCTYACIAIIAGRTCYCT | 2A | 3513–3494 | 13 |
| 051 | TSAARYTGTGCAARGACAC | VP3 | 2429–2448 | 14 |
| 052 | STGYCCAGATTCAGTGT | VP3 | 2413–2430 | 15 |
| 053 | GGNACNCAYRTNATHTGGGA | VP3 | 2216–2235 | 16 |
| 054 | GCCITRTTITGRTGICCRAA | 2A | 3408–3389 | 17 |
| 055 | GGIACICAYRTIRTITGGGA | VP3 | 2216–2235 | 18 |
| 187 | ACIGCIGYIGARACIGGNCA | VP1 | 2612–2631 | 19 |
| 188 | ACIGCIGTIGARACIGGNG | VP1 | 2612–2630 | 20 |

TABLE 3-continued Primers Used for PCR Amplification of the VP1 Region of Enteroviruses

| Primer | Sequence | Gene | Position | SEQ ID NO |
|---|---|---|---|---|
| 189 | CARGCIGCGARACIGGNGC | VP1 | 2612–2631 | 21 |
| 222 | CICCIGGIGGIAYRWACAT | VP1 | 2969–2951 | 22 |

These primers were designed to amplify a broad range of cDNA fragments drawn from the set of enteroviruses (see Example 2). The primers of SEQ ID NOs:1–22 were designed based on information available regarding known sequences of non-polio enteroviruses, as well as sequences in the VP1 region obtained as part of the development of the present invention (see Example 1; see Table 2 for GenBank accession numbers of the sequences). Additional information used to design the primers of SEQ ID NOs:1–22, especially the primers of SEQ ID NOs:19–22, was obtained from known sequences of other members of the Picornaviridae family, as provided in Table 2.

The amplicons obtained from the PCR protocol applied to each prototype virus are sequenced to obtain the nucleotide sequence in each. Procedures that may be used for sequencing include the methods of Maxam and Gilbert (Meth. Enzymol. 65, 499–566 (1980)) and Sanger et al., (Proc. Natl. Acad. Sci. USA 74:5463–5467 (1977)) (see also Sambrook et al., (1989)). The method of Maxam and Gilbert involves random chemical degradation reactions carried out on a nucleic acid labeled at one end Each of four separate degradation reactions is specific for a different one of the four bases in the nucleic acid. The method of Sanger et al. involves use of a different 2',3'dideoxynucleotide chain terminator in each of four template-driven DNA polymerase reactions. The Sanger method is readily implemented in automated sequencing instruments, such as those of PE-Biosystems, Foster City, Calif. The VP1 sequences that were obtained with the above procedures were incorporated into the non-polio enterovirus database of the present invention (see Table 2).

Typing of Clinical Isolates Obtained in the Field. A clinical sample is obtained from a subject suspected of harboring an enterovirus. Any suitable clinical specimen may be used for this purpose. Commonly, and by way of nonlimiting example, such a sample may be whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, or tissue from an experimentally infected animal.

Viral RNA may be isolated from a clinical sample either directly or after inoculating a cell culture with the clinical sample and cultivating a larger virus population. Direct isolation is rapid but may result in low virus titer, whereas inoculation and cell culture will provide a higher titer but may take several days.

In order to obtain amplicons from viral RNA, the RNAs from the virus isolates are treated with a reverse transcriptase primer preparation that contains a random oligonucleotide RT primer, such as a library of random hexanucleotides. The resulting cDNA is amplified in a PCR procedure using a mixture of oligonucleotide primers that hybridize to motifs that are highly conserved throughout the enteroviruses, or more generally, motifs that are highly conserved among the picornaviruses. As used herein, the notion of hybridizing specifically to a highly conserved region encoding a highly conserved amino acid motif relates to identifying at least two nucleotide sequences in the viral genomes which display minimal variation across both the complete spectrum of prototypical enterovirus serotypes, as well as the variants that may be present in clinical samples at any given time. Thus, at least two relatively constant amino acid sequences, or motifs, encoded by these nucleotide sequences, occur phenotypically in all or most of the viruses of the enteroviral species and variants, and the corresponding coding sequences in the nucleic acid are likewise relatively constant across the prototypes and variants. Such conserved or invariant sequences, or motifs, are required in order that a single pair of oligonucleotide primers, or as small a set of such primers as is practical, suffices to prime the amplification of all or the maximum possible number of prototypical viruses and all or the maximum number of viral variants infecting the population at any given time.

In important embodiments of the invention, the primers used are a mixture of oligonucleotides whose use in a PCR amplification provides an amplicon encompassing most or all of the VP1 gene. By way of nonlimiting example, such a mixture may of include an oligonucleotide chosen from among an oligonucleotide whose sequence contains, at the 3 end thereof, the sequence given by SEQ ID NO:4, an oligonucleotide whose sequence contains, at the 3' end thereof, the sequence given by SEQ ID NO:9, and a mixture thereof, as well as an oligonucleotide whose sequence contains, at the 3' end thereof, the sequence given by SEQ ID NO:3 (see Table 3); in particularly important embodiments the oligonucleotides employed according to the above mixtures are primer 011 (SEQ ID NO:3), primer 012 (SEQ ID NO:4), and primer 040 (SEQ ID NO:9). The use of either or both of the primers (012, SEQ ID NO:4 and 040, SEQ ID NO:9) provides specific hybridization to target sequences in the 5' region of the VP1 gene of most or all of the non-polio enteroviruses. The third primer, 011 (SEQ ID NO:3), specifically hybridizes to a target sequence in the 2A region of most or all the non-polio enteroviruses. Each primer is disclosed in PCT application WO 98/14611, which is incorporated herein by reference.

More generally, primer sets that include a mixture of oligonucleotides that contain the sequences given by SEQ ID NO:19, SEQ ID NO:20, SEQ ID NO:21, or SEQ ID NO:22 may be employed in amplifying a broad range of picornaviruses. Specifically, oligonucleotides chosen from among an oligonucleotide whose sequence contains, at the 3' end thereof, the sequence given by SEQ ID NO:19, an oligonucleotide whose sequence contains, at the 3' end thereof, the sequence given by SEQ ID NO:20, an oligonucleotide whose sequence contains, at the 3' end thereof, the sequence given by SEQ ID NO:21, and mixtures thereof, may be combined with an oligonucleotide whose sequence contains, at the 3' end thereof, the sequence given by SEQ ID NO:22 (see Table 3) for use in the present method. Advantageously, the oligonucleotides included in the above mixtures are primer 187 (SEQ ID NO:19), primer 188 (SEQ ID NO:20), primer 189 (SEQ ID NO:21), and primer 222 (SEQ ID NO:22).

Using the mixtures of oligonucleotide primers set forth in the preceding paragraphs leads to preparation of the enteroviral PCR amplicons according to the method of this invention. The amplicons are then either detected or isolated for sequence analysis. They may be isolated by any of a variety of amplicon purification procedures that serve to provide a purified preparation of the amplicon. These include, by way of nonlimiting example, gel electrophoresis coupled with visualization using a fluorescent dye and extraction of the detected amplicon from the gel, and extraction from the amplification solution using an immobilized derivative of one or more of the PCR primers to bind a strand of the amplicon after it has been denatured. The purified amplicons may be sequenced using conventional sequencing techniques or procedures.

The nucleotide sequence obtained for the amplicon derived from a particular clinical sample of an enterovirus is then matched with the sequences in the database of prototypical sequences describing the known serotypes of enteroviruses. The sequence matching may be carried out by any suitable sequence matching algorithm designed to determine the extent of identity or similarity between a query sequence in its entirety and a standard or reference sequence. By way of nonlimiting example, such an algorithm may be that of Needleman and Wunsch (J. Mol. Biol. 48:443–453 (1970) implemented in the program Gap in the Wisconsin Sequence Analysis Package, version 9.1), and the like. Such algorithms provide a result that the query sequence most resembles a particular one, and (in most cases) only one, of the reference sequences drawn from the database. According to the present method, the serotype of the enterovirus in the clinical sample is the serotype of the sequence from the database identified as most closely resembling the sequence of the sample.

Numerous advantages result upon implementation of the present invention. Typing of an enterovirus in a clinical sample may be done avoiding the necessity of culturing the sample in a cell culture or in a whole animal host (e.g., mouse). Such procedures are cumbersome, labor-intensive and resource-intensive, and pose dangers of infection to the workers conducting the assay. The typing likewise avoids the necessity of conducting a standardized serotyping assay. Serotyping is labor-intensive, and requires the availability of the antiserum pools that are specific or selective for the various enterovirus serotypes. Furthermore, serotyping using these procedures is not very effective because numerous variants and escape mutants in field samples of enteroviruses avoid detection and provide, therefore, a false negative result. The present invention additionally avoids the disadvantages of known PCR amplification procedures employed with non-polio enteroviruses, which are largely based on the conserved 5' untranslated region of the non-polio enterovirus genome, and thereby lack a means for typing the samples found.

In contrast, the present invention provides the only PCR-based means for typing a clinical sample of an enterovirus available at the present time. The procedure is easy to carry out and provides an unambiguous, and accurate, typing of a clinical sample in a large fraction of test cases that were also typed by standard serotype pools. Typing of cases of enterovirus-caused diseases or syndromes permits an appropriate therapy to be chosen in suitable cases. Such therapy should lead to amelioration of the severity of the disease or syndrome and, hopefully, a complete recovery. Typing furthermore provides important public health and epidemiological information that could lead to protective and/or preventive measures being taken among a population at risk of contracting such a disease or syndrome.

The following examples are intended to illustrate the invention and not to limit it.

EXAMPLE 1

Establishing a Database of Sequences Corresponding to Standard Non-Polio Enterovirus Serotypes The viruses used for sequence analysis are listed in Table 2, above. The prototypical virus samples were obtained from the American Type Culture Collection. The viruses were propagated in RD cells, HLF cells, LLC-$MK_2$ cells, or primary monkey kidney cells using Eagle's MEM supplemented with 2% fetal bovine serum or by intracerebral inoculation of newborn mice (see Grandien, M., et al., "Enteroviruses and Reoviruses", in Diagnostic procedures for viral, rickettsial, and chlamydial infections, 6th Ed. (Schmidt, N. J., et al., eds.) 1989, Amer. Public Health Assoc., Washington, D.C., pp. 513–578). The isolation of the viral RNA, and the RT-PCR amplification was conducted as described by. Oberste et al. (Am. J. Trop. Med. Hyg. 58:4146 (1998b)). In summary, in this procedure, viral RNA was extracted from infected cell culture supernatants, or from 10% infected mouse brain homogenate with Trizol LS™ (Life Technologies, Inc., Gaithersburg, Md.), and cDNA was obtained by use of a set of random hexanucleotide primers (Boehringer Mannheim Biochemicals, Indianapolis, Ind.), and a SuperScript™ preamplification kit (Life Technologies, Inc.). Reverse transcription was performed in a solution containing 20 mM Tris chloride pH 8.3, 50 mM KCl, 2.5 mM $MgCl_2$, 0.1 M dithiothreitol, 0.5 mM each of dATP, dCTP, dGTP, and TTP, 0.8 $\mu$M random hexamer primer, 5 $\mu$L RNA, and 10 U SuperScript II™ reverse transcriptase (Life Technologies, Inc.). The reaction proceeded for 1 h at 42° C.

The resulting cDNAs were amplified by PCR using primers for VP3 and 2A shown in Table 3 (SEQ ID NOs:1–18), in a reaction containing 20 mm Tris chloride pH 8.3, 50 mM KCl, 2.5 mM $MgCl_2$, 0.2 mM each of dATP, dCTP, dGTP, and TTP, 1 $\mu$M sense-orientation primer, 1 $\mu$M antisense-orientation primer 1 $\mu$L cDNA from the reverse transcription step, above, and 1.25 U Thermus aquaticus DNA polymerase (Life Technologies, Inc.). The reaction was incubated at 94° C. for 3 min, then followed by 35 cycles of 94° C. for 30 s, 42° C. for 30 s, and 72° C. for 30 s, followed by incubation at 72° C. for 5 min. The specific primer pairs used differed from one virus to another in order to obtain satisfactory yields of the amplicons. For some viruses, VP1 was amplified as two overlapping fragments with internal VP1 primers as well as the VP3 and 2A primers. The PCR products were gel isolated and purified in preparation for sequencing with the QIAquick™ gel extraction kit (QIAGEN, Inc., Santa Clarita, Calif.), in which DNA is selectively adsorbed to a silica gel membrane at pH below 7.5 at high salt concentration. The impurities are separated from the membrane, then the DNA is eluted therefrom using Tris buffer or water. Sequencing was carried out on an automated DNA sequencer (Applied Biosystems Division, Perkin Elmer, Inc., Foster City, Calif.) using 2',3'-dideoxynucleotide chain terminators (Sanger et al. (1977)) that carried fluorescent labels.

Complete VP1 PCR products of viruses for which VP1 primers were not available were obtained by cloning the viral cDNA into the plasmid pGEM-T (Promega Corp., Madison, Wis.). Nested-deletion subclones were constructed from the resulting plasmid with an Erase-a-Base™ kit (Promega Corp.). In this procedure, the plasmid is first digested with a restriction nuclease providing either a blunt end or a 5' overhang. The opened plasmid is then digested with a 3'-5' exonuclease, *E. coli* exonuclease III, to remove plasmid sequences unrelated to the viral VP1 gene. The extended 5' overhang is then removed using S1 nuclease, and the plasmid is resealed by first repairing the ends with DNA polymerase, then ligating with DNA ligase. The resulting shortened plasmid is propagated in a suitable host to provide larger amounts of the plasmid, including the VP1 sequence. For each virus, at least two independent clones were sequenced by automated methods as described above.

Using these procedures, complete VP1 nucleotide sequences were determined for 57 human non-polio enterovirus strains for which VP1 sequences had not previously been determined. These are summarized in Table 2, which shows both the GenBank accession numbers (numbers AF081293 to AF081349) and the corresponding SEQ ID NOs, 23–79. Forty-seven of the strains were prototype strains for recognized human enterovirus serotypes (Melnick (1996)). The other ten sequenced strains were well-characterized antigenic variants which, while antigenically distinct from their respective prototype strains, were similar enough to them to have been considered to be the same serotype (Committee on Enteroviruses of the National Foundation for Infantile Paralysis, Am. J. Public Health 47:1556–1566 (1957); Melnick (1996)). Combined with the 21 previously available complete enterovirus VP1 sequences, of which 19 are prototypes and 2 are variants, the database constructed for use in the present method includes 66 prototype VP1 sequences and 16 variants or other enteroviruses, including the three poliovirus Sabin strains and the Barty variant of E9.

The boundaries of the newly sequenced VP1 genes were predicted by comparison of the nucleotide and deduced amino acid sequences with those of previously characterized enteroviruses. Human-enterovirus VP1 sequences varied in length from 834 to 951 nucleotides (278 to 317 amino acid residues). The CB group has the shortest predicted VP1 amino acid sequences (278 to 298 residues), while EV68 and EV70 had the longest ones (312 and 317 residues, respectively).

Each of the enterovirus VP1 sequences developed in this work is characteristic of the serotype from which it arises, and differs from the sequence of every other serotype. For this reason, the VP 1 sequences can be used as markers for the prototypical serotypes of the non-polio enteroviruses. The 66 prototype and 16 variant sequences identified above are used in the method of the present invention to form the content of a database for use in typing an enterovirus obtained in a clinical sample.

EXAMPLE 2

Design of Non-Polio Enterovirus PCR Primers and Assessment of the Breadth of Their Specificity Design of PCR primers. Since the VP1 sequence was found to correlate with serotype (Example 1), this region was targeted for development of sequence-based molecular diagnostics, namely, generic PCR primers to amplify and sequence a portion of the VP1 gene. Degenerate deoxyinosine-containing PCR primers were designed which specifically recognize regions within or near the termini of the VP1 gene of non-polio enteroviruses. Primers with the broadest specificity within the non-polio enterovirus genus were chosen by searching for regions in the genome that encode amino acid motifs within VP1 and those immediately C-terminal to VP1, in 2A, that are the most conserved across the prototypes. (Echoviruses E22 and E23 were excluded, because it is likely that they will be reclassified as members of a new Picornavirus genus, *Parechovirus* (Mayo et al., J. Gen. Virol. 79:649–657 (1997)). The motif MYVPPG (Met-Tyr-Val-Pro-Pro-Gly) (SEQ ID NO:87) was present in the deduced VP1 amino acid sequences of 44 enterovirus prototype strains whose nucleotide sequences are provided in Example 1. Thirteen prototypes had Ile substituted for Val and CA7 contained Ala instead of Val. CA12, CA14, and EV71 contain the motif, MFVPPG (Met-Phe-Val-Pro-Pro-Gly) (SEQ ID NO:88). In EV68 and 70, a slightly different motif was present, MYVPTG (Met-Tyr-Val-Pro-Thr-Gly) (SEQ ID NO:89). For viruses in the CB-like phylogenetic group the M(Y/F)(V/I)PPG motif is followed by Gly (SEQ ID NO:86), whereas in all other enteroviruses, the motif is followed by Ala (A) (SEQ ID NO:86). To account for differences between the virus groups and for codon degeneracy, two different inosine-containing primers were designed to anneal to this region. Primer 012 (ATGTAYGTICCICCIGGIGG) (SEQ ID NO:4) is based on the amino acid sequence, MYVPPGG (SEQ ID NO:80). Primer 040 (ATGTAYRTICCIMCIGGIGC) (SEQ ID NO: 9) is based on the amino acid sequence, MY(V/I)P(P/T)GA (SEQ ID NO:81). The selectivity of these two primers is primarily due to the first position at the 3' end of each primer (i.e., in primer 012, the base at the 3' end is G, and in primer 040, the base at the 3' end is C) (see Table 3.) In addition, primer 040 contains increased degeneracy at positions 8 and 14 from the 3' end of the primer in order to detect those viruses which encode an isoleucine (position 8) or a threonine (position 14) in these positions. For PCR, primers 012 and 040 were each paired with primer 011 (GCICCIGAYTGITGICCAA) (SEQ ID NO:3), which corresponds to the amino acid motif FG(Q/H)QSGA (Phe-Gly-(Gln/His)-Gln-Ser-Gly-Ala; SEQ ID NO:82), present near the 5' end of the 2A gene and which is conserved among most enteroviruses for which the 2A sequence is available.

Figure 2:
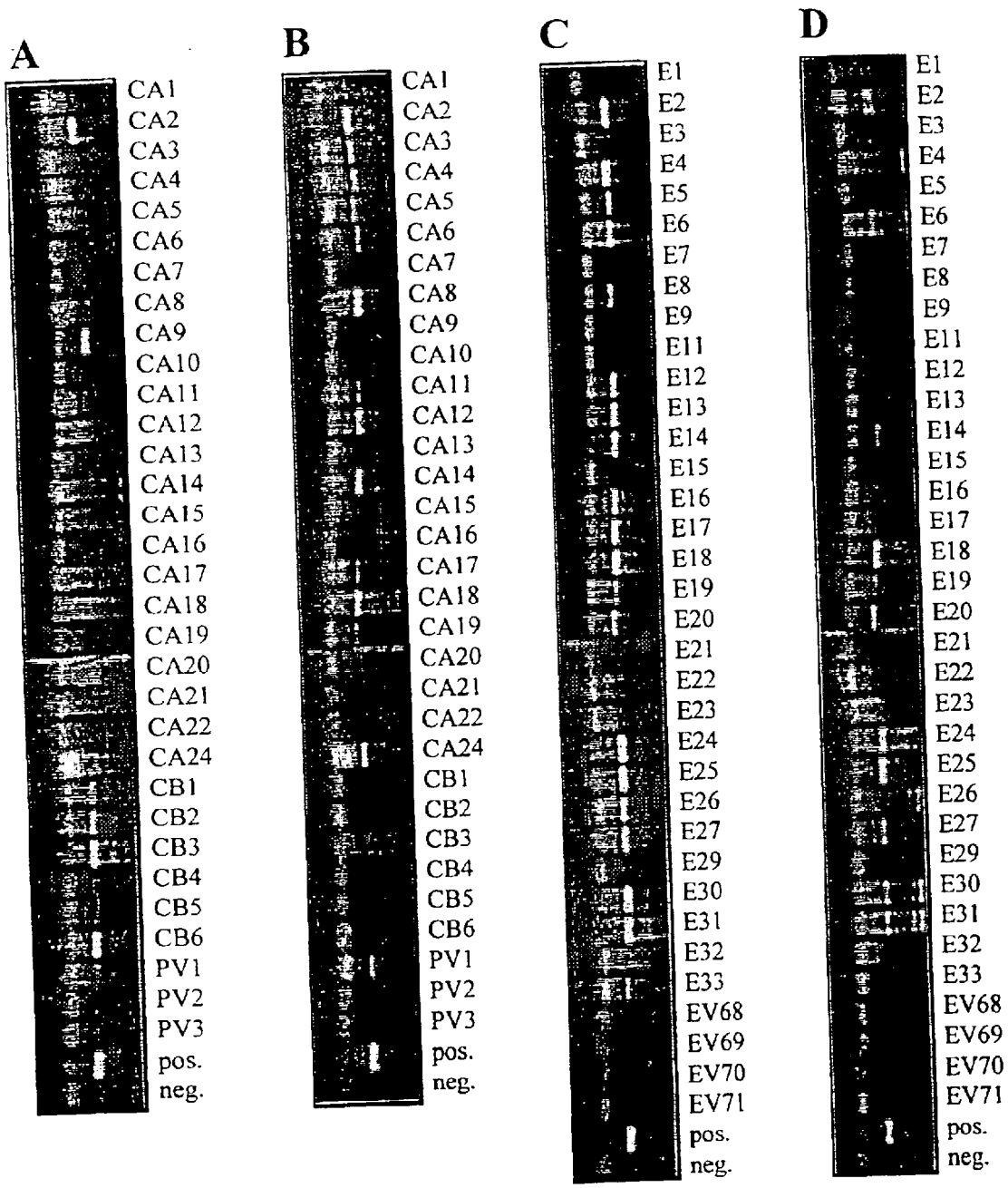

Specificity of PCR Primers. To assess the breadth of specificity and thereby the general applicability of the 012/011 and 040/011 primer pairs, both pairs were tested in RT-PCR reactions with template RNA derived from each of the human non-polio enterovirus prototype strains (see FIG. 2). Primer pair 012/011 amplified 23 of 30 echovirus prototypes (FIG. 2C), as well as CA2, CA7, CA9, CA11, CB1, CB2, CB3, CB6, and PV1 (Poliovirus 1) (FIG. 2A). Primer pair 040/011 amplified 14 of 23 CA prototypes and PV1 (FIG. 2B), as well as E2, E6, E14, E16, E18, E19, E20, E24, E25, E27, E30, and E31 (FIG. 2D). Twenty-two prototypes were not amplified by either primer pair (CA10, CA13, CA15, CA16, CA20, CA21, CA22, CB4, CB5, E1, E7, E9, E21, E22, E23, E32, EV68, EV 69, EV70, EV71, as well as PV2 and PV3, where PV signifies poliovirus).

EXAMPLE 3

Typing of Clinical Isolates Obtained in the Field

Viruses. Fifty-one virus isolates of 24 different serotypes were chosen from those processed in the inventors' laboratory at the Centers for Disease Control and Prevention (CDC) during the period 1991–1998 for routine non-polio enterovirus reference testing. The viruses were from 19 different states in the United States and two other countries, and were chosen to be representative of the serotypes in the collection for the period surveyed. To avoid the effects of sampling bias in the interpretation of sequence comparisons, no more than four isolates of any given serotype were chosen for sequencing. The isolates included examples of coxsackievirus A, coxsackievirus B, echovirus, and numbered enteroviruses.

Virus isolation and neutralization. The virus strains were isolated from a wide range of clinical specimens, including blood (n=1), cerebrospinal fluid (n=7), conjunctival swab (n=1), "lesion" (n=1), postmortem lung (n=1), nasopharyngeal swab (n=2), sputum (n=1), stool (n=18), throat swab (n=8), and tissue not specified (n=11). Forty-four of the 51 strains were originally isolated by the submitting laboratory, most of which were state public health laboratories in the United States. The remaining seven strains were isolated from original stool specimens at CDC. All isolates were typed antigenically using WHO-standard antiserum pools (Melnick et al., 1973), supplemented with additional pooled and monospecific antisera such that all human enterovirus serotypes, as well as antigenic variants of E4, E6, E11, and E30, could be identified (P. Feorino, personal communication to the inventors).

RNA extraction and RT-PCR. Viral RNA was extracted from infected cell culture supernatant using the QIAamp™ Viral RNA Kit (QIAGEN, Inc.). Reverse-transcription polymerase chain reaction (RT-PCR) was carried out as described previously (Oberste et al., (1998a,b)). From each viral cDNA, an amplicon of approximately 450 bp, encompassing the 3' half of VP1 and the 5' end of 2A, was amplified by PCR using the primers 012/011 or 040/011 (Table 3). Primer specificity was tested by PCR amplification of the prototype strain of each human enterovirus serotype with both primer pairs. Amplification products were visualized by agarose gel electrophoresis and ethidium bromide staining. PCR products from clinical isolates were gel-isolated and purified for sequencing using the QIAquick™ Gel Extraction Kit (QIAGEN, Inc.) and sequenced on an automated DNA sequencer using fluorescent dideoxy-chain terminators as in Example 1 (Applied Biosystems Division, Perkin Elmer, Inc.). The sequences obtained for the clinical samples were deposited in the GenBank sequence database (Accession Numbers AF081595-AF081645).

Sequence analysis. The sequences were compared to the enterovirus VP1 sequence database developed in Example 1 by sequential pairwise alignment of the query sequence with each sequence in the database, using the algorithm of Needleman and Wunsch (1970), implemented in the program Gap (Wisconsin Sequence Analysis Package, version 9.1). The results of the pairwise comparisons were compiled and sorted in descending order by percent identity with the query sequence.

PCR-amplification of clinical isolates. In order to establish the utility of using viral sequence analysis as an enterovirus typing tool, typing by partial sequencing of VP1 was compared with the conventional serological typing method using 52 clinical isolates typed in the inventors' laboratory from 1991 to 1997. Partial VP1 sequences relate to obtaining sequences in a region of approximately 400 nucleotides at the 3' end of the VP1 gene. Despite the failure of primer pair 012/011 to amplify the E7, E9, E21, CB4 and CB5 prototype strains (see Example 2), 012/011 successfully amplified recent clinical isolates of each these serotypes. Likewise, primer pair 040/011 amplified recent isolates of CA16, CA21, and EV71, but not the prototype strains of these serotypes (see Example 2). Taken together, these two primer pairs failed to amplify only one clinical isolate of the 52 tested, a 1993 EV6 isolate from Texas (TX93–1673). The presence of amplifiable RNA in the latter specimen was confirmed by amplification of 5'-specific sequences by pan-enterovirus primers (data not shown). For the other 51 isolates, a VP1-specific fragment was amplified from purified RNA by RT-PCR using primer pairs 012/011 or 040/011. In most cases, only one of the two primer pairs produced an amplicon of the expected size (data not shown).

Typing of clinical isolates by nucleotide sequence analysis. The PCR products were gel isolated and sequenced. The sequences were compared to the complete enterovirus VP1 database developed in Example 1 by pairwise alignment of the isolate sequence to each sequence in the database using the program Gap. These comparisons produced, for each clinical isolate, a set of values of the percent identity giving the extent of identity between the sequence of the given clinical isolate and each of the prototype sequences in the database. Typing was obtained as that prototype whose extent of identity to the clinical sample was the highest of all the prototypes. In general, as implemented in this study, if the highest global identity is >75%, the clinical sample and the prototype are of the same serotype. If the highest score is 70%–75%, the identification is presumptive and should be confirmed by neutralization using monospecific antisera specific for each of the four highest scoring prototypes. If the highest score is <70%, the clinical sample is considered to be of no known serotype; for example, it may be from a picornavirus for which a sequence is not yet available, or it may be a new enterovirus serotype. For each clinical isolate, the matches with the highest and second highest pairwise identity score were identified. Table 4 shows the serotype as obtained from the classical neutralization test, as well as the types of the highest and next highest scoring prototypes obtained in this way (with entries giving the extent of identity of both the nucleotide sequences (nt) and the translated amino acid sequences(aa)). Strains in Table 4 are identified by U.S. state (two letter code) or country (three letter code) of origin, year of isolation, and lab identifier number. For example, WA91-0374 indicates that the strain was isolated in the state of Washington in 1991 and the lab sample number was 0374. The abbreviations DOR and PER in Table 4 designate the Dominican Republic and Peru, respectively.

TABLE 4

Correspondnce Between Typing by Sequenc and by Neutralization.

| | | Highest Scoring Prototype | | | Second Highest Scoring Prototype(s) | | |
|---|---|---|---|---|---|---|---|
| Strain | Type | Type | nt (%) | aa (%) | Type | nt (%) | Type | aa (%) |
| WA91-0374 | E6 | E6 | 83.3 | 95.6 | E1 | 69.7 | E29 | 74.3 |
| OR91-1426 | E30 | L30 | 85.8 | 92.9 | E21 | 69.5 | E21 | 81.7 |
| CT92-1465 | E16 | E16 | 81.4 | 93.6 | E5 | 72.2 | E5 | 78.6 |
| FL92-1512 | CB2 | C82 | 86.5 | 98.5 | CB4 | 68.3 | CB4 | 75.2 |
| WA92-1516 | E11' | E11 | 77.1 | 90.1 | E11 | 72.9 | E19 | 83.0 |

TABLE 4-continued

Correspondence Between Typing by Sequence and by Neutralization.

| | | Highest Scoring Prototype | | | Second Highest Scoring Prototype(s) | | | |
|---|---|---|---|---|---|---|---|---|
| Strain | Type | Type | nt (%) | aa (%) | Type | nt (%) | Type | aa (%) |
| NC92-1612 | E9 | E9 | 77.8 | 94.6 | E17 | 70.2 | E16 | 72.9 |
| GA92-1616 | E11 | E11 | 77.6 | 89.4 | E19 | 72.2 | E19 | 82.3 |
| TX92-1647 | CA14 | CA14 | 86.8 | 91.1 | CA7 | 63.4 | CA7 | 67.9 |
| MD92-1649 | E25 | E25 | 77.1 | 91.5 | E1 | 68.5 | E21 | 77.6 |
| DOR93-1657 | CA24v | CA24 | 77.4 | 92.8 | CA20 | 67.6 | CA17 | 75.9 |
| FL93-1763 | E11' | E11 | 78.5 | 90.1 | E19 | 72.6 | E19 | 83.0 |
| GA93-1763 | CA9 | CA9 | 93.8 | 95.3 | E4 | 68.6 | E4 | 70.8 |
| GA93-1765 | E7 | E7 | 79.7 | 95.7 | E32 | 68.8 | E32 | 77.1 |
| MO93-1808 | E25 | E25 | 77.6 | 91.5 | E33 | 67.5 | E21 | 76.9 |
| ME93-1814 | CB5 | CB5 | 95.2 | 98.5 | CB1 | 71.3 | CB1 | 77.7 |
| NM93-1816 | CB3 | CB3 | 90.3 | 97.7 | CB6 | 69.9 | CB1 | 81.5 |
| OR93-1817 | E25 | E25 | 77.9 | 91.5 | E1 | 68.5 | E21 | 76.9 |
| WA93-1821 | E4 | E4 | 81.1 | 96.1 | E1 | 73.1 | E1 | 80.9 |
| MN94-1828 | E25 | E25 | 76.9 | 92.2 | E29 | 67.9 | E21 | 77.6 |
| WA94-1849 | E3 | E3 | 79.6 | 93.0 | E7 | 68.2 | E12 | 80.0 |
| AR94-1884 | E30 | E30 | 96.0 | 93.6 | E21 | 70.0 | E21 | 82.4 |
| GA93-2460 | CB5 | CB5 | 95.8 | 93.5 | CB1 | 70.8 | CB1 | 77.7 |
| GA93-1892 | E30 | E30 | 85.5 | 93.6 | E21 | 69.5 | E21 | 83.4 |
| GA93-1994 | E7 | E7 | 79.7 | 95.7 | E32 | 69.1 | E32 | 77.1 |
| NM94-1919 | EV71 | EV71 | 80.6 | 93.4 | CA16 | 66.9 | CA16 | 76.6 |
| AZ94-1925 | CA14 | CA14 | 86.5 | 97.0 | CA7 | 63.8 | CA7 | 68.2 |
| RI94-1959 | E21 | E21 | 78.3 | 93.7 | E30 | 69.6 | E30 | 80.0 |
| CT94-2006 | EV71 | EV71 | 80.3 | 93.4 | CA16 | 66.0 | CA16 | 76.6 |
| MD95-2037 | EV71 | EV71 | 79.9 | 92.7 | CA16 | 67.0 | CA16 | 76.6 |
| AZ94-2060 | CA21 | CA21 | 90.9 | 98.6 | CA24 | 68.7 | CA24 | 75.5 |
| PA94-5753 | CA16 | CA16 | 77.9 | 94.7 | EV71 | 68.7 | EV71 | 83.0 |
| NM95-2070 | E6 | E6 | 76.8 | 94.1 | E29 | 68.1 | E29 | 75.5 |
| TX95-2089 | E13 | E13 | 72.4 | 88.7 | EV69 | 71.5 | EV69 | 93.0 |
| GA95-2093 | CA21 | CA21 | 91.4 | 98.6 | CA24 | 67.5 | CA24 | 75.5 |
| GA95-2095 | CA16 | CA16 | 77.9 | 94.9 | EV71 | 69.4 | EV71 | 77.4 |
| NC95-2135 | CB2 | CB2 | 83.2 | 99.2 | CB4 | 68.3 | C84 | 76.2 |
| AR95-2139 | E9 | E9 | 75.7 | 92.8 | E17 | 70.0 | E1 | 71.8 |
| TX95-2147 | CA16 | CA16 | 76.5 | 94.9 | EV71 | 70.4 | EV71 | 77.4 |
| VA95-2154 | E11' | E11 | 78.3 | 90.8 | E19 | 71.7 | E19 | 83.7 |
| WT95-7151 | E9 | E9 | 75.7 | 93.5 | E17 | 69.4 | E16 | 71.4 |
| VA95-2157 | E30 | E30 | 85.3 | 92.1 | E21 | 70.0 | E21 | 82.1 |
| GA96-2175 | CA9 | CA9 | 81.5 | 92.6 | E19 | 68.4 | E11 | 72.3 |
| CT96-2181 | E5 | E5 | 86.5 | 92.9 | E31 | 71.5 | E31 | 82.1 |
| CT96-2181 | E18 | E18 | 75.7 | 93.6 | E17 | 69.9 | E4 | 75.4 |
| TX97-2184 | CA21 | CA21 | 91.6 | 98.6 | CA24 | 68.2 | CA24 | 75.5 |
| TX97-2320 | E18 | E18 | 78.8 | 92.9 | E17 | 69.7 | E17 | 74.5 |
| NH97-2342 | CB3 | CB3 | 77.4 | 98.5 | CB5 | 67.9 | CB1 | 84.6 |
| PER98-2528 | E6 | E6 | 86.0 | 95.6 | CB1 | 71.6 | E29 | 74.3 |
| PER98-2533 | E7 | E7 | 80.4 | 95.7 | E32 | 68.1 | E12 | 78.6 |
| PER98-2537 | E11 | E11 | 78.5 | 94.3 | E19 | 71.9 | E19 | 82.3 |
| PER98-2558 | E33 | E33 | 79.3 | 96.9 | CB1 | 70.3 | E4 | 75.4 |

The typing results for the 51 isolates shown in Table 4, fully correlate with the serotype as determined by the conventional neutralization test (Table 4). The nucleotide sequences of the various clinical isolates ranged from 72.4% identity to 95.2% identity with the sequences of the respective prototype strains and only from 63.4% identity to 73.1% identity to the sequences of the second highest scoring prototypes. The predicted amino acid sequences of the clinical isolates ranged from 88.7% identity to 98.5% identity with that of the cognate prototype strain and from 67.7% identity to 84.6% identity to that of the second highest scoring prototype strain. With one exception, the difference between percent nucleotide sequence identity to the highest scoring prototype and the percent identity to the second highest scoring prototype was 4.2%. In the exception (TX95-2089), typed antigenically as E13, the highest-to-second-highest difference was only 0.9% (72.4% identical to E13 vs. 71.5% identical to EV69), suggesting that either TX95-2089 has diverged significantly from E13 or EV69, or that the E13 prototype strain (Del Carmen) is not representative of the serotype as a whole. When the complete VP1 nucleotide sequence of TX95-2089 was examined, it was found to be 72.6% identical to that of the E13 prototype, 70.1% identical to that of the EV69 prototype (second highest score), and 64.7% identical to that of the E12 prototype (third highest score). The predicted complete VP1 amino acid sequence of TX95-2089 was 88.2% identical to that of E13, 80.8% identical to that of EV69 (second highest score), and 70.0% identical to that of CB1 (third highest score), suggesting that TX95-2089 is probably a strain of E13 which has diverged in nucleotide sequence by accumulating mutations in the third codon position. TX95-2089 was neutralized by monospecific anti-E13 antisera but not by monospecific anti-EV69 antisera (data not shown).

The typing procedure described in this invention contravenes the evaluation of the state of the art in Holland et al. (J. Clin. Microbiol. 36:1588–1594 (1998)), which states that PCR is not able successfully to type enterovirus infections. Furthermore, Oberste et al. (1998a) conducted sequence and phylogenetic analyses of all human enterovirus serotypes based on a portion of the VP2 gene. They determined that this portion of VP2 may be inappropriate for consistent molecular inference of serotype. For these reasons, the method of the present invention, as described above and exemplified in Examples 1-3, provides results that are unexpected by workers in the field.

EXAMPLE 4

Detection of a Broad Range of Picornaviruses

The present method has been applied to the detection of a broad range of picornaviruses that afflict both human and nonhuman subjects, according to the procedures generally followed in Example 2.

In addition to the primers 011, 012, and 040, additional primers directed to the detection of human and nonhuman picornaviruses were devised. These are provided as Primer 187 (ACIGCIGYIGARACIGGNCA) (SEQ ID NO:19) that hybridizes to a sequence encoding the amino acid motif TA(A/V)ETGH (SEQ ID NO:83), Primer 188 (ACIGCIGTIGARACIGGNG) (SEQ ID NO:20) that hybridizes to a sequence encoding the amino acid motif TAVETG(AfV) (SEQ ID NO:84), Primer 189 (CARGCIGCIGARACIGGNGC) (SEQ ID NO:21) that hybridizes to a sequence encoding the amino acid motif QAAETGA (SEQ ID NO:85), and Primer 222 (CICCIGGIGGIAYRWACAT) (SEQ ID NO:22) that hybridizes to a sequence encoding a motif M(F/Y)(IV)PPG(A/G) (SEQ ID NO:86) (see Table 3). Primer 187 is directed to amplification of the CB and E groups in the forward direction (i.e., it hybridizes to the sense strand of the cDNA), Primer 188 is directed to amplification of the poliovirus (PV) group, EV68 and EV70 in the forward direction, Primer 189 is directed to amplification of the group of CA16-like viruses (Oberste et al., J. Virol. 73:1941–1948 (1999)) in the forward direction, and Primer 222 is directed to amplification of all enteroviruses in the reverse direction (i.e., it hybridizes to the antisense strand of the cDNA).

In this example, prototypical serotypes of human enteroviruses were subjected to RT-PCR using, in separate experiments, primer pairs 012/011 (SEQ ID NOs:3 and 4), 0401/011 (SEQ ID NOs:3 and 9), 187/222 (SEQ ID NOs:19 and 22), 188/222 (SEQ ID NOs:20 and 22), and 189/222 (SEQ ID NOs:21 and 22). The results are shown in Table 5. Additionally several serotypes from a selection of human and nonhuman picornaviruses, namely bovine enterovirus, human rhinovirus, and simian picornavirus, were examined according to the present method. For simian picornaviruses and HRV2, actual experiments were done. For the other serotypes considered, provision of an amplicon was predicted by comparison of the primer sequence to each of the viral VP1 sequences. The results of this experiment are shown in Table 6.

TABLE 5

Amplification of Human Enterovirus Serotypes by Specific Primer Pairs.

| Virus | 012/011 | 040/011 | 187/222 | 188/222 | 189/222 |
|---|---|---|---|---|---|
| CA1 | — | — | — | ■ | □ |
| CA2 | □ | ■ | □ | □* | ■ |
| CA3 | — | ■ | — | □ | ■ |
| CA4 | — | ■ | — | — | ■ |
| CA5 | — | ■ | □ | □* | ■ |
| CA6 | — | ■ | — | □* | ■* |
| CA7 | — | — | ± | — | ■ |
| CA8 | — | □ | — | □ | ■ |
| CA9 | ■ | — | ■* | □ | — |
| CA10 | — | — | — | □ | ■ |
| CA11 | — | ± | — | ■ | □ |
| CA12 | — | ■ | — | □* | ■ |
| CA13 | — | — | □* | ■ | □ |
| CA14 | — | ■ | — | □ | ■ |
| CA15 | — | — | □ | ■ | □ |
| CA16 | — | ■ | — | — | ■ |
| CA17 | — | ± | ± | ■ | □ |
| CA18 | — | ■ | — | (±) | — |
| CA19 | — | ± | — | ■ | □ |
| CA20 | — | — | — | ■ | ± |
| CA21 | — | ■ | — | ■ | □ |
| CA22 | — | — | — | ■ | □ |
| CA24 | — | ■ | — | ■ | □ |
| CB1 | ■ | — | ■ | — | — |
| CB2 | ■ | — | ■ | □* | ± |
| CB3 | ■ | ± | ■* | — | ± |
| CB4 | — | — | ■* | — | ± |
| CB5 | ■ | — | ■ | □ | □ |
| CB6 | ■ | — | ■ | □* | □* |
| PV1 | — | ■ | □ | ■ | □ |
| PV2 | — | — | □ | ■ | □* |
| PV3 | — | — | — | ■ | □ |
| E1 | — | — | ■ | — | — |
| E2 | ■ | □ | ■ | — | ± |
| E3 | ■ | — | ■ | — | ± |
| E4 | ■ | — | ■* | □ | □* |
| E5 | ■ | — | ■ | — | ± |
| E6 | ■ | □ | ■ | — | ± |
| E7 | ■ | — | (±) | — | □ |
| E9 | ■ | — | ■ | — | ± |
| E11 | ■ | — | ■* | — | ± |
| E12 | ■ | — | ■* | — | □* |

TABLE 5-continued

Amplification of Human Enterovirus Serotypes by Specific Primer Pairs.

| Virus | 012/011 | 040/011 | 187/222 | 188/222 | 189/222 |
|---|---|---|---|---|---|
| E13 | ■ | — | ■ | — | □ |
| E14 | ■ | □ | ■ | — | □* |
| E15 | — | — | ■ | — | — |
| E16 | ■ | — | ■ | — | ± |
| E17 | ■ | — | ■* | — | ± |
| E18 | ■ | □ | ■ | □ | □ |
| E19 | ■ | — | ■ | — | ± |
| E20 | ■ | □ | ■ | □ | ± |
| E21 | ■ | — | ■ | — | — |
| E24 | ■ | □ | ■ | — | ± |
| E25 | ■ | □ | ■ | — | ± |
| E26 | ■ | — | ■ | — | ± |
| E27 | ■ | □ | ■* | — | ± |
| E29 | — | — | ■ | — | — |
| E30 | ■ | □ | ■ | — | ± |
| E31 | ■ | □ | ■* | — | ± |
| E32 | — | — | ■ | — | ± |
| E33 | ■ | — | ■ | — | — |
| EV68 | — | — | □ | ■ | □ |
| EV69 | — | — | ■ | — | — |
| EV70 | — | — | — | ■ | □ |
| EV71 | — | ■ | — | — | ■ |

CA, coxsackie A virus; CB, coxsackie B virus; PV, poliovirus; E, echovirus; EV, numbered enterovirus. Results are for amplication of prototype strains and/or clinical isolates of the indicated serotypes, based on testing in a standard RT-PCR assay for human enteroviruses (Oberste et al., 1999).

□ and ■ : strong amplification, single band on gel;

■ indicates the primer pair giving optimal amplification for a particular serotype.

± and (±): weak amplification, single band on gel; (±) indicates the primer pair giving optimal amplification for a particular serotype.

□* and ■*: strong amplification, multiple bands on gel;

■* indicates the primer pair giving optimal amplification for a particular serotype.

—: No amplication observed.

TABLE 6

Predicted and Observed Results of Amplification of Picornavirus Serotypes by Specific Primer Pairs.

| Virus | 012/011 | 040/011 | 187/222 | 188/222 | 189/222 |
|---|---|---|---|---|---|
| BEV1 | | | | [■] | |
| BEV2a | | | | [■] | |
| BEV2b | | | | [■] | |
| HRV1b | | | [■] | | |
| HRV2 | | | ■ | | |
| HRV3 | | | | [■] | |
| HRV14 | | | | [■] | |
| HRV16 | | | [■] | | |
| HRV89 | | [(±)] | | | |
| SPV2 | | | ■ | | |
| SPV9 | — | — | — | — | — |
| SPV10 | ■ | | | | |
| SPV11 | — | — | — | ■ | — |
| SPV12 | — | — | — | — | ■ |
| SPV13 | ■ | | | | |
| SPV15 | — | — | — | ■ | — |
| SPV16 | — | — | — | — | ■ |
| SPV17 | | | ■ | | □ |

BEV, bovine enteroviruses; HRV, human rhinovirus; SPV, simian picornavirus. Results are for amplification of prototype strains and/or clinical isolates of the indicates serotypes, based on testing in a standard RT-PCR assay (Oberste et al., 1999) for HRV2, and simian picornaviruses. For the other viruses (indicated by square brackets [ ]), the entry provides a predicted result based on comparison of the primer sequences with the available VP1 nucleotide sequences found in the GenBank database.

□ and ■ : strong amplification, single band on gel;

■ indicates the primer pair giving optimal amplification for a particular serotype.

(±): weak amplification, single band on gel, optimal amplification for a particular serotype.

—: No amplification observed.

Empty cells indicate primer-template combinations that have not yet been tested.

The results for 012/011 and 040/011 in Table 5 tabulate the observations already discussed with respect to FIG. 2 in Example 2.

Taking the results for primer pairs 187/222, 188/222, and 189/222 in Tables 5 and 6 together, it is seen that these primer pairs amplify all human enteroviruses, and five of the six simian picornaviruses tested. They should also amplify the three bovine enteroviruses and all six human rhinoviruses for which VP1 sequences are available in GenBank; other than HRV2, these have not yet been directly tested. Furthermore, the three simian picornaviruses that were not tested using primer pairs 187/222, 188/222, and 189/222 were successfully amplified by primer pair 040/011 (see Table 6).

We claim:

1. A method for detecting the presence of an enterovirus in a sample comprising the steps of:
   (i) purifying RNA contained in the sample;
   (ii) reverse transcribing the RNA with primers effective to reverse transcribe enteroviral RNA to provide a cDNA;
   (iii) contacting at least a portion of the cDNA with
      (a) a composition that promotes amplification of a nucleic acid and
      (b) an oligonucleotide mixture wherein the mixture comprises at least one oligonucleotide that hybridizes to a highly conserved sequence of the sense strand of an enterovirus nucleic acid and at least one oligonucleotide that hybridizes to a highly conserved sequence of the antisense strand of an enterovirus nucleic acid, wherein said mixture comprises SEQ ID NO:19;
   (iv) carrying out an amplification procedure on the amplification mixture such that, if an enterovirus is present in the sample, an enterovirus amplicon is produced whose sequence comprises a nucleotide sequence of at least a portion of the VP1 gene of the enterovirus genome; and
   (v) detecting whether an amplicon is present; wherein the presence of the amplicon indicates that an enterovirus is present in the sample.

2. The method as described in claim 1, wherein the highly conserved sequences occur within the VP1 gene or within about 100 nucleotides from a terminus of the VP1 gene.

3. The method as described in claim 2, wherein at least one oligonucleotide comprises, at the 3' end thereof, a sequence that hybridizes to a sequence encoding a motif chosen from the group consisting of the sequences given by SEQ ID NO:83, SEQ ID NO:84, and SEQ ID NO:85, and at least one oligonucleotide comprises, at the 3' end thereof, a sequence that hybridizes to a sequence encoding a motif given by SEQ ID NO:86.

4. The method as described in claim 1, wherein the oligonucleotide mixture comprises an oligonucleotide whose sequence comprises, at the 3' end thereof, the sequence given by SEQ ID NO:22, and an oligonucleotide whose sequence comprises, at the 3' end thereof, the sequence given by SEQ ID NO:19.

5. The method as described in claim 1, wherein the oligonucleotide mixture comprises an oligonucleotide whose sequence is given by SEQ ID NO:22, and an oligonucleotide whose sequence is given by SEQ ID NO:19.

6. The method as described in claim 1, wherein the amplification procedure comprises a polymerase chain reaction.

7. The method as described in claim 1, wherein the sample is chosen from the group consisting of whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal.

8. The method as described in claim 1, wherein the detection is carried out by a procedure chosen from the group consisting of gel electrophoresis and visualization of amplicons contained in a resulting gel, size separation matrix, capillary electrophoresis and detection of the emerging amplicon, probing for the presence of the amplicon using a labeled probe, sequencing the amplicon, and labeling a PCR primer employed in the method and detecting the label.

* * * * *

SEQUENCE LISTING

<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 1
gcrtgcaatg ayttctcwgt                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(18)
<223> OTHER INFORMATION: n = a, t, c or g

<400> SEQUENCE: 2
ngcnccdgat tgntgscc                                                18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 3
gcnccngayt gntgnccraa                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 4
atgtaygtnc cnccnggngg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)

<223> OTHER INFORMATION: n = a, t, c or g

<400> SEQUENCE: 5
ggngcrttnc cytcngtcca                                          20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 6
acrtgncnng tytgcatngt                                          20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(18)
<223> OTHER INFORMATION: n = a, t, c or g

<400> SEQUENCE: 7
awnttytayg ayggntgg                                            18

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 8
tananngtnc ccatrttrtt                                          20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 9
atgtayrtnc cnmcnggngc                                          20

<210> SEQ ID NO 10
<211> LENGTH: 20
<212> TYPE: DNA
<213> ORGANISM: Artificial Sequence -continued

```
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 10
ggnggnggrt cngtnakytt                                            20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 11
gangaraayc tnatngarac                                            20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(19)
<223> OTHER INFORMATION: n = a, t, c or g

<400> SEQUENCE: 12
cccatnakrt cnatrtccc                                             19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 13
gtrctyacna nnagrtcyct                                            20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(19)
<223> OTHER INFORMATION: n = a, t, c or g

<400> SEQUENCE: 14
tsaarytgtg caargacac                                             19
```

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(18)
<223> OTHER INFORMATION: n = a, t, c or g

<400> SEQUENCE: 15
stgyccagat ttcagtgt                                                 18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 16
ggnacncayr tnathtggga                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 17
gccntrttnt grtgnccraa                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 18
ggnacncayr tnrtntggga                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)

<223> OTHER INFORMATION: n = a, t, c or g

<400> SEQUENCE: 19
acngcngyng aracnggnca                    20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(19)
<223> OTHER INFORMATION: n = a, t, c or g

<400> SEQUENCE: 20
acngcngtng aracnggng                     19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 21
cargcngcng aracnggngc                    20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(19)
<223> OTHER INFORMATION: n = a, t, c or g

<400> SEQUENCE: 22
cnccnggngg nayrwacat                     19

<210> SEQ ID NO 23
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 23
ggattgggcg attctattga ggctgccatt gacagcatca cacaaaatgc actaaccact      60
gtacaaaata caacacaatc aggacctact cattcaaaag aagttccagc attaacagca    120
gtggaaacag gtgctactag tcaagtagaa ccaggtgact tgattgaaac cagacatgtt    180
ataaacatga gacaaagatc tgaagcatct atcgaatctt tctttggccg atccgcatgt    240
gttgcgatac ttggttttgtc aaacgccaaa ccaactgaca caaacaccaa acaattgttc    300
aaaacatgga gaatatcata tttagaaact caccaactca gaagaaaact tgagttcttt    360

```
acgtactcaa ggtttgattt ggaaatgacc atagtaatta cagagagggt tttcaatgca      420
gtcaatgtcc cattgcgcaa ttatgtgtac caaataatgt acgttccccc aggtgctcca      480
gaaccacaat catgggatga ttacacgtgg caatcttcta ccaacccatc aatattctac      540
accactggaa atgctcctcc cagagtgtca attccatttg ttggaatagg gtctgcatat      600
tcacactttt atgatggttt ctcacagatt cctcttgact caatcagtgc tggagcaagt      660
aataagtatg gttacacttc aatcaatgac tttggtaccc tggcaattag aatagtaaat      720
gaatatgacc cagtgcaagt ggatgcaaag gcccgagtgt atattaaacc caaacatgtt      780
cgcatgtggt gccccagacc accacgggcc atgccttaca agaatagcac agtggatttc      840
gacccatcag caactgtaat gacccaagtc gcagacatca ggacgtat                  888

<210> SEQ ID NO 24
<211> LENGTH: 882
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 24
ggagatccag tggaagactt aatcgccaat acagttgcta ggactctaga gagaataacc       60
tctccaactc ataatacaac ggcaggcaac accaccgtta gcgagcacag catcggtacc      120
ggttcagtgc ctgcgttgca agctgctgag actggggctt cgtctaacac cacagatgag      180
agtatgatag aaacacggtg tgttgtcaat aggaatggag tgattgagac tagcatcaac      240
catttcttct cccgagcggg gcttgtggga gtgctgaaca tacttgatgg aggcaccctca     300 aaaggctttg aagtttggga tatagacatc atgggctttg ttcagcttcg cagaaagcta      360
gagatgttca cctacatgcg gttcaacgct gaattcacct ttgtcgcgac tttgagtgac      420
ggaacaactc cccatataat gttgcaatac atgtatgtgc cccctggagc tcccaaacct      480
caggaaagag attcattcca atggcagact gcaaccaacc catccgtgtt tgcgaaaatg      540
agtgaccctc ctccgcaagt ttcagtacct ttcatgtctc ctgctagcgc ctaccagtgg      600 tttttatgatg ggtacccaac atttgatgat agaccacaga cctctaatcg tccctacgga     660
caatgcccca ataacatgtt gggcacattc gcggtgcgca ttgttagcaa gacgcctgcg      720
gagagagact tgcgcgtccg tgtttacatg aaactgaagc atgtgcgagc atgggtaccg      780
cgacccataa ggtcacagcc ttacgtcttg aagaactacc ccaactatga tggaacccaa      840
atcgtgccca gtgccaaaga tcgagaagac ataaagaaca ca                        882

<210> SEQ ID NO 25
<211> LENGTH: 915
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 25
ggtgatgcaa tcgctgatgc tatacaaaac acagttacat ctactataca gagagtcaca       60
accaacactg ttgggcaaga tgcaacagct gctaacacag cacccagctc tcatagtttg      120
aacactggcc tagtccccgc gcttcaagct gctgagacag agcttcatc cacagccacg       180 gatgggaatt tgattgagac tagatgtgtt gtaaactcca atggtacacg tgaaacccac      240
```

```
attgagcatt tcttctctag gtcagggctg gtgggagtta tggaggtaga tgatacgggt     300
actagtggca agggattctc aaactgggac attgacatca tggcgtttgt gcaactgcgc     360
cgtaaactcg aggcatttac atatatgcgg ttcgacgcag agtttacctt tgtcaccaat     420
ttggagaacg ggctcacgaa taatagtgtg atacagtaca tgtatgtacc acctggagcg     480
cctaaacccg atgcccggga atcattccag tggcaaactg caaccaatcc gtcagtcttt     540
caaaaaatgg acagtccgcc acctcaagtt tcagtaccct tcatgtcacc agccagtgcc     600
tatcaatggt tctatgacgg ttaccccacc tttgggcccc actcggagac atctaatcta     660
tcttacgggc aatgtcccaa taatatgctg gaacattct  cggccagggt tgttagcaag     720
caaatcacca atcagaaatt ccagatccgt atttatctac ggctgaagag ggtgagggcg     780
tggatcccca gacctttgag atcgcagccg tacatttaca gaaactaccc cacctatggt     840
actaccatcc aatacctggc caaagatagg cgcaagatca ctgaaactga ttataatgct     900
gaacagcgca cgcat                                                       915

<210> SEQ ID NO 26
<211> LENGTH: 885
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 26
ggcagaccaa ttgcagatat aatagaagga gcagtagctc aaactaccac cagagcacta      60
agtggaccaa ttcagccagt gacagcggcc aacacctctc ccagttcaca tcggcttggt     120
acggggcaag tgccagcttt gcaagcagca gaaacgggag ccacctcgaa tgcgaccgac     180
gagagtttga ttgaaaccag gtgtgtggtc aacagacatg gagtcatgga aactagcatt     240
gaacacttct tttcacgctc aggcttggca ggaattttga taattgagga ctccggtact     300
tccacgaaag gctacgccac ttgggaaatc gatgttatgg gatttgtcca gctgaggcgt     360
aaactagaga tgttcacata catgcgattt gatgcagagt tcacctttat cacagcagaa     420
aggaatggca acaccagccc aatacccatc cagtacatgt atgtcccacc cggagcccca     480
gtccctactg gtagggagac attccaatgg caaacagcga ccaatccatc cgtgatctca     540
aagatgactg atccaccagc ccaggtgtct gtaccattta tgagcccagc cagtacttat     600
caatggttct acgatggcta ccccacgttc ggagaagttc cagtgactac gaacttgaac     660
tatggacagt gcccaaacaa caaaatgggc actttctgca tccgcatggt ctcaggtgta     720
tctacaggca aggacgtcac tgtgcgcatt ttcatgaagt tgaagcatgt gcgcgcctgg     780
gtgccaaggc ccatcaggag ccagccttac ttgttaaaga attatcccaa ctttgacaag     840
tcaaatattg tagacgcatc atcgaacagg acatatacca ccact                     885

<210> SEQ ID NO 27
<211> LENGTH: 915
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 27
aatgacccca tttcaaatgc aatagaaaat gctgtgagca cactcgctga caccacgata      60
tcacgtgtta cagcggccaa cactgctgct agctcccatt cccttggtac tggacgcgtg     120
```

```
ccggcgttgc aggctgcgga gacaggggca agttccaacg ctagcgatga gaacctgatt      180
gaaactcgtt gtgtgatgaa tagaaatgga gttaacgaag caagtgtaga acacttctac      240
tcccgtgcag ggctagtagg agttgtggag gtgaaagact caggcactag tcaggacggg      300
tacacggtgt ggcccataga tgtgatgggc tttgtgcaac agcggcgcaa gttagagcta      360
tctacttaca tgcgctttga cgctgaattt acctttgtgt ccaatctcaa tgacagcaca      420
acacccggca tgctattgca gtacatgtac gtgccgccgg gtgcgcccaa accagacggt      480
aggaagtcat atcaatggca aacagccacc aacccttcaa tattcgcaaa gttgagtgac      540
ccaccgcccc aagtgtctgt cccattcatg tcaccggcgt cagcctacca gtggttctac      600
gatggttacc ccacgtttgg cgaacacaag caagctacta atttacaata cggtcagtgc      660
cctaacaaca tgatggggca ttttgctatt cggacagtta gtgaatccac caccgggaaa      720
aatgtccatg tccgggtgta catgagaatt aagcacgtaa gagcatgggt gcccagacct      780
ttcagatccc aagcttacat ggtcaaaaac tacccgacat acagccaaac aatatccaat      840
actgcagccg atcgtgcgag cataaccact acggactatg agggtggcgt accagcaaac      900
ccgcagagaa cttttt                                                      915

<210> SEQ ID NO 28
<211> LENGTH: 888
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 28
ggagacgaaa tactcgacct aatcgagagt gctgtacaga ataccactaa agccattacc       60
agctcaatcg acaccaaaac tggtgctaac actcaagcta gccaacatcg tataggcttg      120
ggggaggttc ccgctcttca agctgctgag acaggatcgt cttcgctcgt ttcggacaag      180
aacatgatag aaacaaggtg tgtcgtaaac aaacacagca cagaggaaac cagcattaca      240
aacttctact ccagggcggg cctagtgggg gttgtgaaca tgccagtaca aggaaccagc      300
aacacaaagg gtttcgcaaa gtgggggata gatataatgg gctttgtgca gatgaggcgc      360
aaacttgagc tcatgacata catgagattc tccgccgagt ttacgttcgt acccagcact      420
cctgggggag agactactaa cctttatactg caatacatgt atgcacctcc cggagctccg      480
ctgccaacca ggcgggattc atacgaatgg caaacatcca ctaaccctc tattatcagc      540 aagatggcgg acccccacgc tcaggtatcg gttccattcc tttctcctgc atcagcatat      600
cagtggttct atgatggcta ccccacattt gggaaacacc caatagatca ggacttccaa      660
tatggcatgt gcccaaacaa catgatgggc acattctgtg tgcgcatgat cggtggggc       720 aaaccgaccc aatcagttac catacgtata tacatgagat taaagcatat ccgtgcatgg      780
gtgccccggc cactgaggag tcagaattac actatgagga attacccgaa ctacaacggg      840
ggcgcaataa aatgtacatc aaaaagcaga gctaccataa caaccttag                  888

<210> SEQ ID NO 29
<211> LENGTH: 882
<212> TYPE: DNA
<213> ORGANISM: Artificial Sequence
<220> FEATURE:
<223> OTHER INFORMATION: Description of Artificial Sequence; Note =
      synthetic construct
```

-continued

```
<400> SEQUENCE: 29
ggagattcca ttgaagacat aataagcaac actgtcaccc gtacactgca acaaatcagt      60
gccccatcac acgacactac agcagccaac acctcagtga gtaatcataa aattggtacg     120
ggggatgtcc cagctctcca agctgcagag actggcgcta cttccaatgc ctcagacgag     180
aacatgattg agacacgatg tgtgttaaat cgcaatgggg ttgtggaaac tagtttggac     240
catttctttt caagagcagg ccttgtggga gtgatcaatg tgcaagatgg cggcactcag     300
aagggttttg aagtgtggga catagatgtc atggggtttg ttcaactcag gaggaagttg     360
gagatgttca cgtacatgag gttcaacgcc gagttcacat tcgtatccac actcgcggat     420
ggcacaactc ccagagtgat gttgcagtac atgtacgttc cacctggtgc ccccaaacct     480
caggagagag attcgtttca gtggcaaact gcaaccaacc catcagtatt ttgcaaaatg     540
agtgaccctc ctccacaggt ttccgttcct tcatgtcac cagctagtgc ctaccaatgg      600
ttctacgatg ggtacccaac attcgatgat cgaccggcca cctcaaacca cccgtacggt     660
cagtgcccca ataacatgat gggcacattc gcagtgcggt ttgtcagcaa gaccccagcc     720
acacgggatc tgcgtgtcag agtgtacatg cgcctgaaac acgtgcgcgc atgggtaccg     780
agacctatcc gatctcaacc ctatattttg aaaaactacc caaattatga tggcacaaag     840
ataacgtcga catctaagga taggcaaagc atcaaaacaa ca                        882

<210> SEQ ID NO 30
<211> LENGTH: 894
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 30
ggcgaccccg tggaggacat catccacgac gctttgagca gcactgtgcg gcgggccata      60
actagtggtc aagatgtcaa cacagcggcc ggtaccgctc ctagctctca caggttggag     120
actggtcgtg ttcccgccct acaagcagca gaaactggag ccacttctaa cgctacagat     180
gagaacatga tagaaacgcg gtgtgtcatg aacagaaatg gagtgttgga ggcgactata     240
agtcatttct tctcacgctc aggtttggtg ggtgttgtca atctaactga cggaggcacc     300
gatacaacgg gatatgcagt gtgggacatt gacatcatgg gttttgtgca actgcggcgg     360
aaatgtgaga tgttcacata catgagattc aacgctgagt tcacattcgt cactacaaca     420
gaaaatggcg aggcaaggcc atttatgtta cagtatatgt atgtacctcc aggtgcccct     480
aagccaacgg gtagagatgc ttttcagtgg caaacagcga caaatccatc cgttttcgtt     540
aagctcacag atccacctgc tcaggtatca gtccccttca tgtcacctgc tagtgcctac     600
caatggttct atgacgggta tccaacattt ggacaacacc cggaaacatc taatacaaca     660
tatggacagt gccctaacaa catgatgggg acctttgctg tgagagtagt gagtagagtg     720
gctagccagc tcaaactaca gacacgagtg tatatgaagc ttaagcatgt gagagcatgg     780
atccctaggc caataagatc ccagccttac ctcctaaaga atttccaaa ttatgatagt      840 agtaagatca catacagcgc aagagatcgt gccagcataa acaagctaa tatg            894

<210> SEQ ID NO 31
<211> LENGTH: 912
<212> TYPE: DNA
<213> ORGANISM: Artificial Sequence
<220> FEATURE:
```

<223> OTHER INFORMATION: Description of Artificial Sequence; Note = synthetic construct

<400> SEQUENCE: 31

| | | | | | |
|---|---|---|---|---|---|
| gggccaatag | aagaaatcat | ctcaactgtt | gccagtaacg | cgttggcgct | cagtcaaccc | 60 |
| aagccagtgg | acaactctgt | acaaaacacc | caacaaagtg | ctccagtgca | tagccaggag | 120 |
| gtgccagcat | tgaccgcagt | ggagacaggg | gcgacaagtg | atgtggttcc | atctgaccta | 180 |
| attcagacta | gacacgtatt | gaatgttaaa | tccaggtctg | aatccaccat | cgagtcattt | 240 |
| tttgcaagag | ctgcatgtgt | aaccattatg | caggtggaca | atttcaacgc | aacctctgtg | 300 |
| gaagacaaaa | gaaagttgtt | tgctaaatgg | gcaatcacct | acactgatac | cgtccagctg | 360 |
| agacggaaat | tagagttttt | cacttattct | agatttgact | tagagatgac | ttttgtgcta | 420 |
| actgagagat | actactccca | aagctcaggg | catgctagat | ctcaggtgta | ccaaattatg | 480 |
| tatgttccac | caggggcacc | cacgcctagt | gcatgggacg | actacacatg | gcaaacatcc | 540 |
| tccaacccat | ccatttctt | taccaccggc | aatgcaccac | cgcgcatttc | aattccattt | 600 |
| gttggaatcg | ccaatgcata | ctcacacttt | tatgatggct | ttagtagagt | acctttggag | 660 |
| ggagaaacaa | cagacacagg | agacgcttac | tacgggctca | cttcaataaa | cgattttggt | 720 |
| acacttgcag | tcagggtagt | taatgactac | aacccagcca | gggtggagac | aaggattaga | 780 |
| gtatacatga | agcccaaaca | tgtgagagtc | tggtgcccgc | gacctccaag | agcggtaagc | 840 |
| tacagaggac | ctggagtcga | cctcctatca | acatcagtaa | cacctttatc | caaacatgac | 900 |
| ctagcgacat | ac | | | | | 912 |

<210> SEQ ID NO 32
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 32

| | | | | | |
|---|---|---|---|---|---|
| ggagatacag | tgagtgatat | gatcgaaaat | tccatcaacc | gaattaccag | tgcaatttcc | 60 |
| actacccaga | cacaccagac | agcagctgac | actagagtta | gtacacacag | gttaggcacg | 120 |
| ggggaggtgc | cacctttaca | agcagcagag | acaggtgcca | cctccaacgc | aaccgacgag | 180 |
| aacatgattg | aaacacgctg | tgtcgtcaac | aggcacgggg | tgagcgagac | cagcgtggaa | 240 |
| tacttcttct | ctcgctctgg | tttggcagga | atagtcatcg | tggaggatgc | aactgccact | 300 |
| aataagggtt | atgccacatg | ggagattgat | gtcatggggt | tcgcgcaact | gcgtcgcaag | 360 |
| ctggagatct | tcacatacat | gcgcttcgat | gcagagttca | cttttgtggc | aacagaacgc | 420 |
| aatgggagca | ccagcccggt | catgatgcag | tacatgttcg | tgcccctgg | cgcccctgtt | 480 |
| ccaacaggga | gagatacctt | ccaatggcaa | tctgctacta | cccttcagt | gctagtaaaa | 540 |
| atgacggatc | caccggccca | agttgccatc | ccctttatgt | ctccagctag | tgcataccaa | 600 |
| tggttctatg | atggatatcc | tacctttgga | gaaagaccag | ttacaaccaa | catgaattat | 660 |
| ggacagtgtc | ccaacaacaa | aatgggaact | ttttgtatac | gcactgtctc | cggtgaagcg | 720 |
| tcagggaaaa | acatcactat | acgtattttt | atgaggttga | agcatgtaag | agcgtgggtg | 780 |
| cctcgcccaa | ttagaagcca | gctatatctg | cttaaaaatt | accccaactt | tgataacact | 840 |
| aagatcctca | cgcctcccca | caacagagct | tctatcacat | caaacaca | | 888 |

<210> SEQ ID NO 33
<211> LENGTH: 927
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 33

```
gggttggaag atctaataca acaagttgcg tctaacgcat tacaattgtc ccagccaaca      60
agaccggcac tcccaccagc cgagcagagt gtccccaaca ctaaccaaac aactccagaa     120
cactccaagg aagtcccagc gttaacggca gttgaaactg gcgccacgaa tcctctagag     180
cctggcgaca cagttcagac tagacatgtg atacaaacta gaagtagaag tgaaagtaca    240
gtggagtctt tctttgcgcg aggtgcatgt gtaaccatta tgggagtgga caactataat     300
gagacattga aggagacca gaagtctact ctatttacaa cctggaacat cacctacact     360
gacacagtcc agctacggag aaaactggaa atgttcactt actccaggtt tgacatcgag     420
tttacttttg tggtgactga acgctactac tcatcaaaca gtgggcatgc tctgaaccaa     480
gtgtaccaaa ttatgtatgt accacctgga gcaccagtgc caagaaatg ggatgattac      540
acctggcaaa cctcttcaaa cccgtccata ttctacactt atgggtcagc accacccagg     600
atatccatac cctttgtggg tatagcaaac gcttactccc acttctatga tgggtatgcg     660
acagtgccct tgaaaactga caccacagac tcaggagcag cctactatgg agcagtatcc     720
ataaacgact tcggactgct tgcagttcgc gtcgtcaatg aacataatcc agtcagagta     780
tcatccaaaa ttagagtgta tatgaaacca aaacatgtca gggtatggtg tcccagacct     840
ccaagggctg tagagtatta tggaccagga gtggactaca aggcaaacac tttaacaccg     900
ttgccaataa agaatttgac tacttat                                         927
```

<210> SEQ ID NO 34
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 34

```
ggtgacaaag tggcagacat gattgagacc gcagtggaga agaccgtgtc ctcactaact      60
tccctattc aaaccccac agccgccaac acaaacgtga gtaatcatcg aattgagctg       120
ggggaagtcc cggctttgca agctgctgaa accggcgcga cgtctcttgt gtctgatgaa     180
gacttgatag agactcgttg tgtagtgaat agccatagta cagaggaaac tacagtgggg    240
tacttctttt caagagcggg gttggtggga gtgattgacc tcccattaca gggaacagtc     300
cacacaggag gattcgcctc gtgggatatt gatgtaatgg gatatgttca gatgagaagg    360
aaacttgagc tgttcacata tgcccgcttc gatgcggagt ttaccttcat agcttccacc    420
ccagatggcg aggtgaagcc agtgttctta cagtacatgt tcgtcccccc tggtgcacca    480
aaaccaacag ggcgcaacac ctacgaatgg caaactgcaa caaacccttc tgtgttggtc     540
aagagcacag atcctccagc acaagtctct gtaccgttca tgtcaccagc cagcgcatat    600
cagtggttct atgacgggta cccaacctttt ggaaagcacc tgcctgctga tgactttcag    660
tacggtatga ccccaaataa catgatggga tcgttctgtg ccaggatagt ggggaagga     720
gcgcctagtg tacacttggt tatccgtatc tacatgcgca tgaaacacgt gcgggtgtgg    780
```

| | |
|---|---|
| attccacgac ctatgcgcag ccagccatac gttgcgaaga attaccctaa ctacaagggt | 840 |
| tctgagatca agtgcgcatc atctagtcgt aagtcaatca ccacatta | 888 |

<210> SEQ ID NO 35
<211> LENGTH: 912
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 35

| | |
|---|---|
| gggccaatag aggagatcat ctcgaccgtc gccagcaatg cacttgccct cagtcagcct | 60 |
| aaaccggtgg ataattctgt acaaaacacc caacagagcg cgcccgtgca cagccaagag | 120 |
| gttccagcat taacagcagt agagactgga gcaacaagtg atgtggtgcc agctgatcta | 180 |
| gtgcaaacca ggcatgtagt gaatgtcaag tccagatctg agtccactat cgagtcgttc | 240 |
| tttgcaagag ctgcctgcgt gactattatg caggttgata actttaatgc caccaccacg | 300 |
| gaggacaaga ggaagttatt tgccaaatgg gccatcacat acacagacac agtacaattg | 360 |
| aggaggaaat tggaattttt cacgtactcc aggttcgatc ttgagatgac tttcgtgcta | 420 |
| actgaaagat actattctca gagctcggga cacgctagat cgcaggtgta tcaaatcatg | 480 |
| tacgtccctc caggagcacc aacaccaaat gcatgggatg attacacgtg gcagacgtct | 540 |
| tctaacccat caatttttctt caccactggt aacgcacccc cacgggtttc aatcccattt | 600 |
| gtgggcattg caaatgctta ctcacacttt tatgatggct tcagcagggt accttttggaa | 660 |
| ggagagacca ctgactcagg tgacgcttat tatggcctca cttctatcaa tgactttgga | 720 |
| acacttgcag taagagtggt caatgactac aacccagcga gagtggagac aaggatcaga | 780 |
| gtctacatga aacctaagca tgtgagagtg tggtgtccac gaccccctag ggctgtgagc | 840 |
| tacagaggac ccggtgtgga cctactgtcc acctcagtga cgcccctatc taagcatgaa | 900 |
| ttgacaacgt ac | 912 |

<210> SEQ ID NO 36
<211> LENGTH: 918
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 36

| | |
|---|---|
| ggcattgaag acttgatcca acaggttgca tcgaatgcgc tgcaaatctc acagccgacg | 60 |
| cgtccggcac tgccctctac agaaagtctt cccaacacac aacaatcggc accttcgcat | 120 |
| tctcaagagg tcccggcgct gacagcagtt gagacaggcg cgacaaatcc attggagccg | 180 |
| tctgacacgt tacaaacaag gcatgttatc cagactagat ccaggtcaga gtccacaata | 240 |
| gagtccttct tcgcgcgtgg tgcatgtgtg acaatcatga cagtggaaaa ttttaacgcg | 300 |
| actgaggcgc agacaagaa aaagttgttc gccacttgga atattacata cacagacaca | 360 |
| gtgcagctca gaaggaagtt ggagatgttc acttactctc gatttgacat tgaatttacc | 420 |
| tttgtcacca cagaaaggta ctacgccagt aactcaggcc atgcgcgtaa tcaggtttac | 480 |
| caactcatgt atgtaccccc aggagcccct gtgccacaac aatgggatga ttacacgtgg | 540 |
| caaacttcct ccaaccccatc ggtgttttac acatacggtg acgctccagc gcgcatttcc | 600 |
| ataccatttg tagggatagc taatgcctat tcccactttt atgacggcta tgcagtggtg | 660 |

```
ccattgaaag attccaccca ggatgctggt gctgcctatt atggtgcaac ctcaattaat      720
gattttggaa tgttggcggt gagagtagtc aacgaattca acccagccag aatcacatct      780
aaattgagag tgtacatgaa accaaagcat gttagggtgt ggtgtcctag accaccaagg      840
gtggtgccgt acttcggacc cggtgttgat tataaggata gtttgacacc gctttctaca      900
aaagcactca acacttat                                                   918
```

<210> SEQ ID NO 37
<211> LENGTH: 927
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 37

```
ggcttggaag acctcatcca acaagtggcc acgaatgcat tgagtctgtc gcagcccaca       60
agacccgcac ttccaccagc agaacaaagt gtgccaaaca ccagtcagac caccccagaa      120
cattcaaagg aagtacccgc actcactgca gtggagaccg gtgcaaccaa cccattggaa      180
ccaggtgaca cagtgcaaac tagacatgtt gttcaaacaa gatcaaggag cgaaagtacg      240
gtggaatctt tctttgcaag aggggcgtgt gtcacgatta tgggagttga caattacaat      300
gaaagcttga ccagtagtca aaatccacc ctattcgcca cttggaatat tacatacact      360
gatacagtac agttgaggag aaaattggaa atgttcacct actccagatt tgacattgaa      420
tttaccttcg tagtaactga acgttactac tcgtcaaaca gtggccatgc cttgaatcag      480
gtgtatcaaa tcatgtatgt gccaccaggc gctccaattc ctaagaagtg ggatgattat      540
acctggcaaa catcatcaaa ccctcaata ttctacacct atggaacagc accacccaga      600
atttcgatcc cttttgtggg cattacaaac gcgtactcac atttttatga cggatatgcg      660
actgtaccac tcaagacaga cactacggat ccgggggcgg ccttctatgg agcagtttcc      720
atcaatgact ttggttttgtt ggcggtgcga gttgtcaacg agcacaaccc ggtaagagtg      780
tcttcaaaga taagagtgta catgaagcct aaacatgtca gagtgtggtg cccacgacca      840
ccacgtgccg tggagtacta cggaccaggg gtagattaca aggcaaacac attgacacct      900
ctccctacca agaacttaac tacttat                                         927
```

<210> SEQ ID NO 38
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 38

```
gtattgatg atatcataga taatgttgta accaatgctt tgaaggtgtc catgccacaa       60 ttcaagata cgcaatctag tggaccagtt aactcaaaag aagtacctgc attaacagct      120 ttgaaacag gggctactag tcaagttgac ccatcagacc taatagaaac tagacatgtt      180 ttaataacc gcctcagatc tgagtgcaca atagaatcat tctttgggag gtcagcatgt      240 tggccataa ttgggttatc taaccaaaaa cccaccagtg acaatgcagc caagctcttt      300 ctacatgga agattagtta tcttgatatg tatcaattga gaagaaaatt ggaattcttc      360 catactcca gatttgatct tgagttaacc tttgtaattt cagaaagatt cttcacctca      420
```

```
cttcagctg ctgcaagaga ttatgtatac cagatcatgt acattccccc aggagcccct      480 tccctcagg tatgggatga ttacacatgg caatcatcca caaaccccct aatattctac      540 ccacaggaa atgcatgccc tagagtgtcc atccctttg ttgggatcgg tgcagcatac       600 ctcacttct atgatggatt ctctttagta ccttttcaata ccatcgatgc tggtgcttca     660 acaggtacg ggtacaccac cataaatgat tttgggacta tggcaatcag gatagttaat     720 aatacgacc cagtcacaat tgatgcaaaa gtcagggttt acatgaaacc aaagcatatt     780 aggtgtggt gccccagacc tccacgggca gtagcataca atgggccaac agtgaatttt    840
atgaaaaacc cccatgtaat gacagcagtt gctgatatta gaacttat                 888

<210> SEQ ID NO 39
<211> LENGTH: 909
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 39
ggtatcgaag atcttatcac cgaagttgca agcaacgctc tgaagttgtc acaaccaaaa      60
cccagcacac aacagagttt accaaacact agtagctcag aaccaactca ctctcaggaa     120
gcgccggcat tgaccgcagt agaaacagga gcaactagta gcgtagtacc agctgatctg     180
gtccagacgc ggcatgtgat acaaacacgt agccgaagtg agtctacagt tgagtcattc     240
tttgctcggg gggcgtgtgt aacaatcatg tcagtggaaa attacaatga aaccgctatc     300
gcagagtcca aattatttac caagtggaac attacctaca cagacacagt ccagttgaga     360
agaaaactag atatgttcac atactccaga ttttgatattg agttcacatt tgtggtgact    420
gagcgttacc actccgcaaa ctcaggtcat gcactaaatc aagtttacca gatcatgtat    480
gttcctccag gtgcaccagt gccacaaaga tgggacgact acacatggca acgtcatcc     540 aaccccctcag tcttttatac ctatggtaca gcaccagcca gaatatcgat tccatatgta    600
ggcatagcca atgcctactc gcattttttat gatggcttcg ccaaagtgcc cattgaaggc   660
gagacgtcag atccaggtga tgcatactat ggtgcaacgt ccatcaatga tttcggcatc   720
ttagccatac gtgtggtcaa cgaacacaat ccagtgcaag tttcttccaa gattagagtg   780
tacatgaaac ctaaacatgt gcgcgttttgg tgtcccagac cacctagagc tgttccatac    840
tttggccccg gggttgatta taaaggtgac gccctcacac cactatcacg caaggattta    900
accacctat                                                             909

<210> SEQ ID NO 40
<211> LENGTH: 888
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 40
gggattgagg atacaatcga aaaagtggtt ggtgatgctc taagggtctc aatgccacaa      60
gttgccaaca cccagccatc aggacccgta aattctaagg aagttccagc actgacagca    120
gtggaaacag gtgcaaccag tcaagtcacc cctgaagatt tgatcgaaac caggcatgtt    180
attaacaata gactaagatc tgagtgcact gtggaggcct ctttggaag gtctgcatgt    240 attgccatcc ttggtgtggt aaacaaaaag ccagacacca caaatgccaa agacctcttt    300
```

```
gcaacatgga ggatcactta cctgcaaact tatcaactga ggaggaaact cgaactcttc    360
acgtattcta gatttgattt ggaattaacg tttgtcatta cagaaagata cttttcaggg    420
acagcagcca caaccagaga ttatgtttac caaataatgt atgtaccacc aggagccccc    480
ataccaaata cctgggacga ctacacctgg cagtcatcta ccaaccccte tgtcttctac    540 accacaggca atgccagccc acgcatgtct atacccttg ttggtattgg tgccgcctat    600
gctcactttt atgacgggtt cagtgtggta ccattcaatc aaatagatgc aggagcatcc    660
aacaaatatg gctactcatc aatcaaagac tttggtacat tggcagttag aattgttaat    720
gagtttgatc cagtgacaat agaggctaaa gtcagagtgt acatgaaacc caaacatgtc    780
agggtgtggt gtccaagacc acctcgtgca gtaccatatc aaaactcatc agttgatttc    840
gcccaaaacg cagtagcaat gaaccaagta gccacaatta ggacgtat                888
```

<210> SEQ ID NO 41
<211> LENGTH: 915
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 41

```
ggtatcgaag ataccattga cactgtcatt aacaatgccc tacaactatc tcaaccacag     60
ccaaataagc agttgacagc tcagtctacc ccctccacaa gtggagtaaa ctcccaggag    120
gttccagctc tgaccgctgt ggaaaccggt gcctcgggac aagcagtgcc cagtgatgtg    180
attgagacca gacacgtggt taattataag acccgatctg aatctactct tgagtctttc    240
tttggaaggt cagcttgtgt caccataatt gaggtcgaga acttcaatgc cactagtgaa    300
gcagacaaga ggaaacagtt caccacttgg ccaatcacat acaccaatac cgtgcaattg    360
cgcaggaaac tagaattctt cacttactcc aggtttgacc tagagatgac cttgtagtg    420 acagaaagat attatgccag caacacaggt cacgccagaa accaagtgta tcaaataatg    480
tacattcctc ctggtgcacc acaacccaca gcatgggatg attacacgtg gcaaagctct    540
tcgaatccgt cagtctttta cacttatggg agtgctccac caggatgtc tataccgtat    600 gtcggtatcg caaatgcata ctctcttttt tatgatgggt ttgcacgagt accactgaag    660
gacgaaacag cggactcagg tgatactttt tacgggctag tcaccatcaa tgattttgga    720
accttagcaa taagagtagt gaatgaattt aacccagcta ggattacatc aaaaattaga    780
gtgtatatga aaccaaagca tgtaagatgc tggtgcccta gaccaccacg tgcagtgcca    840
taccgtggtg aaggagtaga ttttaattca agttcaatca caccactaac agcagtcgca    900
aacatcaaca cattc                                                    915
```

<210> SEQ ID NO 42
<211> LENGTH: 852
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 42

```
agcccagtgg aggaatccat tgagagaagc attggcagag ttgctgacac cattggtagt     60
ggaccatcca attcggaggc aataccggca ctcacagcag tagaaacagg acacacatca    120
```

-continued

| | |
|---|---|
| caggttacac ctagtgacac gatgcaaaca agacatgtgc acaactacca ttcaaggtcc | 180 |
| gaatccagcg tagagaactt cctggcacgc tcggcttgtg tgttttatac aacatacacc | 240 |
| aacggtaaaa aaaaaaatgc cgccaaagag aagaagtttg caacgtggaa agtgagtgtt | 300 |
| agacaagccg cccaactaag aagaaagcta gagttattca catacttacg ctgtgacatc | 360 |
| gaattaacat tcgtcatcac cagtgcacaa gatccatcga ccgctaccaa cttggatgtg | 420 |
| ccagtgttga cccatcaaat aatgtacgtc ccacctggtg gtccagtccc tgaaaccgtg | 480 |
| gacgattaca actggcaaac atctacaaat cccagccttt tttggactga agggaatgca | 540 |
| cctccacgca tgtcaattcc attcatgagc ataggcaatg cctatagtat gttctatgat | 600 |
| ggttggtccg agtttaggca tgacggtgtg tacggcctga ataccettaa caatatgggc | 660 |
| acaatatatg ctaggcacgt caacgctgac aacccaggta gcatcaccag cacagtgaga | 720 |
| atatacttca aacccaaaca tgtcaaggca tggattcctc gcccgcctcg tttggcacag | 780 |
| tatcttaaag ccaataatgt gaattttgag atcaccgatg tgacagaaaa gagagatagt | 840 |
| ctcacgacca cg | 852 |

<210> SEQ ID NO 43
<211> LENGTH: 846
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 43

| | |
|---|---|
| agcccagtgg agggcgccat agagagagcc attgcacggg tcgctgacac tatgccaagt | 60 |
| ggcccaacca attcagaagc agtgcctgcc ctgacacag tggaaacggg ccacacctcc | 120 |
| caagtcgtcc ccagtgataa catgcaaacc aggcacgtga agaagtacca ttcacgctcc | 180 |
| gaaaccagcg tcgagaactt tctgtgtagg tctgcatgtg tatattttac cacatataag | 240 |
| aaccagacag gggcgaaaaa tagatttgct tcttgggtaa tcaccacaag acaagtggcc | 300 |
| cagctcagga gaaaactaga aatgtttacg tacttgcgtt tcgacattga actcacctt | 360 |
| gtcattacaa gtgcgcaaga ccaatccact atttcccaag acgcccctgt gcagacacat | 420 |
| cagataatgt acgtgccacc gggaggccca gtgccaacca agttgacga gtatgtgtgg | 480 |
| caaacatcca ccaaccccag cgtctttttgg accgagggta acgctccacc acgtatgtca | 540 |
| gttccctta tgagtatcgg taatgctat agcacatttt atgacgggtg gtctgatttt | 600 |
| tcaaacaaag gaatatatgg gttgaacacc ttgaacaaca tgggaacatt gtacatccgc | 660 |
| cacgttaacg ggcccaaccc agtaccaatt accagcacag tgaggatata ctttaagccc | 720 |
| aagcatgtta aggcctgggt gcctaggcct ccaaggcttt gccagtacaa aacgtttagg | 780 |
| acagtcaact ttacagtgac tggagtgacc gagagtaggg caaatataac caccatgaat | 840 |
| actaca | 846 |

<210> SEQ ID NO 44
<211> LENGTH: 852
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 44

| | |
|---|---|
| ggtgatgtgc agaatgctgt cgaaggggct atggtcaggg tggcagatac agtgcaaact | 60 |

| | |
|---|---:|
| tcagccacaa actcagagag ggtgcctaac ttgacagcag tagaaactgg tcacacttcg | 120 |
| caggtagtac ctggtgatac catgcagact agacatgtga tcaacaatca cgtgaggtca | 180 |
| gaatctacaa ttgagaactt ccttgccaga tcagcgtgtg ttttcttcct agagtacaag | 240 |
| acagggacca agaggattc caatagcttc aacaattggg tgattacaac caggcgagtg | 300 |
| gctcaactac gtagaaaact ggaaatgttt acttacctac ggtttgacat ggaaatcacc | 360 |
| gtggtcatta caagctcgca agatcagtct acatcacaaa accagaatgc accagtgcta | 420 |
| acacaccaga taatgtatgt accaccaggg ggacccatac ccataagcgt ggatgattac | 480 |
| agctggcaaa catccaccaa ccccagtatc ttttggaccg aagggaacgc tccggcacgc | 540 |
| atgtcaattc catttattag cataggcaat gcgtatagta atttctacga tgggtggtct | 600 |
| cacttctccc agactggcgt gtatggcttc actactctga caacatggg tcaattgttc | 660 |
| ttccggcacg taaacaagcc caacccagcc gctattacaa gtgtggcgcg catttacttc | 720 |
| aaaccgaaac atgtacgcgc ttgggtgcct agaccaccgc gcttgtgtcc atacatcaat | 780 |
| agcacgaatg tcaactttga acccaagcca gtgactgaag tacgtaccaa cataataaca | 840 |
| acgggtgcct tc | 852 |

<210> SEQ ID NO 45
<211> LENGTH: 882
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 45

| | |
|---|---:|
| ggagatgagg tgaagcatga acccacagtg gccaacacaa cagcaagtgg accatcaaat | 60 |
| tcacaacaag taccggcact cacagcagtg gagactgggc acacctcaca ggtggttcca | 120 |
| agcgatacca tacaaaccag acatgttcac aattaccata gtagaactga atccaccctg | 180 |
| gagaacttcc tcggaagatc agcatgcgtg cacattgact cgtataagac caagggagtg | 240 |
| accggcgaga gcacccggta cgcatcatgg gagatcacca ctcgcgagat ggtgcagctg | 300 |
| cggaggaagt gtgaactctt cacctacatg cgatatgatc tagaaatcac gtttgtgatt | 360 |
| acaagtcgcc aggagcaagg ggccaaactg tcgcagaaca tgccagtatt aacacatcag | 420 |
| atcatgtatg tcccaccggg cgggcctata ccaaccagca acgagagtta cgcttggcaa | 480 |
| acgtcaacga acccaagcgt gttttggaca gaaggaagct cgccaccacg aatgtcaata | 540 |
| ccgtttgtta gcataggaaa cgcatacagc aatttctatg atgggtggtc gcacttctca | 600 |
| caaaacggtg cgtatggtta cacggcacta acaagatgg gtaggatatt cgtgcgccat | 660 |
| gtaaacaaag agacaccact gcaagtcata agcacaatac ggatgtatat gaagcccaaa | 720 |
| cacgtgcggg cttgggtgcc aagaccacca cgcctgtgtc catacctgcg ggcgggtgat | 780 |
| ataaactttg aagtgactga tgttacagaa aaacgaaata acatcaatta tgtcccaacc | 840 |
| ccatcccaca gcagcagtgt gcacatgcgc ttgaacaacc at | 882 |

<210> SEQ ID NO 46
<211> LENGTH: 879
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 46

```
ggggacgtcg aagaggcaat tgatagggca gttgcgaggg tggctgacac aatgccaacc    60
ggtccacgaa acactgagag cgtgcctgcc ctgacagcag tagagacagg ccacacctca   120
caggtcgttc ctggtgacac aatgcagacg aggcatgtta agaactatca ctccaggaca   180
gagtcatcaa ttgaaaactt cctgtgcagg gctgcgtgcg tgtatataac aacatacaaa   240
tcagctggtg aacacccac agagcgatat gcaagttgga ggataaacac caggcaaatg    300
gtgcagctca ggaggaaatt tgagctcttc acatacttgc gctttgacat ggaaatcaca   360
tttgtgatca caagcacaca agatcctggg acacaattgg cacaagatat gcctgtacta   420
actcatcagc tcatgtatat cccacctggg ggccctgttc ctaacagtgc cacagatttt   480
gcatggcaat catcaactaa tccaagtata ttttggacgg aaggctgtgc tccagcacga   540
atgtcggtgc cgttcatcag cattggcaat gcctacacca ttttacga tgggtggtcg     600
catttcaccc aagaagggt ttatgggttt aactcactga caacatggg ccacatatat     660
gtgaggcacg tcaatgagca aagcctgggt gtctcgacca gcaccgttcg cgtgtatttt   720
aaacccaaac atgtgcgtgc ttgggtacca agaccaccca gactgtgccc atacactaag   780
agttcaaatg tgaatttcaa accgaccgct gtcactgatg agcgaaagga tatcaacgat   840
gtaggcaccc ttcgaccaac agtgtacact aaccttgtg                          879
```

<210> SEQ ID NO 47
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 47

```
ggagacgtgc aagatgcagt gacaggtgct atagtacgtg tcgctgacac tctcccaaca    60
ggtccctcaa ataatgaagc tatacccaat ttaacagcag tggagactgg ccatacctcg   120
caagtgacac caggcgacac aatgcaaaca cgccatgtgg tgaacatgca caccgctct    180
gagtcgtcca tcgagaattt cctggcacgt tcagcatgcg tgtactacct tgattaccaa   240
acgggagaag ggcccggcga tcagtatttt ggccagtgga ccattaccac gaggagggtt   300
gcgcaattgc gtcgaaagct ggagatgttc acttatctaa gatttgacat ggaaatcaca   360
atcgtgatta ctagttcaca ggatcaatct accatctcga acccagatac accagttttg   420
acgcaccaaa ttatgtatgt accaccagga ggaccaatcc cagcaaaagt cgatgattac   480
agttggcaaa catccacgaa tcccagcgta ttctggactg aagggaatgc gcctgcccgr   540
atatccatcc cattcattag cgttggaaat gcatacagta gcttttatga cgggtggtcg   600
aacttctcac aaaacgggcg gtatggctac aatacccctca caacatggg acaattgttc    660
tttaggcacg ttaacaaacc cagccctaat actgtcacaa gcgtcgcccg catatacttc   720
aagcctaagc acgtgagagc ttggatcccg cgaccaccgc ggttgtgtcc atacataaat   780
gcgggagacg tgaacttcac tccgacacca gtgactgaaa agcgaaagga cctaataacc   840
acg                                                                 843
```

<210> SEQ ID NO 48
<211> LENGTH: 843
<212> TYPE: DNA
<213> ORGANISM: Artificial Sequence
<220> FEATURE:

<223> OTHER INFORMATION: Description of Artificial Sequence; Note = synthetic construct

<400> SEQUENCE: 48

| | |
|---|---|
| ggagatgtgc aggacgcagt ggctggggcc atagtgcgtg tggctaatac tctcccatca | 60 |
| ggcccctcaa acaatgaggc tatacccaac ttaacagccg tagaaactgg acacacctcg | 120 |
| caggtgacac cggtgatac aatgcagacg cgccacgtag tgaacatgca cactcgttct | 180 |
| gagtcgtcaa tcgagaactt cctggcgcgg tcagcatgtg tatactacct cgattaccga | 240 |
| acaggaacgg ggcctggcaa tcaatacttt agccagtgga ctattaccac aagacgagtt | 300 |
| gcgcagctgc gtcgaaaatt ggagatgttc acctatctaa ggttcgacat ggagatcacg | 360 |
| attgtaataa cgagttcaca agatcagcct accgtccgaa acccagacac accggtcttg | 420 |
| acacaccaaa tcatgtatgt gccaccagga gggccaatcc cagcaaaggt cgacgattac | 480 |
| tgttggcaaa catccacaaa ccccagtgtc ttctggactg aagggaacgc accagcccgg | 540 |
| atatccatcc cgttcatcag tgtcgggaat gcatatagta gtttctacga tggatggtca | 600 |
| aatttctcgc aaaatgggcg gtatggctac aacaccctga caacatggg gcaattgttt | 660 |
| ttcaggcatg tcaataaacc cagtcccaac actgtcacaa gtgttgcccg catatacttc | 720 |
| aagcccaaac acgtgaaggc atgggtcccg cgaccaccgc gattgtgccc ttacattaat | 780 |
| gctggagatg taaatttcac ccccacatcg gtcactgaga agcgagcgag cctgataacc | 840 |
| aca | 843 |

<210> SEQ ID NO 49
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 49

| | |
|---|---|
| ggggacgtgc aagatgccgt gactggagcc atagtgcgtg tcgccgacac actgcacacg | 60 |
| ggaccctcga acaacgaagc aatacccaat ttgacggccg tggaaacagg gcatacatcg | 120 |
| caagtgacac caggcgatac aatgcagacg cgtcacgtgg tcaacatgca cacccgttca | 180 |
| gagtcatcaa ttgagaactt cctagctcga tctgcgtgtg tgtattacct cgactatcaa | 240 |
| acagggtcag gacctggcac ccaatacttc ggccagtgga ccatctccac aaggagagtt | 300 |
| gcgcaactgc gccggaagtt ggaaatgttc acctacctaa gatttgacat ggaaataaca | 360 |
| atcgtgatca ccagttcgca agatcactcc accatctcaa atccagatac accaatcatg | 420 |
| acgcaccaaa ttatgtacgt accaccaggg ggtccaatcc cggcgaaggt cgacgactat | 480 |
| agctggcaaa catctacaaa ccctagtgta ttttggacag aagggaacgc acccgcccgc | 540 |
| atatccattc cattcattag tgtcgggaat gcctatagca gcttctacga cggtggtca | 600 |
| aatttctcgc aaaacggccg atatggatac aacactttga acaacatggg acaactattc | 660 |
| ttcagacacg tgaataagcc cagccccaac accttcacaa gtgttgcccg tgtatacttc | 720 |
| aagccaaaac acgtgaaggc gtggattcca cgaccaccgc gattatgtcc atacataaat | 780 |
| gcgggagacg tgaatttcaa accaacaccc gtgaccgaaa agagggcgag cttaatcacc | 840 |
| aca | 843 |

<210> SEQ ID NO 50
<211> LENGTH: 876

<212> TYPE: DNA
<213> ORGANISM: Artificial Sequence
<220> FEATURE:
<223> OTHER INFORMATION: Description of Artificial Sequence; Note = synthetic construct

<400> SEQUENCE: 50

| | | | | | |
|---|---|---|---|---|---|
| ggagactcag | agcacgcagt | ggaaagcgcc | gtatctaggg | tggcagatac | aattatgagt | 60 |
| ggcccgtcaa | actcccaaca | ggtccccgct | cttactgcag | ttgaaactgg | acacacatcg | 120 |
| caagttgttc | caagtgatac | catccaaacc | agacatgtgc | agaatttcca | ctctaggtcc | 180 |
| gagtcgacca | ttgaaaattt | cctgagtagg | tcagcatgtg | tgcatatcgc | caattacaac | 240 |
| gcgaagggcg | ataagacgga | tgtggacagg | tttgacaggt | gggagatcaa | cattcgtgaa | 300 |
| atggtgcaac | tacgtaaaaa | gtgtgagatg | ttcacatatc | tacgctatga | tattgaagtt | 360 |
| acatttgtta | taaccagcaa | acaggatcag | ggccccaaac | taaaccagga | tatgcctgtt | 420 |
| cttacccacc | aaattatgta | cgtaccccca | ggaggttcag | tacctagcac | cgttgagagc | 480 |
| tatgcgtggc | aaacatcaac | aaaccctagc | gtgttttgga | ccgaggggaa | cgctccagct | 540 |
| agaatgtcca | tacctttat | cagcataggg | aacgcttata | gtagcttcta | tgatggatgg | 600 |
| tcacacttta | ctcaaaaagg | ggtctacgga | tacaacacat | aaacaagat | ggggcagcta | 660 |
| tttgtcagac | atgtgaacaa | acagacccc | acgccagtta | ctagtaccat | aagggtttac | 720 |
| ttcaaaccaa | agcacattag | agcttgggtc | cctaggcccc | cgcggttatg | ccctatgtg | 780 |
| aacaagacaa | atgtaaactt | catcaccaca | caggtaacag | aacctacaaa | tgacctcaat | 840 |
| gacgtgccca | agtctgagca | taacatgcac | acatat | | | 876 |

<210> SEQ ID NO 51
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 51

| | | | | | |
|---|---|---|---|---|---|
| aacgacgttc | agaacgcggt | ggaacggtca | attgttcgtg | tagcggacac | attcccagt | 60 |
| gggccaagca | actcagaaag | cataccagca | ctcacagcag | ccgagactgg | acatacctcg | 120 |
| caggtcgtcc | ccagcgacac | catccagacg | cgacatgtga | ggaattttca | cgttcggtct | 180 |
| gagtcatcgg | tagagaattt | tcttagcagg | tcagcttgcg | tgtacatcgt | ggagtacaaa | 240 |
| acccgggaca | cgactcccga | caagatgtat | gatagctgga | ttatcaatac | caaacaagtg | 300 |
| gcgcagttga | gaaggaagct | ggagttcttt | acctatgtca | gattcgacgt | ggaagttacc | 360 |
| tttgtcataa | ccagcgtgca | agatgactcc | acaaaacgga | acaccgacac | cccagtgcta | 420 |
| actcatcaaa | ttatgtatgt | gccgccagga | gggcccatac | cacaagcggt | ggacgattat | 480 |
| aactggcaaa | cttccaccaa | ccccagcgta | ttttggactg | aggggaacgc | gccaccaagg | 540 |
| atgtctattc | cgttcatgag | tgttggcaat | gcatacagta | acttctacga | cgggtggtcc | 600 |
| cactttctc | aaactggggt | ttacgggttt | aacaccctaa | acaacatggg | taagttatat | 660 |
| ttcaggcatg | taaacgacag | gactattagc | ccaatcaaaa | gtaaggtcag | aatatatttc | 720 |
| aaacccaaac | acgtgaaggc | atgggtaccc | agaccgccga | gattgtgtga | atacacccac | 780 |
| aaggataacg | tggactatga | accaaagggg | gtcacaacat | cacgcacttc | aatcaccatc | 840 |
| accaactcca | cacacatgga | gacgcac | | | | 867 |

<210> SEQ ID NO 52
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 52

| | | | | | |
|---|---|---|---|---|---|
| aatgacgttc | aaaatgcagt | cgagcaatca | attgttcgtg | tggctgacac | gttacccagt | 60 |
| ggacccagta | attcagagag | cataccggca | ctgacggccg | ccgagactgg | ccatacttct | 120 |
| caagttgtgc | ccagtgatac | tatacagaca | cgccacgtaa | aaaactttca | tgtgaggtcg | 180 |
| gagtcgtcag | tagagaactt | tctcagtagg | tccgcttgcg | tgtatatagt | gggatacaag | 240 |
| accacagatg | cgacccctga | caaaatgtat | gacagctggg | ttatcaacac | aaggcaggtg | 300 |
| gcgcagctaa | ggagaaaatt | agagttcttc | acctatgtta | ggtttgatgt | tgaggtcacc | 360 |
| tttgtgataa | caagcgtgca | agacgattca | actagacgga | acacagacac | ccccgttcta | 420 |
| acccaccaaa | tcatgtacgt | accccccaggt | gggcccatcc | cgcaggcagt | ggacgactac | 480 |
| aattggcaaa | cttccacaaa | tcccagtgta | ttttggacag | aagggaatgc | cccaccaaga | 540 |
| atgtccatac | cattcatgag | cgtaggtaac | gcatacagca | atttctatga | tgggtggtct | 600 |
| cacttctctc | aaactggggt | gtacggtttc | aacaccctga | caacatggg | caagctatac | 660 |
| ttcaggcatg | tgaacggcaa | gacaataagc | cctatcgcaa | gcaaggttag | gatttacttc | 720 |
| aaaccaaagc | atgtgaaggc | atgggtgccc | agaccaccgc | gattgtgtga | atacacccac | 780 |
| aaggacaatg | tggattacga | accaaaggga | gtcacaacat | cccgtacatc | tatcacaatt | 840 |
| agcaattcca | ctcatatgga | aacatat | | | | 867 |

<210> SEQ ID NO 53
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 53

| | | | | | |
|---|---|---|---|---|---|
| aacgacgttc | agaacgcggt | ggaacggtca | attgttcgtg | tagcggacac | attacccagt | 60 |
| gggccaagca | actcagaaag | cataccagca | ctcacagcag | ctgagactgg | acatacctcg | 120 |
| caggtcgtcc | ccagcgacac | catccagacg | cgacatgtga | agaattttca | cgttcggtct | 180 |
| gagtcatcgg | tagagaattt | tcttagcagg | tcagcttgcg | tgtacatcgt | ggagtacaaa | 240 |
| acccatgaca | cgactcccga | cgagatgtat | gatagctgga | ttatcaatac | cagacaagtg | 300 |
| gcgcagttga | gaaggaagct | ggagttcttt | acctatgtca | gattcgacgt | ggaagttacc | 360 |
| tttgtcataa | ccagcgtgca | agatgactcc | acaagacaga | acaccgacac | cccagtgcta | 420 |
| actcatcaaa | ttatgtatgt | gccgccagga | gggcccatac | cacaagcggt | ggacgattat | 480 |
| aactggcaaa | cttccaccaa | ccccagcgta | ttttggactg | aggggaacgc | gccaccaagg | 540 |
| atgtctattc | cgttcctgag | tgttggcaat | gcatacagca | acttctacga | cgggtggtcc | 600 |
| cactttctc | aaactggggt | ttacgggttt | aacaccctaa | caacatggg | taagttatat | 660 |
| ttcaggcatg | taaacgacag | gactattagc | ccaatcacaa | gcaaggtcag | aatatatttc | 720 |
| aaacccaaac | acgtgaaggc | atgggtaccc | agaccgccga | gattgtgtga | gtacacccac | 780 |
| aaggataacg | tggactatga | accaaagggg | gtcacaacat | cacgcacttc | aatcaccatc | 840 |

| | |
|---|---|
| accaactcca cacacatgga gacgcac | 867 |

<210> SEQ ID NO 54
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 54

| | |
|---|---|
| ggcgacaccg aaacggctat tgacaatgca atcgccaggg tagcagatac ggtggcgagc | 60 |
| ggtcctagta attcgaccag tatcccagca ctcacagcag ttgagacagg tcacacgtca | 120 |
| caagtcgagc ccagcgatac agtgcaaact agacatgtca aaaactacca ctcgcgttct | 180 |
| aagtcaaccg tggaaaactt tctaagtcgc tccgcttgtg tgtacatcga agagtactac | 240 |
| gccaaggacc aagacaatgt taataggtac atgtcgtgga caataaatgc cagaagaatg | 300 |
| gtgcaattga ggagaaagtt tgagctgttt acatacatga gatttgatat ggaaatcacg | 360 |
| tttgtaatca caagtagaca actacctggg actagcatag cacaagatat gccgccactc | 420 |
| acccaccaga tcatgtacat accaccaggt ggcccggtac caaacagcgt aacagatttt | 480 |
| gcgtggcaga catcaacaaa ccccagtatt ttctggacag aaggaaacgc gccacctcgc | 540 |
| atgtctattc cattcatcag tattggcaat gcatatagca acttctatga cgggtggtca | 600 |
| cacttttccc aaaacggtgt gtacggatac aacgccctga caacatggg caagctgtac | 660 |
| gcacgtcatg ttaacaagga cacaccatac agatgtcaa gcacaatccg agtgtatttc | 720 |
| aaacccaagc acatccgagt atgggtccca cggccgcctc gactgagccc gtacatcaaa | 780 |
| tcaagtaatg taaattttaa ccccacgaac ctgacggacg agcggtcatc catcacatat | 840 |
| gtgcccgaca ctatacgtcc agatgtgcgc accaac | 876 |

<210> SEQ ID NO 55
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 55

| | |
|---|---|
| ggtgatgtcc agaatgcagt tgaggggggca atggttagag ttgcagatac cgtgagcact | 60 |
| agcgccacca actccgaaca agtgccgaac ctgaccgcgg tggagaccgg tcacacatcg | 120 |
| caggtagtgc ccggcgacac tatgcagacc aggcacgtag tgaacaagca tgtgcgatct | 180 |
| gaatctacaa ttgaaaattt cctcgcacgt tcagcctgtg tgtactttct tgagtacaag | 240 |
| actggtacca agactgactc caacgccttc agcaattggg tcatcacaac gcgcaaggtt | 300 |
| gcgcagctga ggcgcaagtt ggagatgttt acatacttaa ggtttgatat ggagattact | 360 |
| gtggtcatta ctagctccca agaccagtcc acatcacaaa atcaaaatgc gcccgtcctg | 420 |
| actcaccaga ttatgtatgt accacctggt ggcccagtgc ccactagcgt tgatgattat | 480 |
| tgctggcaaa catccacaaa cccaagcata ttttggacgg aaggaaacgc acctgccaga | 540 |
| atgtccatcc cctttatcag cattggaaat gcttatagca acttttatga tgggtggtca | 600 |
| catttctcac agaacggagt ctatggtttt accaccttaa acaacatggg ccagctgttt | 660 |
| tttaggcatg ttaacaagcc taacccggcg acaataacca gtgtggcccg catttacttc | 720 |

| | |
|---|---|
| aagccaaaac atgtgagggc ctgggtgcct agaccgccac ggttgtgccc ttacatcaac | 780 |
| agtagcaacg tgaacttcga cccaaaacct gtggcagagg tcaggtctag catcatcacc | 840 |
| acc | 843 |

<210> SEQ ID NO 56
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 56

| | |
|---|---|
| ggtgatgtgg ttgaagccat tgagggcgca gttgctagag tagcagacac tatcagcagc | 60 |
| ggcccaacaa attctcaagc agtcccagca ctcacagcgg tggagactgg acacacctcg | 120 |
| caagttgtac caggtgatac catgcagacc agacacgtaa agaattacca ctcacgatca | 180 |
| gaatcgacca ttgaaaattt tctgagtagg gcggcttgtg tctacatggg tgagtattac | 240 |
| actacaaata cagatgagac caagagattt gctaattgga caatcagcgc aaggcgcatg | 300 |
| gtacaaatga ggaggaagct tgaaatgttc acgtacgtcc gtttcgacgt ggaggtgaca | 360 |
| ttcgtaatta ccagcaaaca ggaccaaggg aatcggttgg acaagatat gcccccgctc | 420 |
| acacaccaga taatgtacat cccgccaggt ggtcgtatac ccaaatccac cacagattac | 480 |
| gcatggcaaa cgtcgacaaa ccccagcatc ttttggacgg agggtaacgc gcccccagg | 540 |
| atgtccattc ctttcatgag cattggaaac gcatatagca atttttatga cggttggtct | 600 |
| cacttctctc aaaatggcgt gtacggatat aacacactaa accacatggg tcaattatac | 660 |
| atgcgccatg taaatggacg atcacctctt ccaatgacca gcacggtgag ggtgtacttc | 720 |
| aaacccaaac atgtgaaaac atgggtgcca cgaccccccaa gattgtgcca atacaaaaac | 780 |
| gcctcgacag taaacttttc acccacaaac atcacagaca agagggatag catcacttac | 840 |
| attccagaca ccgtgaaacc cgacatgaca acatat | 876 |

<210> SEQ ID NO 57
<211> LENGTH: 861
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 57

| | |
|---|---|
| ggggatgaga gtgcaaaggc tacagtttcc aacacacagc ctagcggtcc aagtaattct | 60 |
| gtcagcgtgc caatgcttac tgctgctgag accgggcaca catctcaagc agtacccagt | 120 |
| gacactatac agaccaggtg cgtagtgaac caacacaagc ggtcggaatc atccgtggaa | 180 |
| aatttcctgt gtcgctccgc ttgcgtatac tacacaacct atgacactca cggggatgca | 240 |
| gccgacgcaa agtacgccag ttggacgata accacccgaa aagctgcaca gctgcggaga | 300 |
| aaactagaga tgttcacata cttgagggttt gatttagaag tgacattcgt tataacaagt | 360 |
| gcacaagtaa catctaccaa taaacgtcag gacacgcctg ttctcacgca tcaagtcatg | 420 |
| tacgtgccac caggtggtgc agtacccgct agtgtggacg attatgcgtg gcagacgtcc | 480 |
| acaaacccaa gtatcttctg gacggaaggg aatgcaccag cacgcatgtc tatacccttt | 540 |
| atcagcgtgg gcaacgcata cagtagcttc tatgatgggt ggtccaactt tacacagaat | 600 |
| ggagtttacg ggttcaacac gctaaacaac atgggaaagc tatacgtacg acacgtcaat | 660 |

```
ggagctagcc ccggccctgt gaagagtacc atacggtttt acatgaagcc caaacacgtg      720
aaggcttgga tacccagacc tcctcgcctc tgcgagtacg aaaaatcagg caatgtaaac      780
ttcaaaccca agggcgtgac agagagccgg acgtctatca aattagaaaa accaaaccct      840
gcgtccaaat taatgaacca c                                                861
```

<210> SEQ ID NO 58
<211> LENGTH: 894
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 58

```
aatgatccag agcaagctat aaatcgggcg ctagcgaggg tggcagacac agttcgtagt       60
gggccgtcta actctgaaca aattcccgca ctgacagccg tggagacagg catacatca      120 caagtcgtcc ccagtgacac aatgcaaacc cggcatgtga agaattacca ctccaggtca     180
gagtcaacaa tagagaactt tttgtgtaga tcggcttgcg tgcacatcgc aacatacaag     240
gctaaaggcg gagctggaga cgtcgaccgg tacgacagct gggacataaa cataaaagag     300
ctggtacagt tgcgacgcaa gtgcgagatg tttacgtacc taaggtttga tatggaggtc     360
acctttgtga ttaccagcat acaggagcag ggcaaagcac tgacccagga catgccggtg     420
ctaacgcacc aaataatgta cgttccaccg ggcggtgccg tgcctagtgg tgcagaaagc     480
tttgcgtggc agtcatcaac gaatcccagt gtgttctgga cagaaggcaa tgcaccagca     540
cgtatgtcta tacccttat aagtattggg aacgcttaca gtaatttcta tgatgggtgg      600 tcccactta cccagaacgg tggttacggg tacaacacac taaacaaact gggtaagatc      660
tacgtcaggc atgtgaacaa acaaaccccc acgatgtca ccagcaccgt gcgaatttac      720
ttcaagccca aacacgtgcg agcttgggtg cctcgcccgc ctagactatg tccttataag     780
aacaaggcaa atgtaaactt tgaagttact agtgtaacca ctgccagaac gagtcttaat     840
gatgtcccca ctcccaacca cagtagtagc gtgcacctgc gcatgcacac gcac           894
```

<210> SEQ ID NO 59
<211> LENGTH: 882
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 59

```
ggtgatgacc aacacaagac caatacagtg acagacacag agcagagtgg cccgtcaaat       60
tccgaacgcg tcccagccct cacagcagtg gagactggcc acacttcgca ggtcgtaccc     120
agcgacacag tgcaaactcg ccacgtacgc aattaccact caaggacaga gtctaccta     180 gagaattttc ttggtaggtc agcatgtgtg cacatcgaca catacaaggc taagggtgaa     240
aaaggatctt ctgagaggta cgcgtcatgg gagataacta cagggagat ggtgcaattg      300 cgccgaaaat gtgagatgtt cacatatatg aggtatgacg tggaaataac atttgtgata     360
accagctacc aggagcaggg cacacgattg gcccaggaca tgcctgtact aacacaccaa     420
atcatgtacg tgcccccggg tgggcctgtg ccaacaagca cggagagcta tgcatggcag     480
acctcaacga accctagcgt cttttggact gagggcaacg caccaccgcg tatttccata     540
```

```
cccttcatca gcataggaaa tgcgtactgc aacttttatg atgggtggtc acatttctca      600
caagatgggt cctatggcta cacagcgctc aatagaatgg ggaaaatata tattagacat      660
gtaaataagg agaccccac acaggtcatt agtaccgtga ggatgtacat gaaaccaaaa      720
cacattcgcg catgggtgcc cagacccccc cggctgtgca aatacctaca ctcaggcaac      780
atgaacttca acgtggagga cattacagag gagcggaacg atataaacca tgtacccacc      840
cccagccaca gcagtagtgt gcgtgtgcgt cttggcacca ca                        882
```

<210> SEQ ID NO 60
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 60

```
ggtgatgttg aggactcagt aaacagagca gtggttaggg tagcagacac catgccaagt       60
ggaccatcca attcgcaggc agtacctgcc ttgacagccg ctgagacagg tcacacgtct      120
caagtggtgc ctggtgataa catccaaaca cgtcatgtgc acaactacca ctccagaact      180
gaatccagta tcgaaaattt cttcgggcgt tccgcatgtg tagtggtcaa acatatataaa     240 atgggtcaaa aagttgtagc tacagacaga tatgatagtt ggatgatttc cattagggac      300
atggtacaac taagacggaa gtgtgaaatg ttcacgtaca tgagatttga tttagagatc      360
accttcgtgg tcacgagtta ccaacaatat agtacatcct tgacacagga catgccagtg      420
atcacgcatc agttcatgta tgtgccgcct ggggtccgg ttcctgagag tgtaaatagc       480
tacgcttggc aaacgtcaac caatcccagt atattctgga ctgagggtaa tgccccagca      540
aggatgtcca ttcccttcat cagtgttggg aacgcatata gctgcttcta cgatggctgg      600
tcacacttca cacagaaggg ggtttatggt tataacactc tcaacaacat gggcaaattg      660
tacatgcgac acgtgaacaa aaatagcccc acagagatca taagcactct tcgtgtgtat      720
ttcaagccaa agcacgtgaa agcgtgggta cccagaccac ccaggctatg tccatacaaa      780
tataaggcaa atgttgactt tgaagtgact ccaatcacag acaagcgaga ctccataacc      840
agcataccag tccccaagca cactcat                                        867
```

<210> SEQ ID NO 61
<211> LENGTH: 861
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 61

```
ggggataacc aggatcggac ggtcgccaac acacagccta gcggtccgtc caactccacg       60
gaaattccag ccttaacagc ggtggaaacg ggcacacct cacaagtgga tcccagtgac      120
actatccaga ccaggcacgt ggtaaacttc cactcacgtt ctgagtccac tatagaaaat      180
ttcatggggc gtgcagcatg tgtgttcatg gatcagtata aaatcaatgg agaagagacg      240
tccactgata ggttcgcagt gtggaccata aacataaggg agatggccca attaagaagg      300
aagtgtgaaa tgttcacgta catgcgtttt gatatcgaga tgacaatggt cattaccagc      360
tgtcaagacc agggaacgat actagatcag gacatgcctg ttttgacgca tcaaattatg      420
tacgtcccac caggggcccc aatcccagcc aaagtagata gttacgagtg gcagacatca      480
```

```
acaaacccca gcgtcttctg gacggaaggt aatgcaccac cgcgtatgtc tattccattc      540
attagcgtcg gcaatgctta tagctcattt tacgatggtt ggtcacactt cacacaggac      600
ggtacctatg ggtatacaac ccttaatgca atggggaaac tgtacattag gcatgtgaat      660
aggagcagcc ctcatcagat aaccagcacg atcagagtat acttcaaacc caaacacatc      720
aaggcatggg tgccccgacc accacgattg tgcccgtata taaacaaaag ggacgtaaac      780
tttgtagtca cggagataac agactcaagg acttccatca ctgatacacc acacccagaa      840
catagtgtcc tggcaacgca t                                                861
```

<210> SEQ ID NO 62
<211> LENGTH: 879
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 62

```
ggagacatcg tggaggctgt ggagggagcc atctcgcgag tggcagatac tgttagtagt       60
gggcccagta actctcaagc agtaccagcc ctcacagcag tcgaaacggg tcacacttct      120
caagtcaatc ctagtgacac catgcagacc agacacgtga caaattacca ctcgcggtca      180
gaatccagca tagaaaattt ccttagccgc tctgcttgtg tgtatatggg cgaatacagc      240
acacaagcat cagatgagac caaaaagtac atgtcatgga ccataagccc aaggaggatg      300
gttcaaatgc gcaggaagtt tgagctcttc acttacctgc gttttgatgt ggagattact      360
tttgtaatca ccagcagaca agtcaaggta gggacacaat taggccaaga tgccccccg       420 ctaactcacc aagtcatgta tatacccca ggaggcccag tacctgattc agttggtgat      480
tacgcatggc agacttccac taaccctagt atcttttgga ccgaaggtaa tgcatcaccc      540
aggatgtcaa tacccttcat tagcataggt aacgcctata gcaacttta tgacgggtgg      600 tcgcattttc accagaatgg cgtctatgga tacaacacgc tgaaccatat ggggcaactg      660
tacgtgcggc atgttaacgg cccttcacca ttaccagtga caagcacagt cagggtctac      720 ttttaaaccca aacacgtgaa ggcttgggta ccgagggcac ccaggctatg tcaatatgta      780
aatgcatcca ctgtgaactt cgagccaaca gacatcactg agtcacgcac tgacatcaac      840
catgttccag acaccgtgaa gccagatctc caaacatac                             879
```

<210> SEQ ID NO 63
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 63

```
ggggacgtgc acgatgcggt ggttggggcc atgacccgtg ttgcagacac gataagtagt       60
gggccaagca attcagaaag cgtgccagca ttgactgcag ccgagacagg acacacatca      120
caggtagtac cgagtgatac catgcagacc agacatgtgc ggaatttcca cacaagatca      180
gagtcttcaa tagaaaattt catgagtcgc tccgcctgtg tctactatac taagtataag      240
accaaagacc cggacccaac ggagatgtac tctagttgga aggttaccac caggcaagtg      300
gcacaactca ggaggaagat ggagatgttc acttatttgc gctttgacgt agaagtgaca      360
```

| | |
|---|---|
| tttgtaataa ctagctcgca agatcagtcc acgagtgttg cacaggacgc acctgttctc | 420 |
| actcaccaaa tcatgtacat cccacccgga ggcccggttc ccaaatcagg tagggattac | 480 |
| tcatggcaat cctgtactaa cccaagtgtt ttctggactg agggtaatgc accaccacgc | 540 |
| atgtgtattc cgttcattag tattggaggg gcatatagtt cattctatga cgggtggtcc | 600 |
| cactttaacc aacaaggtcc gtacgggtat aacactctca atgacatggg tcaactgtat | 660 |
| tttaggcatg tgaacgaggg tagcccaggg gcggtaacaa gctacatcag aatatacttc | 720 |
| aaacctaaac atattagagc atgggtgccc agaccaccta gattgtgtca gtatgagaaa | 780 |
| caagggagcg ttgacttcaa ggtgcaggga gtaactgatg ctcgtacctc gctcaccact | 840 |
| aca | 843 |

<210> SEQ ID NO 64
<211> LENGTH: 885
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 64

| | |
|---|---|
| aatgacccag cacaagccgt gttgagtgcg atcggtcgtg tcgctgacac cgtcgctagc | 60 |
| gggccatcga attcagagag agttccagtt ctaaccgctg cggagacagg tcatacctca | 120 |
| caggtggttc ccagcgatac cattcagacg cgccacgtcg tcaacttcca cacaagatcg | 180 |
| gagtcaacaa ttgaaaattt tatgtgtcgc tccgcctgcg tgtacatcgc ccggtacggt | 240 |
| actgaaaagc aagggaaaca aatatccaga tacaccaagt ggaagatcac cactaggcag | 300 |
| gtggcgcaac tgcgcaggaa gatggagatg ttcacataca tgcgatttga tttggaaatg | 360 |
| acatttgtaa tcacaagctc ccagcgtatg tcaacggcat atgattcaga cacaccagcc | 420 |
| ctcacccacc aaataatgta cgtgccacct gggggcccgg agccccgtca ttatgaggat | 480 |
| ttcgcctggc agacatccac aaatccaagc atattttgga ccgaaggtaa cgcaccacca | 540 |
| cgcttatcaa tcccatttat gagtgtggga aatgcctatt gcaattttta tgatgggtgg | 600 |
| tctcactttt cacaaagtgg agtgtatggg tttaccacct aaataacat gggacaactg | 660 |
| ttcatgcgcc atgtcaataa gtcaacagcg caccccattg atagtgtggt gcgagtttat | 720 |
| tttaaaccaa agcatgttaa ggcgtgggtt ccaagacctc cccggttgtg cccatacatc | 780 |
| tatgcaagga acgtggattt tgagccacaa ggtgtcactg aatcaagaga aaagataaca | 840 |
| ctagataggg atactcacac ccctatgcgc acatgcgggc cgttc | 885 |

<210> SEQ ID NO 65
<211> LENGTH: 882
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 65

| | |
|---|---|
| ggagatgtct gtgaggaagt agagagggct attgtcaggg ttgcagatac tgtcggacgc | 60 |
| ggtcctgcta acactgagag tgtaccagcg ctgactgcag ttgaaactgg acacacttca | 120 |
| caagttgtac ccggggacac catgcaaacc agacatgtta aaaactttca cacgcggtca | 180 |
| gaatcatctg tggaaaattt catgtgcaga gcagcgtgtg tgtattatgt ggattaccac | 240 |
| acacaaaatg acagtgagga tgaaaaatat gcatcttgga ttatcaacac gagacaggta | 300 |

```
gcacagctac gcaggaaaat tgagctgttc acatacacta ggtttgatgt cgaaatcaca      360
ttcgtgatca ccaccacaca gcagcaatcc acagctccca accccgacac tcctctgctg      420
acacaccaaa tcatgtatgt gcccccgggt ggcccagtgc aaatagtgc taccgattat       480 tgttggcaat catccacaaa tcccagtata ttctggaccg agggtagcgc accacccaaa      540
atgtcaatac cctttataag tgtgggaaat gcatacagca gttttttatga tgggtggtca    600 catttcactc aaaacggggt gtacgggttc aacactctga acaatatggg caaattatac     660
ttcaggcacg taaatgacaa caccgtaggg ccatatgtga gcaaagcccg catttatttc    720
aaaccaaagc atgtgcgtgc gtgggttccc aaacctccca ggctctgtga atacaacaat     780
cgagccaacg tgaactttga accacgaggg gttaccgatg ccaggtctag tatcacggcc    840
acaaccgaca cgatcactga gagcacaggg atgcaaacga ct                        882

<210> SEQ ID NO 66
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 66
aatgatccag caactgccat agttagatcg gttgagagag tggctgatac catagcaagt      60
ggacccacta actcagagag agtgccagca ctaaccgccg ttgaaacagg tcacacctca     120
caggtagtcc cgagcgacac catgcaaact aggcatgttg tgaaccatca cattagatca     180
gagtcctcta ttgaaaactt cctgagcagg tccgcctgcg tgtacatcga catgtatggg     240
acaaaagaga atggtgacat caagcgcttc accaactgga gaataaacac acgtcaggtc    300
gtgcagctaa ggcgcaagct ggaaatgttt acatacatta gatttgatgt tgaaatcact     360
tttgtaatca ctagcacaca gggaacaccg actcaaaaga acaaggatac cccagttctt    420
acacaccaaa tcatgtatgt gccaccaggg ggcccaatcc ctgtatctta tgaagattat     480
tcttggcaga cctctacaaa tcctagtgtt ttctggacag aagggaatgc cccagcccgt     540
atgtcaattc ccttcatgag cgtagggaac gcctattgta actttttacga cgggtggtca    600 cacttctcac aatcgggtgt gtatgggttc actacactca ataacatggg tcagttgtac    660
tttcgacacg tgaacaagga cacccttgga ccatacaata gcacggttcg ggttacttc    720 aaacccaaac atgtgaaggc atgggtaccc agaccaccgc gcctgtgcga ctacgtttac   780
gcacataatg ttgacttcac accaaaaggg gttactgaca gcagggacaa gatcaccctg    840
gaccgtgatg aacacgtgcc gtcagtggtt aaccac                              876

<210> SEQ ID NO 67
<211> LENGTH: 870
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 67
ggagatgatc caccgcattc gatctcaaac acggttgcaa acaccaaccc tagtggtcca     60
accaactcag aaaggatccc agcgctcaca gcagcggaaa ctggtcacac ctcgcaggtg    120
gtcccgagtg ataccgtaca aactcgttgt gtgaaaaact tccacactcg atcggagtca    180
```

-continued

```
tcaattgaga acttttttgtg cagatcagct tgcgcacaca tgtcatcgta tgaggccttc      240
ccaacaacaa cacaagacgg tacacaaagg ttcgccaatt ggacgattag tgtgaaagac      300
atggtgcagt tgaggaggaa atgtgagatg ttcacgtact taagatttga catggaggtg      360
acttttgtga taactagtgt gatcgaaact acaaaaggga aagtaccggc accagcagtc      420
acacaccaag taatgtacat tccaccaggc ggacctattc cagctagcgt tgaaagttat      480
gcctggcaaa catccaccaa cccaagcgtg ttttggacag aagggaatgc tcccccacgc      540
atgtctatac catttatcgg cattggtaat gcctacagca tgttctatga cggatgggcc      600
agtttcagac aatcgggtgg atatggatac agcaccctga accacatggg ccagatattc      660
gtaagacacg tgaatgcaac cataccaaac ttgatcagca cagtcaggat atatttcaag      720
cccaagcacg ttagggcttg gattcctaga ccgcccaggt gtgtcagta catttacaag       780 gcaaatgtag actacgcagt gtcaaatatc actgaaaagc gagatagtat aagatggaca      840
ccaacaaccg gtccgtcaat gacatcccac                                       870

<210> SEQ ID NO 68
<211> LENGTH: 855
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 68
ggtgacgacg caaggactgt tagcgacaca caaaagagcc agccatctaa ctctgagcaa       60
gtgcctgcct taacagcggt tgagactgga cacacctctc aagttgagcc cagtgataca      120
gtacagacac gacatgttgt caactcacac agtaggacag agtcgacaat tgagaatttc      180
tttgggaggg ctgcgtgtgt gagggtgaga gagtactcta tagggcatga tttggcagcg      240
gacgaaacat atgatagctg ggccattaca gtgcgagaca tggtgcagct tcgtaggaag      300
tgtgagatgt tcacatacat gaggtttgac ttggaagtga cgctagtcat caccagctat      360
caagaaccag ggacaatcac cacccaggat atgcccgtcc taaccaccaa gattatgtat      420
gtgccgccag gaggcccggt cccagccaag gctgacagtt acgcgtggca aacgtcaaca      480
aatcccagta tattctggac cgaaggcaac gctccacctc ggatgtctat cccatacatt      540
ggcatcggca atgcatatag cagctttttat gacgggtggt cgagcttcaa caactcgggt      600
gtgtatggct acacaaccct gaataacatg ggtaaactgt acttcagaca cgtgaacaaa      660
cacagcccaa acactattaa gagcactgtg aggatatatt tcaagcccaa gcacgtccag      720
gcgtgggtcc caagaccacc gcgcttgtgc ccgtatctga ataagaggga tgtcaacttt      780
gaagtgcaac ccgttacgag caagagagac agtattaact gggtgccaca aacaaaccgc      840
caagtgtaca atcat                                                       855

<210> SEQ ID NO 69
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 69
aatgaaccta gtagtgccat tgagagagca attgtgcgcg tagcagatac tatggccagt       60
gggcctgcaa actcagagca aatccctgcc ctaaccgctg ctgagactgg tcacacctcg      120
```

```
caagtggttc ccagcgacac tatgcaaacc cgccatgtat gtaactacca caccagatct     180
gaatcatcga tcgagaactt cctatgcagg gctgcatgtg tctacatagt gagttacaaa     240
acacagggcg acgaacaaac cgacaaatac gctagttggg agatcaacac gcggcaggtg     300
gcacagttaa ggagaaaatt ggaattcttt acttacataa gatttgacat ggaggtaaca     360
tttgtgatca ctggttcaca agacaccagc acacagacta acacggatac gccagtgcta     420
acccatcaaa ttatgtatgt gcctcccggt ggtccagtac cgacatcagc cacagattac     480
agctggcaga catctacaaa tcccagtgtg ttctggacag aagggaatgc gcctccccgt     540
atgtccatac ccttcatgag cataggcaat gcgtatgcta atttctatga tgggtggtcg     600
cactttagcc agtcaggggt gtatggttac accacactca ataatatggg taccctgtat     660
ttcaggcacg tgaacaactc gaccatcggg ccttacacca gtgcagttag gatatatttc     720
aagccaaagc acgtcaaagc gtgggtgcca cgaccgccac ggttgtgcga ttacaaacac     780
aaaaagaacg tagactttac tcccacaggt gtgaccacaa ctagagacaa gataaccttg     840
gacaagggga ctcacgtgcc gagcgtatgg aacaca                                876
```

<210> SEQ ID NO 70
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 70

```
aatgaccccg aagtgcact  taataaagca gtgggcaggg tagctgatac tatagctagt     60
gggcccgtca atacagagca aattcctgca ttgacagcag tggagacagg gcatacatct     120
caagtggtac ctagtgacac aatgcaaacc cgacacgtgg tcaacttcca tactagatca     180
gagtcatcgt tacagaactt catggggaga gcggcatgtg tatatatcgc ccactatgcc     240
acagaaaagg ctaatgatga tttggacaga tacactaact gggagatcac aactaggcag     300
gtggcacagt tgaggcgcaa gttggagatg tttacgtata tgagatttga cctcgagatt     360
acattcgtaa tcaccagctc ccagcgtact tccaacaggt atgcgtcaga ctcccccccca     420 ttaacacatc aaataatgta cgtgccgccg gggggtccaa ttcccaaggg ttatgaagac     480
tttgcctggc agacgtccac caacccaagt gtgttttgga ccgaaggtaa cgcccctcct     540
aggatgtcaa taccattcat gagcgttggc aacgcatatt gtaactttta tgatggatgg     600
tcccatttca gtcagagcgg tgtgtacggg tacactacat tgaacaacat ggggcgctta     660
tattttagac atgtaaacaa atcaacagga tacccagtaa atagtgtcgc ccgcgtctat     720
ttcaagccca agcatgtgaa ggcatgggta cctcgcgcgc cacgcttatg tccatatttg     780
tatgctaaaa atgtcaactt tgatgtgcaa ggcgtgaccg agtcccgggg taagatcact     840
ctcgaccgtt cgactcacaa ccccgtgtta accact                                876
```

<210> SEQ ID NO 71
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 71

```
aatgaccctg aaggtgcgct caacaaggcg gtgggcagag tggctgatac aatagccagt    60
gggcccgtca acactgagca aattcccgca ttgacagcag tggaaacagg gcacacatct   120
caagtagtac ctagtgatac aatgcaaact cgacacgtgg tcaacttcca caccagatca   180
gaatcatcgt tggagaactt catgggaaga gcagcgtgtg tgtatatcgc tcattatgct   240
acagagaagg ctaatgatga tttagacaga taccaaact gggaggtcac aaccaggcag    300
gtagcacagt tgaggcgtaa actggagatg ttcacgtaca tgaggtttga cctcgagatc   360
acatttgtaa tcaccagctc ccagcgcact tcaaccaagt atgcgtcaga ttcccccca    420
ctaacacacc agataatgta tgtaccgccg gggggcccga tccccaaggg ttatgaagat   480
tttgcctggc agacgtccac caacccaagt gtattttgga cggaaggtaa cgccccccct   540
aggatgtcga taccattcat gagcgttggt aacgcatact gcaacttta cgacggatgg    600
tcccatttca gccagagcgg tgtgtacggg tacactacat gaacaacat ggggcacttg    660
tatttcagac atgtaaacaa atcaactgca tacccagtta acagtgttgc ccgcgtctac   720
ttcaagccca agcacgtaaa ggcttgggtg cctcgcgcgc cacgcttatg tccatatttg   780
tatgcaaaaa atgtcaattt tgatgtacaa ggtgtgaccg agtctcgggg aaaaatcact   840
cttgatcgat cgactcacaa ccctgtgtca accacg                            876
```

<210> SEQ ID NO 72
<211> LENGTH: 877
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 72

```
aacgaccccg aacatgcgtt aaacaacgcc attggtagag tggcagatac gatcgccagt    60
gggccggtga actcggaacg catacctgca ctaaccgcag tggagacagg acacacgtct   120
caagtggtgc caagcgacac catgcaaaca aggcacgtag tcaacatgca tacaagatcc   180
gaatccacca tcgaaaattt catgggaagg gctgcttgtg tatacattgc gcaatacgcc   240
actgataagg ccagtgatga tctggacagg taccagct gggagatcac tacgagacag    300
gttgcgcaat tgaggagaaa gctggagctg tttacataca tgaggtatga cttagaagtt   360
acctttgtca ttaccagttc ccagcgcact tcgactacat atgcatcaga ctccccgcca   420
ttgacccacc aaattatgta tgtgcctccc gggggcccta ttcccatagg cacgaagac    480
ttcgcctggc agacttcaac aaaccccagt gtctttgga ctgaaggaaa tgccccacca   540
cgtatgtcca taccattcat gagtgtgggc aatgcctact gcaattttta cgatgggtgg   600
tcacatttta accagagtgg ggtgtatgga tacactacac taaacaacat gggtcgctta   660
tatttcaggc atgtaaacag atctactgcc tacccagtta atagtgttgc acgtgtttac   720
tttaaaccca aacacgtcaa agcctgggtc ccacgagcac cacgattgtg cccatactg    780
tatgctaaga acgtgaactt taatgtgcaa ggtgtgactg actcccgaga caagataacc   840
gtagaccgaa ccaaccatgt acgtatgcgc accacag                            877
```

<210> SEQ ID NO 73
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 73

```
aacgaccccg aacacgtgtt aaacaatgcc gttggcagag tggcagatac aatcgccagc      60
gggccggtga actcggaacg cgtacctgca ctaactgcag tggagacagg gcatacgtct     120
caagtggtgc caagcgatac tatgcaaaca agacacgtag tcaacatgca cacaagatct     180
gaatccacta tcgaaaattt catgggaagg gctgcttgtg tatacatcgc acaatacgct     240
actgacaaag ccagtgacga tttggatagg tacaccagct gggaaatcac cacgagacag     300
gttgcgcaat tgaggagaaa gttggaaatg ttcacataca tgaggtatga cctggaagtc     360
acctttgtta tcaccagttc ccagcgcacc tcgactacat atgcatcaga ttccccacca     420
ttgactcatc agatcatgta cgtgcctccc ggggcccca ttcctatagg atacgaggac      480
ttcgcctggc aaacatcgac taaccctagt gtcttttgga ctgaaggaaa tgccccacca     540
cgcatgtcca ttccatttat gagtgtgggc aatgcctact gcaattttta cgatgggtgg     600
tcacacttta gccagagtgg ggtgtacgga tacactacac taaataatat gggtcgtctg     660
tatttcaggc atgtaaacaa atctactgcg tacccggtta atagtgttgc acgtatttac     720
ttcaaaccca aacatgttaa agcctgggtc ccgcgagcac cacgactgtg cccatatttg     780
tatgcaagga acgtgaactt taatgtgcaa ggtgtgactg actcccgaga aaagataacc     840
atagaccgaa ccaaccatgt gcccatgcgt aacaca                              876
```

<210> SEQ ID NO 74
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 74

```
ggggacacgg aacatgcagt tgagtcagct atctccaggg tagcagatac cattagctca      60
ggtcctagta acactgttgc tataccagcg ctcaccgcgg cagaaacggg ccacacatcg     120
caagtcaccc ccagcgacaa tcttcagacg cgccatgtta agaactatca ctcccgctct     180
gagtcaacta ttgaaaactt cctgtgtaaa tccgcgtgtg tgcatattgc gtcatacaac     240
gcatacggtg atgttggatc agacagtaga tatgatagtt gggagatcaa catcagggaa     300
atggtgcagt taaggaggaa gtgcgaaatg ttcacctatc tcagatttga catggaggtg     360
acatttgtca tcactagcaa gcaagatcaa gggacttcgc tatcacaaga catgccagtg     420
ctaacacatc agatcatgta cgtgccgcca ggcggatccg tgcccactag cgtccagagc     480
tacgcatggc aaacatccac caacccgagc gtgttttgga cagagggcaa tgcccctgct     540
agaatgtcca tcccattcat tagcataggg aatgcataca gcagcttcta cgacgggtgg     600
tcacatttca cccaacaagg tggctatggc tataatacac tgaacaagat gggtaagttg     660
tttgtaaggc atgtgaataa agaaacacca acccatgtga cgagcacgat acgtgtatat     720
tttaaaccaa agcatgttag agcgtgggtg ccaaggccac ctagattgtg cccgtacatc     780
aataaagcgg actgtaactt cgctgttaca ccactcacca acagcggtt aggaatcaac     840
gatgtcccgc ggcccagcca cacattacat actcat                              876
```

<210> SEQ ID NO 75
<211> LENGTH: 875
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 75

| | | | | | |
|---|---|---|---|---|---|
| aacgaccccg | caaccgctat | tgaaggagca | gtccggcgag | tggcggacac | gatccagagc | 60 |
| ggaccgagca | attcggagcg | ggttccagcg | ttaacggccg | ttgagacagg | tcacacagca | 120 |
| caggttaccc | cgagtgatac | aatgcaaact | agacatgtac | acaacttcca | caccagatcg | 180 |
| gagtctagca | tcgagaactt | cctcagtaga | gcagcttgtg | tgtacatagg | gaaatatagt | 240 |
| agcaatgcaa | caacacaaga | tgaacaatac | atgtcatgga | caattaatac | cagacagatg | 300 |
| gtgcagctga | gacgcaaatt | cgaaatgttc | acctacctac | gcttcgacgt | agaagtcact | 360 |
| tttataataa | catcgcacca | agatcaaggg | acacagttca | accaggatgc | gcccgtaatg | 420 |
| tgccaccaaa | tcatgtatgt | gccacctggt | ggcccggtgc | ctaagagtgt | tgatgacttc | 480 |
| acatggcaaa | cctctactaa | ccctagtgtc | ttttggtcag | aaggcaatgc | accaccgaga | 540 |
| atgaccattc | cattcattag | tatagggaac | gcctacagca | gcttttatga | tggctggtca | 600 |
| cacttctctc | aaaatggggt | ttacgggttt | aatgcactca | ataacatggg | taaactgtat | 660 |
| gtgagacaag | tgaacctaaa | agcccctatg | ccagtcagca | gtacagttag | gatctatttc | 720 |
| aaacccaagc | atatcaaagc | ttgggtaccc | agaccaccgc | gtctatgtaa | gtacctgaag | 780 |
| tctgggagtg | tcaattttga | gcccactgat | ttgacagaaa | aacggaaatc | cagaaagtac | 840 |
| atcccaaaaa | ctttcagacc | agatgtgaga | accat | | | 875 |

<210> SEQ ID NO 76
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 76

| | | | | | |
|---|---|---|---|---|---|
| ggtgatgtgc | atgatgcagt | tgtgggtgcg | atgtcgcgcg | tcgctgatac | agtagcaagt | 60 |
| ggccctgcaa | actctgagag | cgtgcctgct | ctcactgcgg | tagaaactgg | acacacgtca | 120 |
| caggtgacac | caagtgatac | aatgcagacc | agacacgtac | acaacttcca | cacacggtcc | 180 |
| gaatcgtcaa | tcgagaactt | cttaagccgc | tctgcatgtg | tctattatgc | aacgtacaaa | 240 |
| acaacagcca | gcagacccga | agaccaattc | gttaggtggt | ccatttcata | ccgccaggtg | 300 |
| gcccaactgc | gcaggaaaat | ggaaatgttc | acctacctgc | gctacgatgt | ggaggtcact | 360 |
| tttgtgatta | caagttctca | ggaccccatcg | accaacgtaa | gccaggatgc | tcctgtactc | 420 |
| acacatcagt | taatgtacgt | accccccggg | ggtccagtgc | ccaaaaattc | aagagactat | 480 |
| gcatggcaaa | catccaccaa | cccgagtgtg | ttctggaccg | aggggaacgc | accaccaagg | 540 |
| atatccatcc | cctttatcag | tgtgggcaac | gcatacagtt | gcttttatga | tggatggtcc | 600 |
| cactactcac | agacgggggt | gtatggttac | aacaccttaa | acgacatggg | ccaattattt | 660 |
| gtcaggcacg | tgaatgaggc | aagcccgggt | gcggtgtcaa | gtgtagttag | gatttacttc | 720 |
| aaacccaaac | atgtgaaggc | atgggtcccg | agaccaccac | ggttgtgcca | atatgttaac | 780 |
| gcagcaacgg | tgaacttcac | tcctgaaggg | gtcactaagg | cacgtactga | tctcatgaca | 840 |
| aca | | | | | | 843 |

<210> SEQ ID NO 77

<211> LENGTH: 915
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 77

| | |
|---|---|
| ggaatagaag aaactattga cacagtgatc accaacgctt tacaactgtc tcagcccaaa | 60 |
| ccgcagaaac aactcactgc tcaatccacc gcctcatcca gcggagtcaa ttcacaagaa | 120 |
| gtgccagcat tgactgctgt ggagacggga gcttctggtc aagccatacc cagcgacgtg | 180 |
| attgagacca gacatgtcgt caattacaaa actagatctg aatcaaccct tgagtcattc | 240 |
| tttggtagat cagcatgcgt aaccatactg gaagtagaga acttcaatgc cactaccgaa | 300 |
| tcggacaaga aaaagcaatt caccaccctg gccaatcacat acaccaacac agtccagttg | 360 |
| cgcaggaaat tggaattctt tacatactcc agatttgatc tggaaatgac ttttgtcata | 420 |
| actgagaggt accacacaag taatacagga catgctagaa atcaagtgta ccaaataatg | 480 |
| tacataccac cggtgcgcc aaggcccaca gcacgggatg attacacctg caaagttca | 540 |
| tccaatccat cagtgtttta cacatatggt agcgcgcctc ccagaatgtc tatcccatat | 600 |
| gttggcattg ccaatgcata ctcacacttt tatgacgggt ttgcccgagt tcccctgaaa | 660 |
| gatgatacaa ctgactccgg tgacactttt tatggattgg tcaccatcaa tgactttgga | 720 |
| acattggctg tgagggtggt gaatgagttc aaccctgcaa ggataacatc aaaggtcaga | 780 |
| gtttatatga agcccaaaca tgtgaggtgt tggtgtccta ggccaccgcg cgcagtgccc | 840 |
| tatcgtggtg aaggggttga tttcaaacaa gattcaatca cgccaataac agcagtcacc | 900 |
| aatattaata ccttc | 915 |

<210> SEQ ID NO 78
<211> LENGTH: 936
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 78

| | |
|---|---|
| tcaaaccact tacatggagc agaggcagcc tatcaggtgg agagtatcat caaaacagca | 60 |
| actgatactg tgaagagtga gattaacgcc gaacttggtg tggtcccctag tctaaatgca | 120 |
| gttgaaactg gtgcaacttc caacactgaa ccagaagaag ccatacaaac tcgcacagta | 180 |
| ataaatcagc atggtgtgtc ggagacgtta gtggagaatt ttcttggtag ggcagcccta | 240 |
| gtgtcaaaga aaagtttga atacaagaat catgcctcat ccagcgcagg acacacaaaa | 300 |
| aacttttta aatggacaat taatactaag tcttttgtcc agttaagaag aaagctggaa | 360 |
| ttattcacat accttaggtt tgatgctgaa atcaccatac tcacaactgt ggcagtaaat | 420 |
| ggtaataatg acagcacata catgggtctc cctgacttga cactccaagc aatgtttgta | 480 |
| ccaactggtg ctcttactcc aaaggagcag gattcatttc attggcaatc aggcagtaat | 540 |
| gctagtgtgt tctttaaaat ttctgatccc ccagctagaa tgactatacc ttttatgtgc | 600 |
| atcaactcag catattcagt tttttatgat ggctttgctg gatttgagaa aaatggtcta | 660 |
| tatggaataa acccagctga cactattggc aacttgtgtg tcagaatagt gaatgaacat | 720 |
| caaccagttg gttttacagt gaccgttagg gtttacatga agcctaaaca tataaaagca | 780 |
| tgggctccac gaccaccgcg aacctatgcca tacatgagca ttgctaatgc aaattacaaa | 840 |

```
ggtagagata cagcaccaaa cacacttaat gccataattg gtaatagagc gagtgtcaca      900
actatgcctc acaacatagt aaccaccggt ccgggt                                936
```

<210> SEQ ID NO 79
<211> LENGTH: 861
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 79

```
aatgaccagc acaatggggc gatcgttgcc aacacaacag ctagcggacc ttctaattcg       60
gaaagcatac cggcacttac tgcggctgag actggccaca catcgcaggt tgtccctagc      120
gacaccatcc agacaagaca tgtgaaaaac taccactcgc gttcagagtc caccatagag      180
aacttcctgt gtagatctgc ctgtgtgtac tacaccacgt acaacactca gggcgagcaa      240
gcacatgata aatacgcaag ttggccaatc acgactagaa aagttgccca actgcgcagg      300
aagctggagt tctttaccta cctgcggttt gatctcgaga tcacgttcgt gatcacgagc      360
gcccagatca catccacgaa ccaaaaccag gatgccccag tactcacaca tcaggtgatg      420
tatgtacccc cagggggggt ggtaccgcgc agtgtggatg actatagttg cagacttcc      480 accaatccca gcatcttctg gacagaaggg aacgcacctc ctcgtatgtc aataccattc      540
attagtgtgg gcaacgccta cagcagcttt tacgacgggt ggtcacactt tgaacaaacc      600
ggggtatatg gattcaatac ccttaataat atggggactt tgtacgccag gcacgttaac      660
ggtgctagtc ccgggccagt caagagcacc attaggatat atatgaaacc taaacatgtg      720
aaagcgtgga tacctaggcc cccacggttg tgcgactatg tgaaatctgg caacgtcaac      780
tttgaaccaa aaggagtcac cgagagcaga ccatctataa agttagaaaa gacctcaagt      840
gggcacaggc tgacaaccca c                                                861
```

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 80

Met Tyr Val Pro Pro Gly Gly
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 81

Met Tyr Xaa Pro Xaa Gly Ala
 1               5

<210> SEQ ID NO 82

```
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 82

Phe Gly Xaa Gln Ser Gly Ala
 1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa  = any amino acid

<400> SEQUENCE: 83

Thr Ala Xaa Glu Thr Gly His
 1               5

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 84

Thr Ala Val Glu Thr Gly Xaa
 1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 85

Gln Ala Ala Glu Thr Gly Ala
 1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid
```

-continued

```
<400> SEQUENCE: 86

Met Xaa Xaa Pro Pro Gly Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 87

Met Tyr Val Pro Pro Gly
1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 88

Met Phe Val Pro Pro Gly
1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 89

Met Tyr Val Pro Thr Gly
1               5
```